(12) United States Patent
Stringham et al.

(10) Patent No.: US 9,149,321 B2
(45) Date of Patent: *Oct. 6, 2015

(54) SYSTEM AND METHOD FOR COOLING OF A HEATED SURGICAL INSTRUMENT AND/OR SURGICAL SITE AND TREATING TISSUE

(71) Applicant: Domain Surgical, Inc., Salt Lake City, UT (US)

(72) Inventors: Mark Stringham, Kearns, UT (US); Preston Manwaring, Farmington, UT (US); Kim Manwaring, Phoenix, AZ (US); Philip Eggers, Salt Lake City, UT (US)

(73) Assignee: Domain Surgical, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/555,303

(22) Filed: Nov. 26, 2014

(65) Prior Publication Data

US 2015/0088114 A1     Mar. 26, 2015

Related U.S. Application Data

(63) Continuation of application No. 13/441,823, filed on Apr. 6, 2012, now Pat. No. 8,932,279.

(60) Provisional application No. 61/473,725, filed on Apr. 8, 2011, provisional application No. 61/505,059, filed on Jul. 6, 2011.

(51) Int. Cl.
*A61B 18/04* (2006.01)
*A61B 18/08* (2006.01)
(Continued)

(52) U.S. Cl.
CPC ........... *A61B 18/082* (2013.01); *A61B 18/1402* (2013.01); *A61B 17/320068* (2013.01);
(Continued)

(58) Field of Classification Search
CPC .......... A61B 2018/00005; A61B 2018/00011; A61B 2018/00017; A61B 2018/00023; A61B 2018/00029; A61B 2018/00035; A61B 2018/0231; A61B 2018/025; A61B 2018/0256; A61B 18/04; A61B 18/08
See application file for complete search history.

(56) References Cited

U.S. PATENT DOCUMENTS

| 300,155 A | 6/1884 | Starr |
| 770,368 A | 9/1904 | Heath |

(Continued)

FOREIGN PATENT DOCUMENTS

| EP | 0033958 | 8/1981 |
| EP | 0 130 671 | 9/1985 |

(Continued)

OTHER PUBLICATIONS

Center for Research in Scientific Computation. *A Domain Wall Theory for Ferroelectric Hysteresis*, Jan. 1999.
(Continued)

*Primary Examiner* — Robert N Wieland
(74) *Attorney, Agent, or Firm* — Snow Christensen & Martineau; Randall B. Bateman; Sarah W. Matthews

(57) ABSTRACT

A cooling system for a surgical handpiece may provide fluid flow to the surgical tip and to the internal electronic components to prevent temperatures that may damage or make the patient or surgeon uncomfortable. Tip directed gas further controls the tip-tissue interface by displacing blood or serum from the incision point, increasing precision and diminishing coagulum build-up. In the alternative, cooling fluid may be used to quench tissue being treated.

21 Claims, 46 Drawing Sheets

(51) Int. Cl.

| | | |
|---|---|---|
| *A61B 18/14* | (2006.01) | |
| *A61B 17/32* | (2006.01) | |
| *A61B 18/00* | (2006.01) | |
| *A61B 19/02* | (2006.01) | |
| *A61B 17/00* | (2006.01) | |

(52) U.S. Cl.
CPC ... *A61B19/0256* (2013.01); *A61B 2017/00473* (2013.01); *A61B 2018/00011* (2013.01); *A61B 2018/00023* (2013.01); *A61B 2018/00035* (2013.01); *A61B 2018/0063* (2013.01); *A61B 2018/00577* (2013.01); *A61B 2018/00601* (2013.01); *A61B 2217/007* (2013.01)

(56) References Cited

U.S. PATENT DOCUMENTS

| | | | |
|---|---|---|---|
| 1,104,053 A | 7/1914 | Lea | |
| 1,280,052 A | 9/1918 | Lidberg | |
| 1,335,987 A | 4/1920 | Reid | |
| 1,366,231 A | 1/1921 | Winter et al. | |
| 1,401,104 A | 12/1921 | Kruesheld | |
| 1,794,296 A | 2/1931 | Hyams | |
| 2,027,854 A | 1/1936 | Breth et al. | |
| 2,050,904 A | 8/1936 | Trice | |
| 2,120,598 A | 6/1938 | Beuoy | |
| 2,250,602 A | 7/1941 | Pierce | |
| 2,278,633 A | 4/1942 | Bagnall | |
| 2,375,154 A | 5/1945 | Volterra | |
| 2,412,977 A | 12/1946 | Eskin | |
| 2,501,499 A | 3/1950 | Crowley | |
| 2,670,425 A | 12/1954 | Stone | |
| 2,735,797 A | 2/1956 | Schjeldahl | |
| 2,782,290 A | 2/1957 | Lannan et al. | |
| 2,831,242 A | 4/1958 | Kieffer et al. | |
| 2,846,560 A | 8/1958 | Jacoby et al. | |
| 2,863,036 A | 12/1958 | Mitchell et al. | |
| 2,947,345 A | 8/1960 | Schjeldahl | |
| 2,960,592 A | 11/1960 | Pierce | |
| 3,084,242 A | 4/1963 | Vogler et al. | |
| 3,213,259 A | 10/1965 | Bennet et al. | |
| 3,350,544 A | 10/1967 | Lennox | |
| 3,352,011 A | 11/1967 | Alexander et al. | |
| 3,400,252 A | 9/1968 | Hayakawa | |
| 3,404,202 A | 10/1968 | Carlson et al. | |
| 3,413,442 A | 11/1968 | Buiting et al. | |
| 3,414,705 A | 12/1968 | Marcoux | |
| 3,434,476 A | 3/1969 | Shaw et al. | |
| 3,501,619 A | 3/1970 | Buiting et al. | |
| 3,515,837 A | 6/1970 | Ando | |
| 3,520,043 A | 7/1970 | Darling | |
| 3,556,953 A | 1/1971 | Schulz | |
| 3,768,482 A | 10/1973 | Shaw | |
| 3,825,004 A | 7/1974 | Durden, III | |
| 3,826,263 A | 7/1974 | Cage et al. | |
| 3,834,392 A | 9/1974 | Lampman et al. | |
| 3,978,312 A | 8/1976 | Barton et al. | |
| RE29,088 E | 12/1976 | Shaw | |
| 4,089,336 A | 5/1978 | Cage et al. | |
| 4,091,813 A | 5/1978 | Shaw et al. | |
| RE30,190 E | 1/1980 | Shaw | |
| 4,185,632 A | 1/1980 | Shaw | |
| 4,196,734 A | 4/1980 | Harris | |
| 4,198,957 A | 4/1980 | Cage et al. | |
| 4,206,759 A | 6/1980 | Shaw | |
| 4,207,896 A | 6/1980 | Shaw | |
| 4,209,017 A | 6/1980 | Shaw | |
| 4,256,945 A | 3/1981 | Carter et al. | |
| 4,359,052 A | 11/1982 | Staub | |
| 4,364,390 A | 12/1982 | Shaw | |
| 4,371,861 A | 2/1983 | Abdelrahman et al. | |
| 4,374,517 A | 2/1983 | Hagiwara | |
| RE31,723 E | 11/1984 | Shaw | |
| 4,481,057 A | 11/1984 | Beard | |
| 4,485,810 A | 12/1984 | Beard | |
| 4,492,231 A | 1/1985 | Auth | |
| 4,493,320 A | 1/1985 | Treat | |
| 4,523,084 A | 6/1985 | Tamura et al. | |
| 4,549,073 A | 10/1985 | Tamura et al. | |
| 4,600,018 A | 7/1986 | James et al. | |
| 4,622,966 A | 11/1986 | Beard | |
| 4,701,587 A | 10/1987 | Carter et al. | |
| 4,752,673 A | 6/1988 | Krumme | |
| 4,807,620 A | 2/1989 | Strul | |
| 4,839,501 A | 6/1989 | Cowell | |
| 4,848,337 A | 7/1989 | Shaw et al. | |
| 4,877,944 A | 10/1989 | Cowell et al. | |
| 4,914,267 A | 4/1990 | Derbyshire | |
| 4,915,100 A | 4/1990 | Green | |
| 4,927,413 A | 5/1990 | Hess | |
| 4,938,761 A | 7/1990 | Ensslin | |
| 5,003,991 A | 4/1991 | Takayama et al. | |
| 5,047,025 A | 9/1991 | Taylor et al. | |
| 5,053,595 A | 10/1991 | Derbyshire | |
| 5,057,106 A | 10/1991 | Kasevich et al. | |
| 5,071,419 A | 12/1991 | Rydell et al. | |
| 5,087,256 A | 2/1992 | Taylor et al. | |
| 5,087,804 A | 2/1992 | McGaffigan | |
| 5,098,429 A | 3/1992 | Sterzer | |
| 5,107,095 A | 4/1992 | Derbyshire | |
| 5,182,427 A | 1/1993 | McGaffigan | |
| 5,189,271 A | 2/1993 | Derbyshire | |
| 5,197,649 A | 3/1993 | Bessler et al. | |
| 5,203,782 A | 4/1993 | Gudov et al. | |
| 5,209,725 A | 5/1993 | Roth | |
| 5,211,646 A | 5/1993 | Alperovich et al. | |
| 5,217,460 A | 6/1993 | Knoepfler | |
| 5,300,068 A | 4/1994 | Rosar et al. | |
| 5,300,750 A | 4/1994 | Carter, Jr. et al. | |
| 5,308,311 A | 5/1994 | Eggers et al. | |
| 5,318,564 A | 6/1994 | Eggers | |
| 5,364,392 A | 11/1994 | Warner et al. | |
| 5,370,675 A | 12/1994 | Edwards et al. | |
| 5,376,094 A | 12/1994 | Kline | |
| 5,382,247 A | 1/1995 | Cimino et al. | |
| 5,400,267 A | 3/1995 | Denen et al. | |
| 5,411,508 A | 5/1995 | Bessler et al. | |
| 5,423,808 A | 6/1995 | Edwards et al. | |
| 5,425,731 A | 6/1995 | Daniel et al. | |
| 5,445,635 A | 8/1995 | Denen et al. | |
| 5,472,443 A | 12/1995 | Cordis et al. | |
| 5,475,203 A | 12/1995 | McGaffigan | |
| 5,480,397 A | 1/1996 | Eggers | |
| 5,480,398 A | 1/1996 | Eggers | |
| 5,496,312 A | 3/1996 | Klicek | |
| 5,496,314 A | 3/1996 | Eggers | |
| 5,507,743 A | 4/1996 | Edwards et al. | |
| 5,540,679 A | 7/1996 | Fram et al. | |
| 5,540,681 A | 7/1996 | Strul et al. | |
| 5,542,916 A | 8/1996 | Hirsch et al. | |
| 5,571,153 A | 11/1996 | Wallsten | |
| 5,573,533 A | 11/1996 | Strul | |
| 5,593,406 A | 1/1997 | Eggers et al. | |
| 5,595,565 A | 1/1997 | Treat et al. | |
| 5,611,798 A | 3/1997 | Eggers | |
| 5,628,771 A | 5/1997 | Mizukawa et al. | |
| 5,674,219 A | 10/1997 | Monson et al. | |
| 5,707,402 A | 1/1998 | Heim | |
| 5,807,392 A | 9/1998 | Eggers | |
| 5,827,269 A | 10/1998 | Saadat | |
| 5,836,874 A | 11/1998 | Swanson et al. | |
| 5,836,943 A | 11/1998 | Miller, III | |
| 5,843,019 A | 12/1998 | Eggers et al. | |
| 5,911,719 A | 6/1999 | Eggers | |
| 5,964,759 A | 10/1999 | Yamanashi et al. | |
| 6,004,316 A | 12/1999 | Laufer | |
| 6,006,755 A | 12/1999 | Edwards | |
| 6,015,415 A | 1/2000 | Avellanet | |
| 6,035,238 A | 3/2000 | Ingle et al. | |
| 6,038,017 A | 3/2000 | Pinsukanjana et al. | |
| 6,066,138 A | 5/2000 | Sheffer et al. | |
| 6,161,048 A | 12/2000 | Sluijter et al. | |
| 6,190,382 B1 | 2/2001 | Ormsby et al. | |
| 6,228,084 B1 | 5/2001 | Kirwan, Jr. | |

(56) References Cited

U.S. PATENT DOCUMENTS

| | | |
|---|---|---|
| 6,241,723 B1 | 6/2001 | Heim et al. |
| 6,287,305 B1 | 9/2001 | Heim et al. |
| 6,290,697 B1 | 9/2001 | Tu et al. |
| 6,350,262 B1 * | 2/2002 | Ashley .................... 606/32 |
| 6,358,273 B1 | 3/2002 | Strul et al. |
| 6,533,781 B2 | 3/2003 | Heim et al. |
| 6,602,252 B2 | 8/2003 | Mollenauer |
| 6,604,003 B2 | 8/2003 | Fredricks et al. |
| 6,626,901 B1 | 9/2003 | Treat et al. |
| 6,632,182 B1 | 10/2003 | Treat |
| 6,692,489 B1 | 2/2004 | Heim et al. |
| 6,726,683 B1 | 4/2004 | Shaw |
| 6,821,273 B2 | 11/2004 | Mollenauer |
| 6,860,880 B2 | 3/2005 | Treat et al. |
| 6,908,463 B2 | 6/2005 | Treat et al. |
| 6,911,026 B1 | 6/2005 | Hall et al. |
| 6,912,911 B2 | 7/2005 | Oh et al. |
| 6,980,862 B2 | 12/2005 | Fredricks et al. |
| 6,980,865 B1 | 12/2005 | Wang et al. |
| 7,011,656 B2 | 3/2006 | McGaffigan et al. |
| 7,083,613 B2 | 8/2006 | Treat |
| 7,122,030 B2 | 10/2006 | Flores et al. |
| 7,164,968 B2 | 1/2007 | Treat et al. |
| 7,175,621 B2 | 2/2007 | Heim et al. |
| 7,211,079 B2 | 5/2007 | Treat |
| 7,211,080 B2 | 5/2007 | Treat et al. |
| 7,235,073 B2 | 6/2007 | Levine et al. |
| 7,300,452 B2 | 11/2007 | Gleich |
| 7,317,275 B2 | 1/2008 | Treat |
| 7,326,202 B2 | 2/2008 | McGaffigan |
| 7,329,255 B2 | 2/2008 | McGaffigan |
| 7,377,919 B2 | 5/2008 | Heim et al. |
| 7,396,356 B2 | 7/2008 | Mollenauer |
| 7,473,250 B2 | 1/2009 | Makin et al. |
| 7,494,492 B2 | 2/2009 | Da Silva et al. |
| 7,528,663 B2 | 5/2009 | Naletov et al. |
| 7,533,719 B2 | 5/2009 | Hinson |
| 7,540,324 B2 | 6/2009 | de Rouffignac |
| 7,549,470 B2 | 6/2009 | Vinegar |
| 7,556,095 B2 | 7/2009 | Vinegar |
| 7,556,096 B2 | 7/2009 | Vinegar |
| 7,559,367 B2 | 7/2009 | Vinegar |
| 7,559,368 B2 | 7/2009 | Vinegar |
| 7,562,706 B2 | 7/2009 | Li et al. |
| 7,562,707 B2 | 7/2009 | Miller |
| 7,578,815 B2 | 8/2009 | Howell |
| 7,581,589 B2 | 9/2009 | Roes et al. |
| 7,584,789 B2 | 9/2009 | Mo et al. |
| 7,588,565 B2 | 9/2009 | Marchitto et al. |
| 7,588,566 B2 | 9/2009 | Treat et al. |
| 7,591,310 B2 | 9/2009 | Minderhoud |
| 7,597,147 B2 | 10/2009 | Vitek |
| 7,604,052 B2 | 10/2009 | Roes |
| 7,610,962 B2 | 11/2009 | Fowler |
| 7,613,523 B2 | 11/2009 | Eggers et al. |
| 7,631,689 B2 | 12/2009 | Vinegar |
| 7,631,690 B2 | 12/2009 | Vinegar |
| 7,632,295 B2 | 12/2009 | Flores |
| 7,635,023 B2 | 12/2009 | Goldberg |
| 7,635,024 B2 | 12/2009 | Karanikas |
| 7,635,025 B2 | 12/2009 | Vinegar |
| 7,702,397 B2 | 4/2010 | Fredricks et al. |
| 7,871,406 B2 | 1/2011 | Nields et al. |
| 7,922,713 B2 | 4/2011 | Geisel |
| 7,931,649 B2 | 4/2011 | Couture et al. |
| 7,938,779 B2 | 5/2011 | Sakurai et al. |
| 7,951,149 B2 | 5/2011 | Carlton |
| 8,100,896 B2 | 1/2012 | Rodhajsky |
| 8,292,879 B2 | 10/2012 | Manwaring et al. |
| 8,377,052 B2 | 2/2013 | Manwaring et al. |
| 8,419,724 B2 | 4/2013 | Manwaring et al. |
| 8,460,870 B2 | 6/2013 | Zocchi |
| 8,506,561 B2 | 8/2013 | Manwaring et al. |
| 2001/0014804 A1 | 8/2001 | Goble et al. |
| 2002/0019627 A1 | 2/2002 | Maguire et al. |
| 2002/0019644 A1 | 2/2002 | Hastings et al. |
| 2002/0026188 A1 | 2/2002 | Balbierz et al. |
| 2002/0029037 A1 | 3/2002 | Kim |
| 2002/0029062 A1 | 3/2002 | Satake |
| 2002/0068931 A1 | 6/2002 | Wong et al. |
| 2002/0087156 A1 | 7/2002 | Maguire et al. |
| 2002/0120261 A1 | 8/2002 | Balbierz et al. |
| 2002/0133148 A1 | 9/2002 | Daniel et al. |
| 2002/0173787 A1 | 11/2002 | Buysse et al. |
| 2003/0004507 A1 | 1/2003 | Francischelli et al. |
| 2003/0055417 A1 | 3/2003 | Truckai et al. |
| 2003/0055424 A1 | 3/2003 | Ciarrocca |
| 2003/0060818 A1 | 3/2003 | Kannenberg et al. |
| 2003/0073987 A1 | 4/2003 | Sakurai et al. |
| 2003/0073989 A1 | 4/2003 | Hoey et al. |
| 2003/0109871 A1 | 6/2003 | Johnson et al. |
| 2003/0144660 A1 | 7/2003 | Mollenauer |
| 2003/0171747 A1 | 9/2003 | Kanehira et al. |
| 2003/0176873 A1 | 9/2003 | Chernenko et al. |
| 2003/0195499 A1 | 10/2003 | Prakash et al. |
| 2003/0199755 A1 | 10/2003 | Halperin |
| 2004/0006335 A1 | 1/2004 | Garrison |
| 2004/0030330 A1 | 2/2004 | Brassell et al. |
| 2004/0034349 A1 | 2/2004 | Kirwan, Jr. et al. |
| 2004/0049185 A1 | 3/2004 | Latterell et al. |
| 2004/0059345 A1 | 3/2004 | Nakao et al. |
| 2004/0073256 A1 | 4/2004 | Marchitto |
| 2004/0167506 A1 | 8/2004 | Chen |
| 2004/0176756 A1 | 9/2004 | McGaffigan |
| 2004/0187875 A1 | 9/2004 | He et al. |
| 2004/0243120 A1 | 12/2004 | Orszulak et al. |
| 2005/0021016 A1 | 1/2005 | Malecki et al. |
| 2005/0033338 A1 | 2/2005 | Ferree |
| 2005/0072827 A1 | 4/2005 | Mollenauer |
| 2005/0107776 A1 | 5/2005 | McGaffigan et al. |
| 2005/0113824 A1 | 5/2005 | Sartor et al. |
| 2005/0197661 A1 | 9/2005 | Carrison et al. |
| 2005/0245919 A1 | 11/2005 | Van der Welde |
| 2005/0273111 A1 | 12/2005 | Ferree et al. |
| 2005/0283067 A1 | 12/2005 | Sobe |
| 2005/0283149 A1 | 12/2005 | Thorne et al. |
| 2005/0288659 A1 | 12/2005 | Kimura et al. |
| 2006/0127706 A1 | 6/2006 | Goebel et al. |
| 2006/0142824 A1 | 6/2006 | Zikorus et al. |
| 2006/0161149 A1 | 7/2006 | Privitera et al. |
| 2006/0167450 A1 | 7/2006 | Johnson et al. |
| 2006/0212030 A1 | 9/2006 | McGaffigan |
| 2006/0212031 A1 | 9/2006 | McGaffigan et al. |
| 2006/0217700 A1 | 9/2006 | Garito et al. |
| 2006/0217706 A1 | 9/2006 | Lau et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0271037 A1 | 11/2006 | Maroney et al. |
| 2007/0005054 A1 | 1/2007 | Heim et al. |
| 2007/0005055 A1 | 1/2007 | Heim et al. |
| 2007/0005056 A1 | 1/2007 | Heim et al. |
| 2007/0005057 A1 | 1/2007 | Heim et al. |
| 2007/0005058 A1 | 1/2007 | Heim et al. |
| 2007/0005059 A1 | 1/2007 | Heim et al. |
| 2007/0005060 A1 | 1/2007 | Heim et al. |
| 2007/0016181 A1 | 1/2007 | van der Weide et al. |
| 2007/0060920 A1 | 3/2007 | Weitzner |
| 2007/0073282 A1 | 3/2007 | McGaffigan et al. |
| 2007/0100336 A1 | 5/2007 | McFarlin et al. |
| 2007/0106294 A1 | 5/2007 | Nesbitt |
| 2007/0127897 A1 | 6/2007 | John et al. |
| 2007/0131428 A1 | 6/2007 | Boestert |
| 2007/0173811 A1 | 7/2007 | Couture et al. |
| 2007/0208339 A1 | 9/2007 | Arts et al. |
| 2007/0239151 A1 | 10/2007 | Atalar et al. |
| 2007/0270924 A1 | 11/2007 | McCann et al. |
| 2008/0017380 A1 | 1/2008 | Vinegar |
| 2008/0033419 A1 | 2/2008 | Nields et al. |
| 2008/0035346 A1 | 2/2008 | Nair et al. |
| 2008/0035347 A1 | 2/2008 | Brady |
| 2008/0035705 A1 | 2/2008 | Menotti |
| 2008/0038144 A1 | 2/2008 | Maziasz |
| 2008/0077129 A1 | 3/2008 | Van Wyk |

(56) References Cited

U.S. PATENT DOCUMENTS

| | | |
|---|---|---|
| 2008/0119841 A1 | 5/2008 | Geisel |
| 2008/0128134 A1 | 6/2008 | Mudunuri et al. |
| 2008/0135253 A1 | 6/2008 | Vinegar |
| 2008/0135254 A1 | 6/2008 | Vinegar |
| 2008/0142216 A1 | 6/2008 | Vinegar |
| 2008/0142217 A1 | 6/2008 | Pieterson |
| 2008/0161800 A1 | 7/2008 | Wang et al. |
| 2008/0173444 A1 | 7/2008 | Stone et al. |
| 2008/0174115 A1 | 7/2008 | Lambirth |
| 2008/0185147 A1 | 8/2008 | Vinegar |
| 2008/0217003 A1 | 9/2008 | Kuhlman |
| 2008/0217016 A1 | 9/2008 | Stegemeier |
| 2008/0228135 A1 | 9/2008 | Snoderly |
| 2008/0236831 A1 | 10/2008 | Hsu |
| 2008/0277113 A1 | 11/2008 | Stegemeier |
| 2008/0281310 A1 | 11/2008 | Dunning et al. |
| 2008/0281315 A1 | 11/2008 | Gines |
| 2008/0319438 A1* | 12/2008 | DeCarlo .................. 606/41 |
| 2009/0014180 A1 | 1/2009 | Stegemeier |
| 2009/0014181 A1 | 1/2009 | Vinegar |
| 2009/0093811 A1 | 4/2009 | Koblish et al. |
| 2009/0112200 A1 | 4/2009 | Eggers |
| 2009/0118729 A1 | 5/2009 | Auth et al. |
| 2009/0118730 A1 | 5/2009 | Mollenauer |
| 2009/0198224 A1 | 8/2009 | McGaffigan |
| 2009/0248002 A1 | 10/2009 | Takashino et al. |
| 2009/0292347 A1 | 11/2009 | Asmus et al. |
| 2009/0306644 A1 | 12/2009 | Mayse et al. |
| 2009/0312753 A1* | 12/2009 | Shadduck .................. 606/14 |
| 2010/0004650 A1 | 1/2010 | Ormsby et al. |
| 2010/0082022 A1 | 4/2010 | Haley et al. |
| 2010/0152725 A1 | 6/2010 | Pearson et al. |
| 2010/0198216 A1 | 8/2010 | Palanker |
| 2010/0228244 A1 | 9/2010 | Hancock et al. |
| 2010/0268205 A1 | 10/2010 | Manwaring et al. |
| 2010/0268206 A1 | 10/2010 | Manwaring et al. |
| 2010/0268207 A1 | 10/2010 | Manwaring et al. |
| 2010/0268208 A1 | 10/2010 | Manwaring et al. |
| 2010/0268209 A1 | 10/2010 | Manwaring et al. |
| 2010/0268210 A1 | 10/2010 | Manwaring et al. |
| 2010/0268211 A1 | 10/2010 | Manwaring et al. |
| 2010/0268212 A1 | 10/2010 | Manwaring et al. |
| 2010/0268213 A1 | 10/2010 | Manwaring et al. |
| 2010/0268214 A1 | 10/2010 | Manwaring et al. |
| 2010/0268215 A1 | 10/2010 | Manwaring et al. |
| 2010/0268216 A1 | 10/2010 | Manwaring et al. |
| 2010/0268218 A1 | 10/2010 | Ormsby et al. |
| 2011/0004204 A1* | 1/2011 | Dodde et al. ................ 606/21 |
| 2011/0054456 A1 | 3/2011 | Thompson et al. |
| 2011/0152857 A1 | 6/2011 | Ingle |
| 2012/0071712 A1 | 3/2012 | Manwaring et al. |
| 2012/0226270 A1 | 9/2012 | Manwaring et al. |
| 2012/0259323 A1 | 10/2012 | Manwaring et al. |
| 2012/0296326 A1 | 11/2012 | Manwaring et al. |
| 2012/0330295 A1 | 12/2012 | Manwaring et al. |
| 2013/0006240 A1 | 1/2013 | McNally et al. |
| 2013/0012934 A1 | 1/2013 | Manwaring et al. |
| 2013/0023866 A1 | 1/2013 | Stringham et al. |
| 2013/0218152 A1 | 8/2013 | Manwaring et al. |

FOREIGN PATENT DOCUMENTS

| | | |
|---|---|---|
| EP | 2036512 | 3/2009 |
| EP | 2070486 | 6/2009 |
| GB | 2 022 974 | 12/1978 |
| GB | 1 546 624 | 5/1979 |
| JP | 03051179 | 8/1996 |
| JP | 2558584 | 9/1996 |
| RU | 2 072 118 | 1/1997 |
| WO | WO-82/00746 | 3/1982 |
| WO | WO 92/17121 | 10/1992 |
| WO | WO-93/21839 | 11/1993 |
| WO | WO-96/26677 | 11/1996 |
| WO | WO 9937227 A1 | 7/1999 |
| WO | WO-01/06943 | 2/2001 |
| WO | WO-2004/14217 | 2/2004 |
| WO | WO-2004/076146 | 9/2004 |
| WO | WO-2006/017517 | 2/2006 |
| WO | WO-2006/029649 | 3/2006 |
| WO | WO 2007080578 A2 | 7/2007 |
| WO | WO-2008/060668 | 5/2008 |

OTHER PUBLICATIONS

Metcal Soldering Iron Catalog—2006.

URSI EMTS 2004, pp. 489-491, *Electromagnetic Probes for Living Tissue Cauterization*.

"High Temp Metals." NI2001201 Technical Data. High Temp Metals, Inc., n.d. Web. Jul. 13, 2012. <http://www.hightempmetals.com/techdatafnitempNi200data.php.

International Preliminary Report on Patentability from related PCT Patent Application No. PCT/US2010/031114, Nov. 1, 2011.

International Preliminary Report on Patentability from related PCT Patent Application No. PCT/US2010/031114, Jan. 21, 2011.

International Preliminary Report on Patentability from related PCT Patent Application No. PCT/US2011/050417, Apr. 12, 2012.

International Preliminary Report on Patentability from related PCT Patent Application No. PCT/US2012/032656, Oct. 23, 2012.

International Preliminary Report on Patentability from related PCT Patent Application No. PCT/US2012/032659, Nov. 23, 2012.

International Preliminary Report on Patentability from related PCT Patent Application No. PCT/US2012/038005, Nov. 23, 2012.

International Preliminary Report on Patentability from related PCT Patent Application No. PCT/US2012/055229, Feb. 1, 2013.

Written Opinion of the International Preliminary Examining Authority from related PCT Patent Application No. PCT/US2011/050417, Feb. 6, 2013.

International Preliminary Report on Patentability from related PCT Patent Application No. PCT/US2012/068027, Feb. 25, 2013.

Visioli, Antonio. Practice PID Control: London: Springer-Verlag, 2006. 1-18. Print.

International Search Report and Written Opinion from related PCT Application US2012/032661, Aug. 19, 2013.

International Search Report and Written Opinion from related PCT Application US2012/032659, Oct. 8, 2013.

International Search Report and Written Opinion from related PCT Application US2012/032565, Oct. 8, 2013.

International Preliminary Report on Patentability from related PCT Application US2012/038005, Nov. 19, 2013.

International Preliminary Report on Patentability from related PCT Application US2012/068027, Jun. 19, 2014.

Translation of Office Action from related Japanese Patent Application No. 2012-506188, PCT US2010-031114.

European Search Report from European Application No. 12865504. 0-1652, dated Nov. 28, 2014.

\* cited by examiner

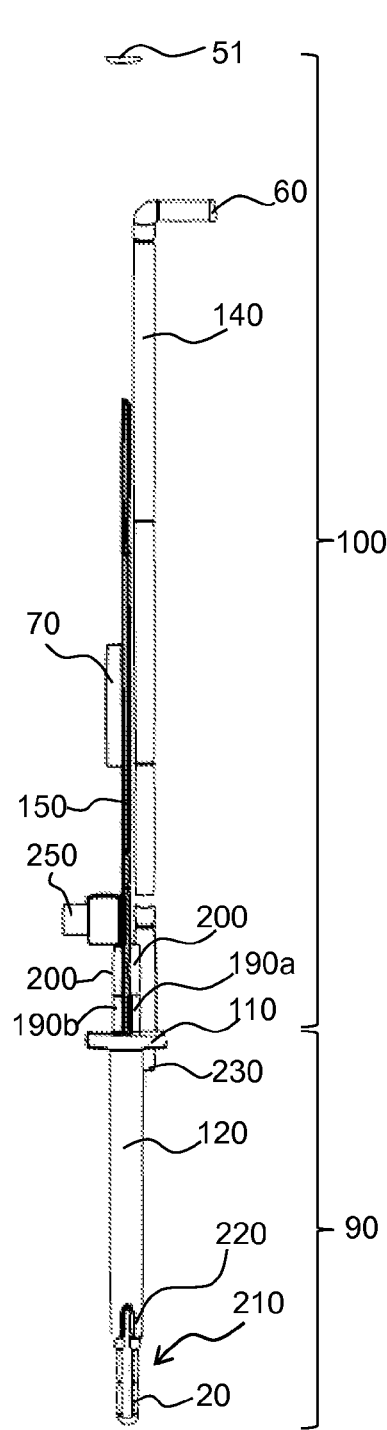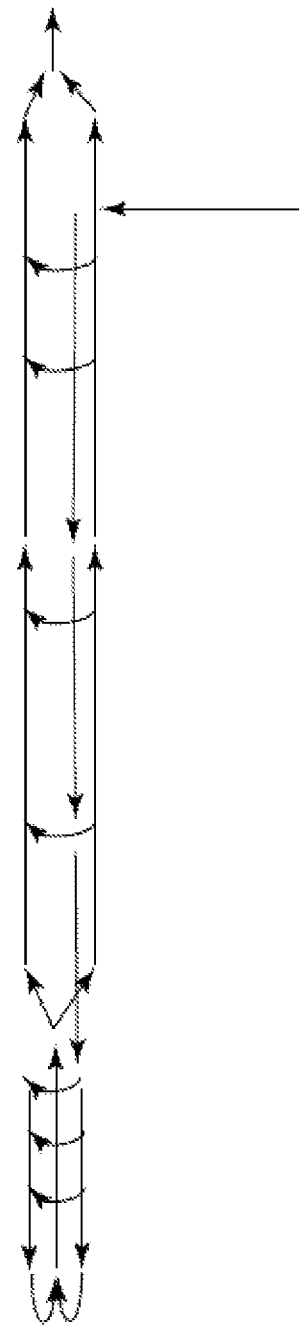
FIG. 14A  FIG. 14B  FIG. 14C

SYSTEM AND METHOD FOR COOLING OF A HEATED SURGICAL INSTRUMENT AND/OR SURGICAL SITE AND TREATING TISSUE

PRIORITY

The present application claims the benefit of U.S. Provisional Patent Application Ser. No. 61/473,725, filed Apr. 8, 2011 and U.S. Provisional Patent Application Ser. No. 61/505,059, filed Jul. 6, 2011, which are incorporated herein by reference in their entirety.

THE FIELD OF THE INVENTION

The present invention relates to surgical instruments. More specifically, the present invention relates to a system and method for cooling a heated surgical instrument and/or the surgical field in which a heated surgical instrument is being used, or otherwise treating tissue.

BACKGROUND

It is becoming more common to use heated surgical instruments, such as electrosurgical devices, during surgery because electrosurgical devices may provide benefits over traditional surgical devices. For example, some electrosurgical instruments have the ability to make precise incisions in tissue with limited blood loss. Because of their advantages, electrosurgical devices are used in dermatological, gynecological, cardiac, plastic, ocular, spine, ENT, maxillofacial, orthopedic, urological, neurological and general surgical procedures as well as certain dental procedures, just to name a few.

Electrosurgical devices may be used for cutting, repairing and/or removing tissue or other materials from a patient. To perform each of these procedures the electrosurgical device must heat the tissue or other material to a desired temperature. For example, for vascular endothelial welding a surgeon may use an electrosurgical device that heats to temperatures of about 58-62 degrees Centigrade, whereas, to make an incision a surgeon may have to use an electrosurgical device that heats to temperatures of about 200-400 degrees Centigrade or higher. If a surgeon is not able to control the temperature of the electrosurgical device during use, or the device cools too slowly after the device is no longer being activated, then undesired results may occur which may lead to an adverse outcome for the patient.

As surgical instruments become more advanced, they often have increased power demands which may cause heat to build-up in a surgical instrument. While it may be desirable to have a high temperature at a precise surgical site, such as the tip of an electrosurgical instrument, high temperatures may be undesirable elsewhere. For example, if the temperature of structures adjacent a tip of an electrosurgical instrument becomes too hot, those structures may damage and/or destroy tissue.

A surgical instrument may also dissipate heat into the surgical handpiece. High temperatures of a surgical handpiece may decrease the effectiveness of, or cause pain or discomfort to the surgeon. High heat of a handpiece may limit the acceptance of the instrument, or reduce the amount of time the surgical instrument may be put in use. Furthermore, undesirable heating may reduce the effectiveness of onboard electronics.

The undesired heating of the surgical instrument may be caused by heating of a surgical structure, heating of handpiece electronics and/or heat otherwise caused by operation of the surgical instrument. The heat may even become more critical because many surgical instruments are small with little room to effectively dissipate heat into the air.

Moreover, while it is desirable to have a surgical instrument that achieves adequate temperature for sealing, cutting, etc., it is often desirable to minimize the damage caused by the heat to anything but the precise location of the tissue being treated. Thus, while it may be desirable to maintain an electrosurgical device at a high temperature for a given procedure, tissue in the surgical field adjacent to the surgical site may be unnecessarily damaged by the exposure to the high temperature. Again this may lead to undesired results and an adverse outcome for the patient.

Therefore it would be desirable to cool a surgical instrument, such that adjacent structures, the handpiece and the electronics remain sufficiently cool to not adversely impact the performance of the surgical instrument and/or its ease of use. Such device may result in cooling of a surgical instrument both during use and when the surgical instrument is not being thermally activated. Additionally, it would be desirable to have a surgical instrument or related structure that minimized any collateral damage to tissue(s) adjacent to the surgical site.

SUMMARY OF THE INVENTION

It is an object of the present invention to provide an improved cooling system for use with thermal surgical instruments.

In accordance with one aspect of the present invention, an actively cooled surgical handpiece or other medical instrument is provided to reduce heat associated with the handpiece or other medical instrument.

In accordance with another aspect of the invention, a cooling fluid may be passed through a surgical handpiece to carry heat away from the handpiece and thereby keep the handpiece comfortable for use. For ease of reference, the flow of a cooling fluid will be referred to herein as "coolant flow." It will be appreciated that a variety of cooling fluids may be used, e.g., liquids and gasses, in various situations. These may include, but are not limited to, air, carbon dioxide, water, saline and helium.

In accordance with another aspect of the invention, the cooling fluid is passed over or through one or more structures used to support a thermal cutting element to cool the structure.

In accordance with another aspect of the invention, coolant flow may be directed toward structures adjacent a thermal element, to the thermal element, and to the electronics of the handpiece, etc. This coolant flow may aid in the reduction of temperature at the adjacent structures, such that an accidental touching of an adjacent structure may not damage tissue. The coolant flow may also aid in reducing the cooling time of the tip and/or thermal element, providing a faster "off" time, e.g. quicker cooling, when actuation of the thermal element ceases.

According to another aspect of the invention, all or a portion of the coolant flow may be directed out of an aperture toward a thermal element. This may aid in the quick cooling of the thermal element. Furthermore, the coolant flow may aid in moving liquid, such as blood, away from the surgical site. As liquid is moved from the surgical site, this may aid in the reduction of coagulum and increase the effectiveness of the thermal element.

In accordance with yet another aspect of the invention, a cooling fluid may be directed out of the handpiece and at the tissue being cut, sealed, etc., to thereby promptly remove heat from the tissue and minimize the conduction of heat into tissue beyond the location being treated. This may include, for example, directing saline solution at tissue being subject to thermal cutting or sealing to promptly quench the tissue and minimize damage beyond the portion of the tissue in direct contact with the surgical instrument.

In accordance with yet another aspect of the invention, a surgical handpiece may have interchangeable tips having thermal elements, some or all of which are attachable to the handpiece so as to provide coolant flow to the tips, thermal elements, and/or toward tissue being thermally treated.

According to one aspect of the invention, coolant flow may be drawn through a thermal surgical tool using suction.

According to another aspect of the invention, a thermal surgical tool may include a system for removing smoke and/or other air contaminates from the surgical field. The smoke removal system may be separate and in addition to a cooling system used to cool the surgical tool.

In accordance with still another aspect of the invention, the interchangeable tips may include a cooling system independent of a cooling system for the handpiece.

In accordance with another aspect of the invention, the cooling system for the handpiece and/or the tips may use forced fluid or may rely on a gravity feed of fluid.

According to still another aspect of the present invention, the rate of fluid flow to the thermal element may be adjusted to deliver more or less fluid to the thermal element.

According to yet another aspect of the present invention, a fluid cooled heated surgical instrument may include a structure for receiving tubing from a fluid drip line located at a position other than the tip which delivers fluid to a thermal element of the heated surgical instrument and/or to the surgical field.

According to another aspect of the present invention, a fluid passing through a surgical tip may be used to blanch tissue.

These and other aspects of the present invention are realized in a cooling system for heated surgical instruments as shown and described in the following figures and related description.

BRIEF DESCRIPTION OF THE DRAWINGS

Various embodiments of the present invention are shown and described in reference to the numbered drawings wherein:

FIG. 14A shows a side view of internal handpiece components;

FIG. 14B shows a side view of internal handpiece components with coolant flow indications;

FIG. 14C shows a side view of representative internal handpiece coolant flow;

It will be appreciated that the drawings are illustrative of aspects of the invention and are not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Thus, elements shown in one figure may be combined with or used in place of similar elements in another figure. Similarly, not every embodiment need accomplish all advantages of the present invention. Rather, each embodiment provides some improvement in some application which may be applicable but need not include all aspects of the invention discussed herein to fall within the scope of the claims unless expressly set forth therein.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
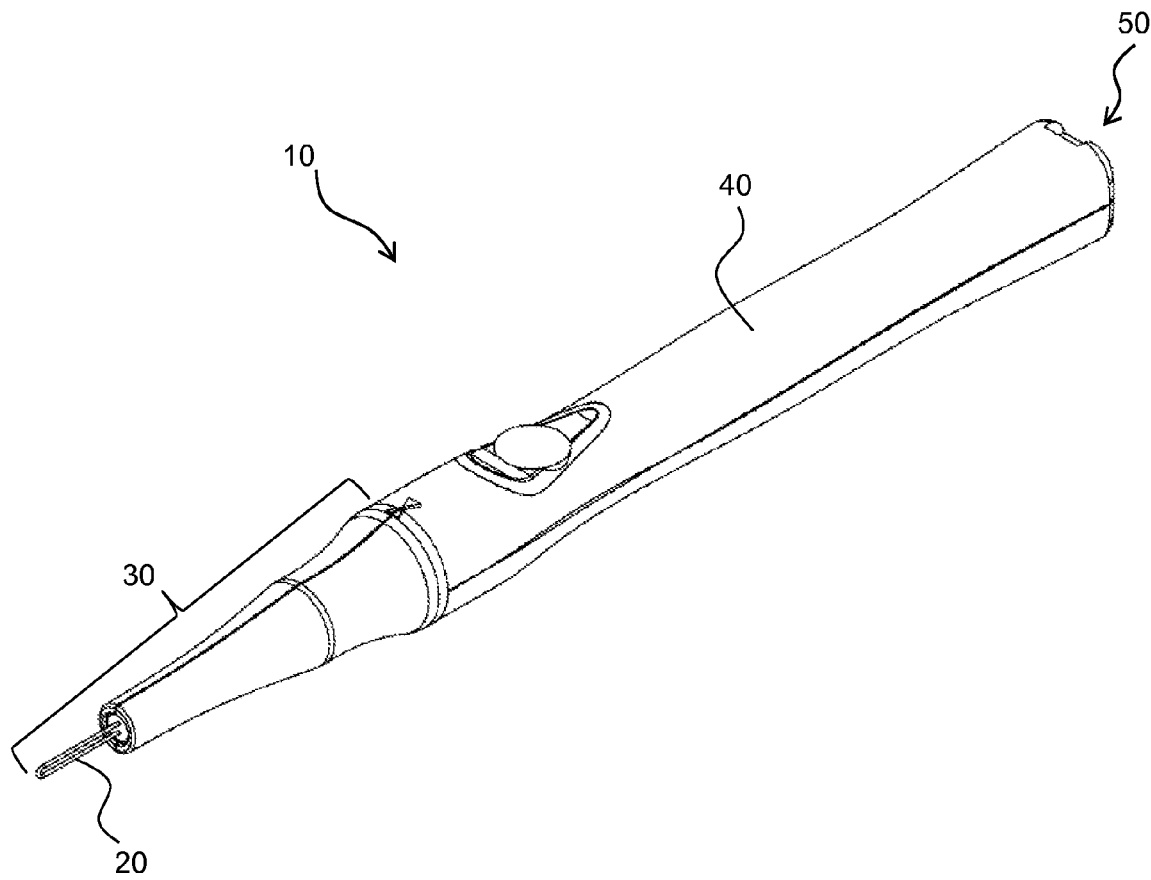
FIG. 1 shows a perspective view of a thermal surgical tool with a cooling system in accordance with the present invention.

Turning now to FIG. 1, there is shown a perspective view of a surgical handpiece, generally indicated at 10, with a cooling system. The surgical handpiece includes an active thermal element 20 which may be formed as part of a tip 30. The tip 30 may be integrally formed with, attached and/or removable from a body 40, all or a portion of which may form a handle portion.

A surgical handpiece, such as handpiece 10, may be very important to a surgeon's effectiveness in surgery. This is particularly so with electrosurgery, whether using electrical energy, mechanical energy or thermal energy to cut and/or coagulate tissue and blood vessels. The more precise containment of thermal energy to specific areas during specific periods of time may increase the safety of using a surgical handpiece 10 and also contribute to the surgeon's comfort and his or her effectiveness. A surgeon may thus desire that portions of the handpiece 10 that are expected to be hot do in fact remain hot while active, and portions that should be relatively cool should remain cool. This may be particularly true of the handle portion 40 where the surgeon holds the handpiece 10 for a prolonged period of time.

Increased thermal energy may arise at different locations in the handpiece 10 through direct or indirect sources. In some cases the thermal energy may be desirable, such as in the thermal element 20 of a ferromagnetic surgical tool converting electrical energy to heat for surgery. In other cases, increased thermal energy at a location may be a byproduct of energy dissipation, such as through conduction of heat from an active thermal element to other structures comprising the handpiece 10, heat generated by electrical components of the handpiece 10, etc. Whatever the source, if the handpiece 10 cannot remove undesired thermal energy accumulation in a controlled manner, one or more components of the handpiece 10 may get undesirably hot.

If the handpiece 10 becomes too hot, the handpiece may become dangerous to either the surgeon or the patient. For example, the tip 30 may become hot enough to damage tissue that comes into close proximity to, or in contact with, the tip if thermal energy is not effectively removed. Thus, an accidental touching of the tip 30 to tissue may injure a patient. Similarly, thermal energy may build up in the handpiece 10 over time. Overheating of the handpiece may reduce the time in which the surgical instrument may be used, cause discomfort to a surgeon using the surgical instrument, and/or even injure the surgeon.

Thus, it is desirable to control heat build-up in one or more components of a handpiece 10. In the handpiece 10 shown in FIG. 1, the active thermal element 20, such as, for example, a wire with a ferromagnetic coating may become hot to treat tissue. However it is often desirable for the remainder of the tip 30, the body 40, and/or any components located in the handpiece 10 (not shown) to remain relatively cool. In some medical applications, such as the ablation or cutting of tissue, the thermal element 20 can be driven to several hundred degrees Celsius. Thus, even a fairly small element can produce a significant thermal load which must be dissipated.

An active cooling system may help in cooling by circulating coolant, such as air (or other gas) or liquid, through the handpiece 10. The flow may pass from through a flow channel (not shown in FIG. 1) toward the tip 30 and out a rear exit 50. The active cooling system may help in cooling the tip 30, body 40, and internal components, and keep the external surfaces within a temperature range that makes it comfortable to hold the handpiece 10.

In a small handpiece 10, the handpiece may not be able to effectively dissipate heat passively, thus active cooling may be required. As power requirements rise and the desirable size of the handpiece 10 becomes smaller, there may be a greater need for active cooling in such a handpiece 10. Furthermore, active cooling may be used to remove heat from the handpiece 10 both when the thermal element 20 is being actuated and during times when power is not being delivered to the thermal element 20. By providing continuous active cooling, heat build-up in the various components may be better controlled.

Figure 2A:
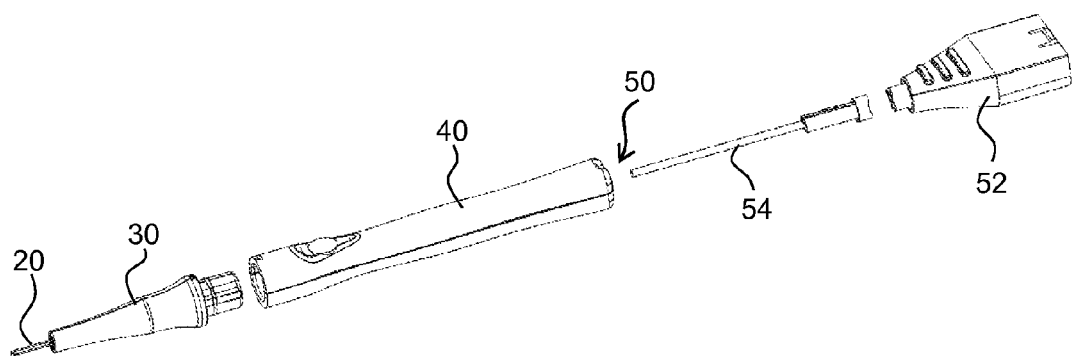
FIG. 2A shows an exploded, perspective view of a thermal surgical tool with a cooling system.

Turning now to FIG. 2A, there is shown an exploded view of the surgical handpiece 10 of FIG. 1. The handpiece 10 may include a connecting member 52 for connecting to a power supply. Electrical energy may be transferred to the handpiece 10 through an electrical lead 56, such as a coaxial cable, which may extend into the body 40 of the handpiece 10 and connect to one or more electrical components located therein. The power supply may also include a source for providing coolant flow to cool the handpiece 10. Thus, both electrical energy and coolant flow may be supplied to the handpiece 10 from a single supply, which is connected to the handpiece 10 via connecting member 52. The connecting member may be attached to the distal end 50 of the handpiece 10. Alternatively, coolant flow may be provided to the handpiece 10 from a separate source than the power supply.

Figure 2B:
FIG. 2B shows a side view of a thermal surgical tool according to principles of the present invention having a removable tip.

The handpiece 10 may also include a tip 30 having a thermal element 20 disposed thereon. As is shown in FIG. 2B, the tip 30 may be removably connected to the proximal end of the body 40. Because the tip 30 is removably connected to the body 40, a surgeon may be able to interchange various tips 30 with the body. A surgeon may use the handpiece 10 having a first tip configured to perform a specific task and then use an alternate tip to perform another task. This may be, for example, using a blade like tip for incising tissue. After the tissue is incised, then the surgeon may change to a loop to excise a tumor. Depending on the procedures, a surgeon may use multiple different tips. Additionally, if a tip 30 becomes damaged during a procedure a surgeon may simply replace the tip 30, rather than attempt to locate an alternate surgical instrument to complete the procedure.

Figure 2C:
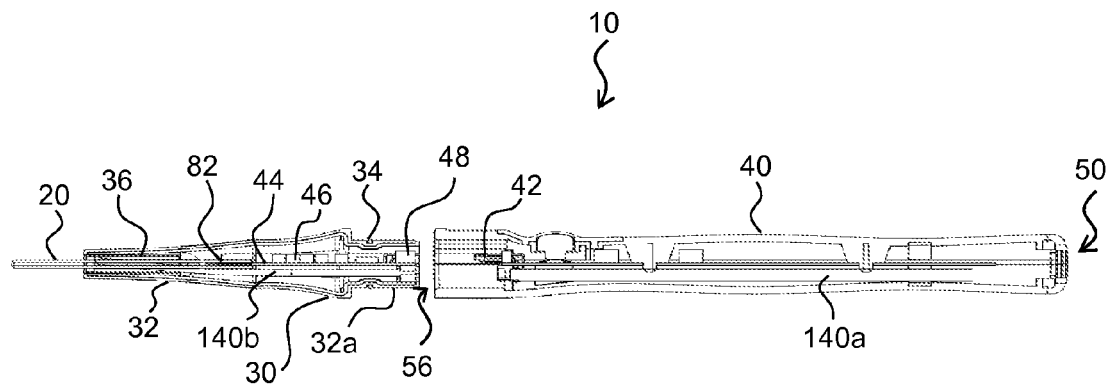
FIG. 2C show a side view of the internal components of the thermal surgical tool in FIG. 2B.

Turning now to FIG. 2C, a side view showing internal components of the surgical handpiece 10 of FIG. 2B is shown. The body 40 may include a tube 140a which extends from approximately the distal end 50 of the handpiece 10 toward a recess 54 configured to receive a tip 30. When a fluid supply is connected to the handpiece 10 at or adjacent the distal end 50, tube 140a may direct coolant flow toward the recess 54.

Tip 30 may include a housing 32, a portion of which 32a is configured to facilitate connection of the tip 30 to the body 40. For example, recess 54 may be constructed so as to have a specific configuration and the housing 32 may be keyed to fit into the recess 54 in a specific manner, i.e. the housing may have a shape that is complimentary to the shape of the recess 54. The handpiece 10 may include one or more additional alignment members 42, such as a prong, protrusion, notch, etc., to ensure that the tip 30 properly seats in the recess 54.

Figure 2D:
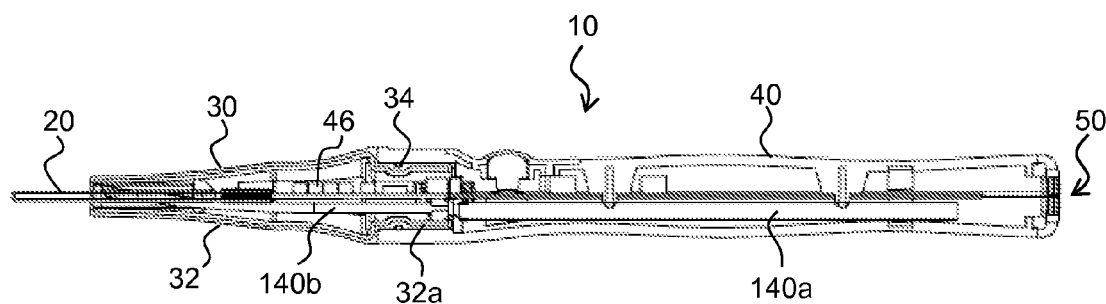
FIG. 2D shows a side, cross-sectional view of a thermal surgical tool with a removable tip connected to the body of a handpiece.

Tip 30 may also include a tube 140b. Placing the keyed housing portion 32a in the recess 54 facilitates alignment of the tubes 140a and 140b such that they are in fluid communication when the tip 30 is connected to the handpiece 10 to thereby allow coolant flow into tip 30. A side, cutaway view of the handpiece 10 in FIG. 2D shows how a sealing member 34, such as an O-ring, disposed on the tip 30 may be used to minimize coolant flow leaks that may occur when the tip 30 is connected to the body 40. Coolant flow directed into the tip 30 may actively cool electrical components 44, 46 that may be located in the tip, the tip housing 32, and according to some aspects of the invention the thermal element 20, as is explained in more detail below.

The thermal element 20 may connect to electronic components located in the tip 30. For example, the thermal element 20 may connect to a printed circuit board 44. Disposed on the thermal element 20 may be an electrically conductive material 82 which facilitates attachment of the thermal element to the printed circuit board 44. Located adjacent to the thermal element 20 may be a heat spreader or heat sink 36. The heat spreader 36 may be a sheath that extends around at least a portion of the thermal element 20 and helps dissipate the heat by convection and/or a cooling fluid. The heat spreader 36 may be comprised of aluminum, copper or other material having a high thermal conductivity and may have a geometry with an adequate surface area to dissipate heat. Thus, the high thermal conductivity, when combined with coolant flow and area can use used to maximize heat dissipation.

Figure 3:
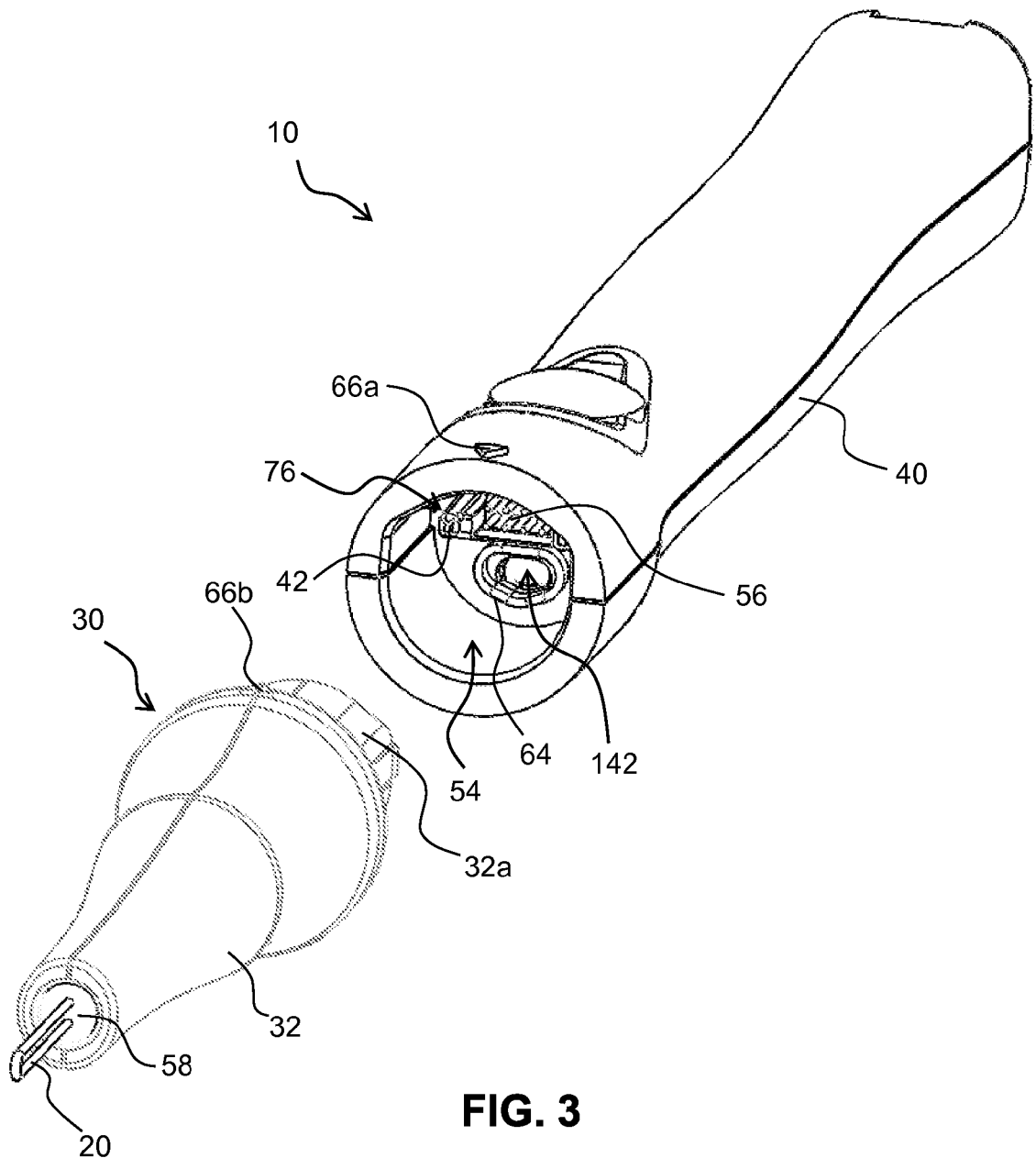
FIG. 3 shows a front, perspective view of the body of a handpiece and a removable tip, wherein the internal components of the removable tip are visible.

Turning now to FIG. 3, there is shown a perspective view of a thermal surgical tool, generally indicated at 10, according to principles of the present invention. The body 40 and the tip 30 may each have a visual aid 66a and 66b, respectively, to indicate to the user the correct orientation in which the tip 30 should be attached to the body 40. FIG. 3 also better shows the shape of the recess 54 which facilitates attachment of the tip 30 having a keyed housing portion 32a to the body 40 in the correct orientation. The body 40 may also include one or more alignment members 42 to ensure that the tip 30 and the body 40 are properly aligned when attached. Although the alignment members 42 are shown disposed on the body 40, it will be appreciated that one or more alignment members may be disposed on the tip 30.

The body 40 may include an electrical connector 56 in electrical communication with a power supply configured to mate with an electrical connector 48 disposed on the tip 30. Thus, when the tip 30 is attached to the body, electrical energy can be provided to the tip 30 to, for example, cause heating of the thermal element 20. The tip 30 may also include electrical components or processors, such as an EEPROM 69, which provide information about the tip 30 for desired functioning of the handpiece 10.

Figure 4:
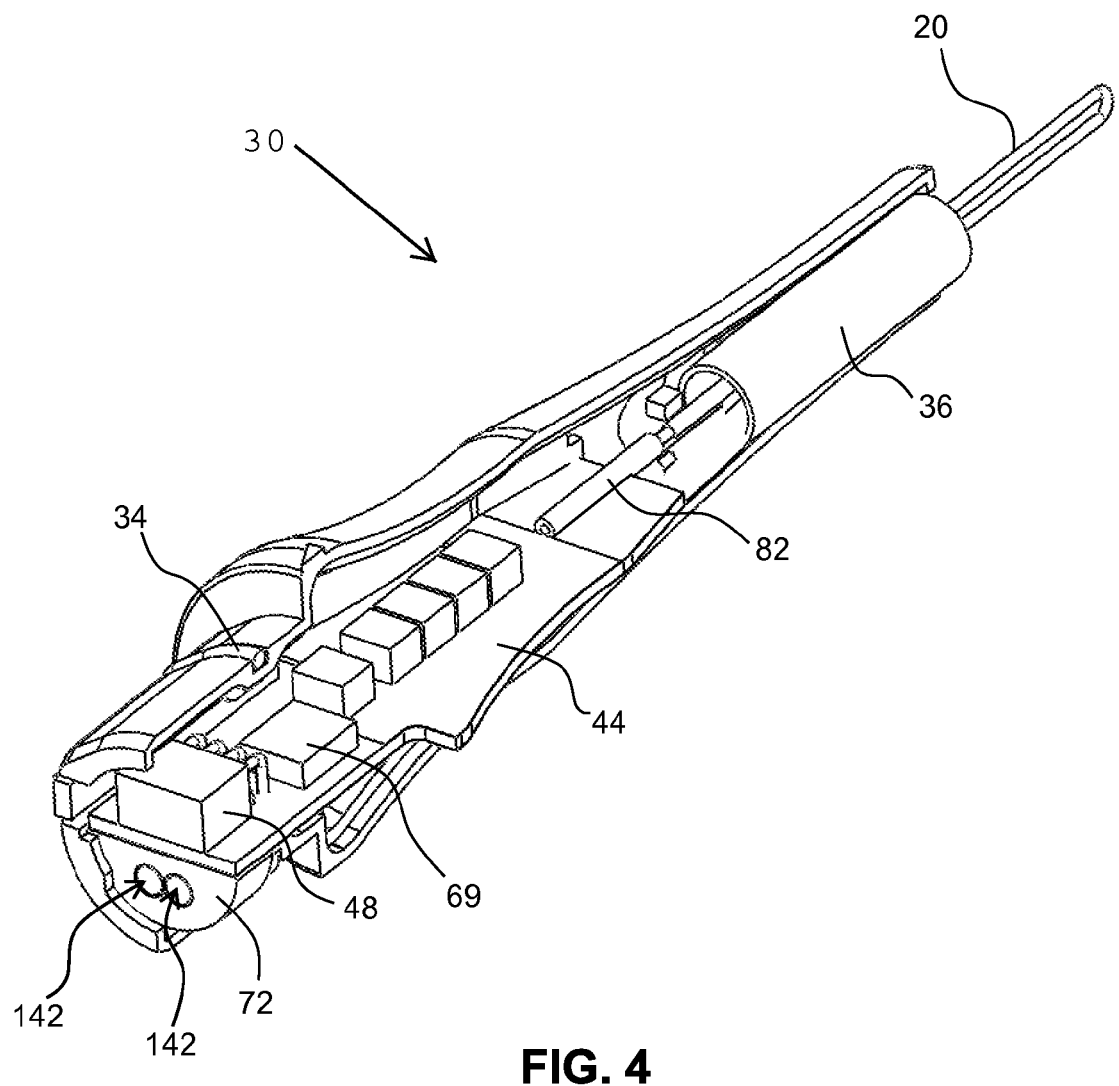
FIG. 4 shows a rear, perspective view of a removable tip according to principles of the present invention.

Additionally, when the tip 30 is connected to the body 40, coolant flow is directed into the tip 30 through a channel 142. The body 40 may include a raised lip 64 adjacent the channel 142. The raised lip 64 may press into a resilient material (FIG. 4, reference numeral 72), such as rubber, disposed on the tip 30 to create a seal which minimizes coolant flow leaking from the channel 142 when the tip 30 is connected to the body 40. Alternatively, the tip 30 may be connected to the body 40 using a Luer taper or other connectors. For example, the body 40 may include a male-taper fitting and the tip 30 may include a mating female part for making a leak-free connection between the tubes 140a and 140b (FIGS. 2C and 2D). It will be appreciated that other leak-free connection methods may be used to prevent leaking of coolant flow from one or more channels 142, such as a butt joint.

Figure 5A:
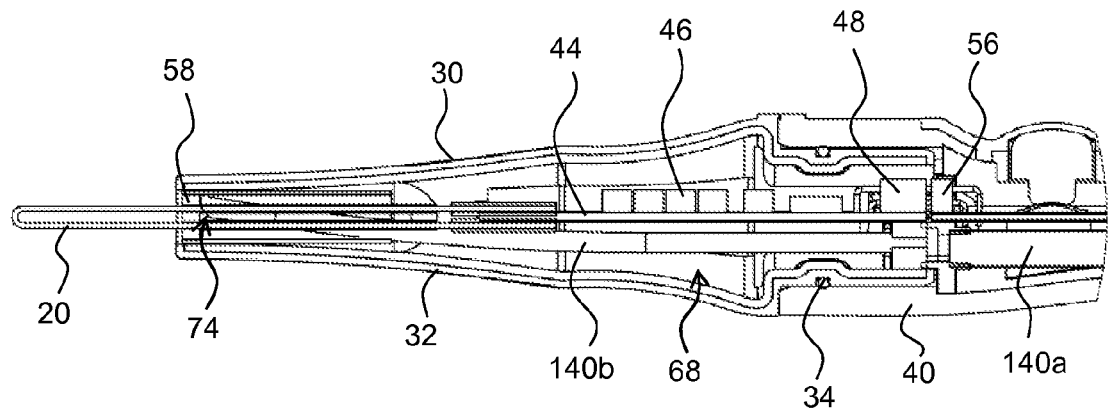
FIG. 5A shows a side, cross-sectional view of a surgical tip of the present invention.
Figure 5B:
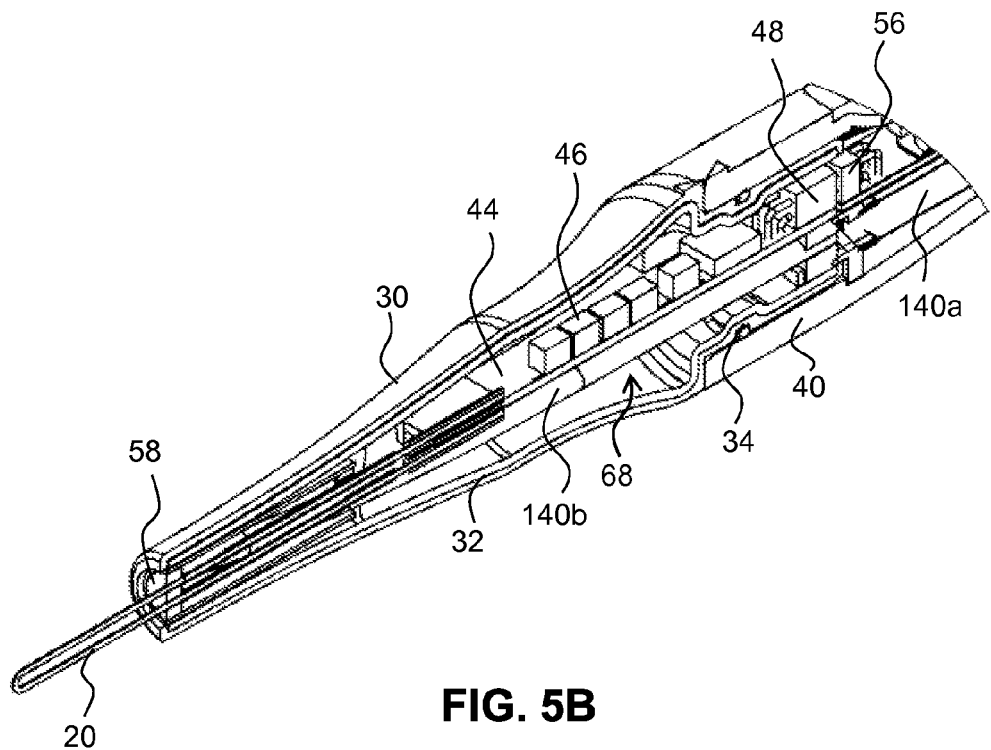
FIG. 5B shows a perspective, cut-away view of a surgical tip of the present invention.

Turning now to FIGS. 5A and 5B, close-up cutaway views are shown of a tip 30 connected to a body 40. The tip 30 may include an enclosing member 58 disposed adjacent the proximal end of the tip 30, and adjacent the active thermal member 20. The enclosing member 58 maybe disc comprised of a high heat resistant material such ceramic, Kapton, etc., to limit heat transfer from the thermal element 20 to the remaining structures of the tip 30. The enclosing member 58 may also be configured to receive the thermal element 20 to provide support for the thermal element during use of the handpiece 10.

As can be seen if FIG. 5A, the tube 140b may extend through the tip 30 from where the tip 30 connects with the body 40 to the proximal end of the tip 30 adjacent the enclosing member 58. Thus, cooling airflow or other coolant flow may be directed first to the proximal end of the tip 30 where heat build-up due to conductance from the thermal element 20 will be most prevalent. The enclosing member 58 may also include one or more apertures which direct at least part of the coolant flow toward the heating element 20, as will be described in more detail below.

Coolant flow from the tube 140b may reflect off of the enclosing member 58 and be directed rearwardly into void 68 to thereby cool the tip housing 32 and any structures located therein. For example, the tube 140b may have a beveled end 74 which allows fluid to easily flow from the tube 140 and reflect off the enclosing member 58. The coolant flow may then pass into the body 40 of the handpiece 10 through the opening 78 and 76 in the tip 30 and recess 54 of the body 40, respectively.

Alternatively, coolant flow through the handpiece 10 may be reversed. For example, a suction force may be applied to the handpiece 10 via channel 142 (FIGS. 2C and 2D) such that air or other fluid is drawn into the handpiece 10 to actively cool the various structures of the handpiece 10. In such a configuration, fluid introduced into the handpiece 10 would exit through tubes 140a and 140b.

Turning now to FIGS. 6A through 6G, other removable tips 30, and components thereof, for attaching to a body 40 of a handpiece 10 of the present invention (see e.g. FIG. 3) are shown. The tip 30 may have a housing 32 with a keyed portion 32a for attachment to the body 40 in a similar fashion to tips described above. The tip 30 shown in FIGS. 6A-6G, however, may include an elongate tube 84 which extends away from the tip housing 32. The elongate tube 84 may be comprised of an electrical conductive material, such as copper, brass, etc. and the thermal element 20 may be attached to the proximal end of the elongate tube 84. Thus, electrical energy may be supplied to the thermal element 20 via the elongate tube 84.

By extending the thermal element 20 away from the tip housing 32, a thermal surgical tool of the present invention may be used to treat tissues located deeper within a patient's body, such as organs located in the body cavity. Such a configuration may also make it easier for a surgeon to treat tissue near the skin of a patient by increasing the visibility of the surgical site. For example, the surgeon may be able to better see the thermal element 20 contact tissue in a surgical site without other structures, such as housing 32, obstructing his or her view.

Figure 6A:
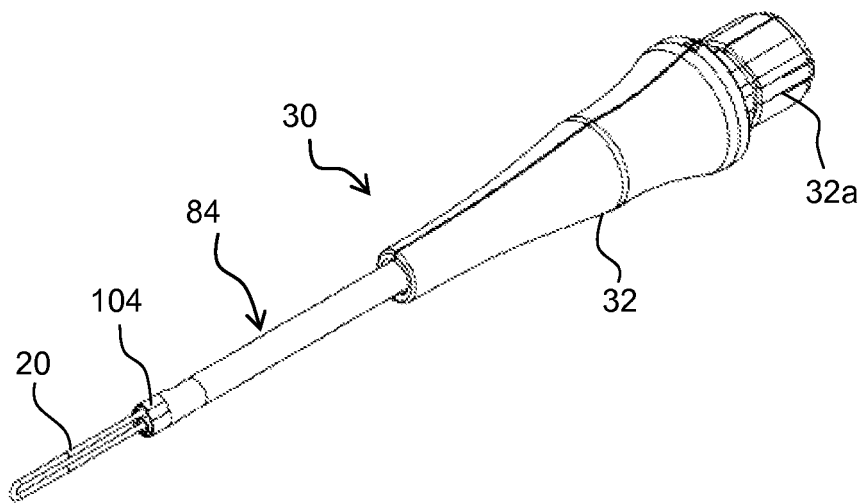
FIG. 6A shows a perspective view of another surgical tip of the present invention.
Figure 6B:
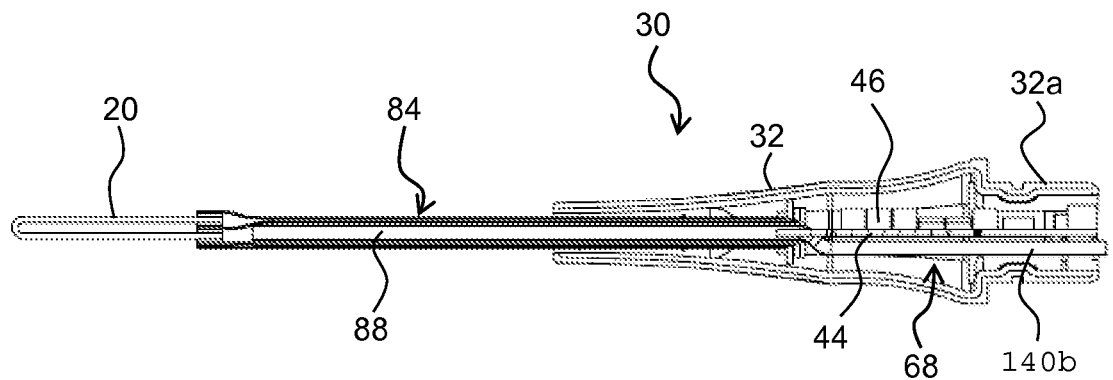
FIG. 6B shows a side, cross-sectional view of the tip in FIG. 6A.
Figure 6C:
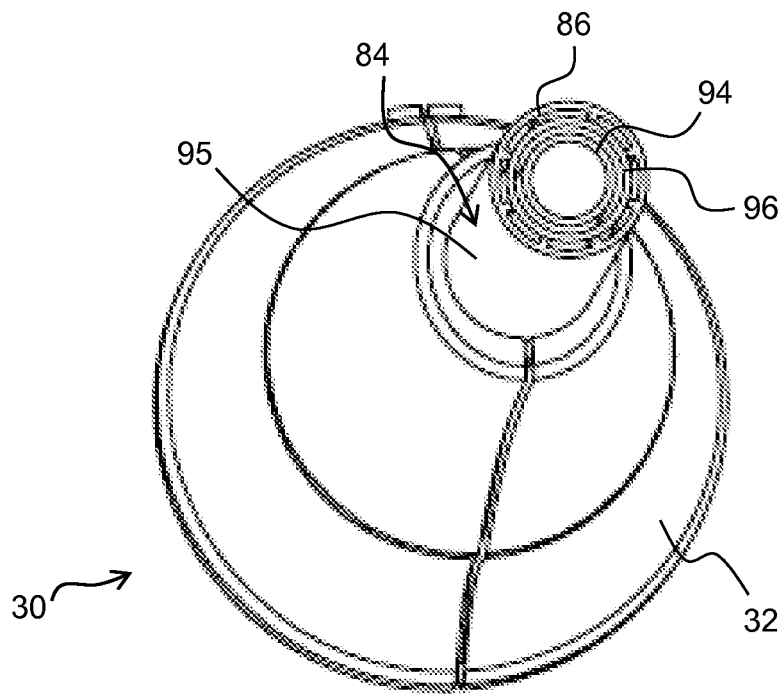
FIG. 6C shows a front, perspective view of a surgical tip having an elongate tube, with a cross-section view of an elongate tube.

FIG. 6B shows a side, cross-sectional view of a surgical tip 30 having an elongate tube 84. According to principles of the present invention, coolant flow may be used to cool the tip 30 and structures associated therewith. As can be seen, a cooling fluid may be directed into a void 88 located in the elongate tube 84 from the tube 140b supplying a cooling fluid. (The tube 140b may be connected to a cooling fluid supply in any manner described herein). As is more clearly shown in FIG. 6E, the elongate tube 84 may comprise two concentric tubes 94, 96 having an insulating material 102 disposed therebetween (see FIG. 6E), or may use parallel tubes, etc. to move the cooling fluid through the elongate tube 84. The cooling fluid may flow through the void 88 toward the proximal end of the elongate tube 84, enter openings 92 (FIG. 6E) and return toward the tip 30 along a parallel path. The cooling fluid may then flow through the void 68 to cool components located therein, into the handpiece 40, and exit near the distal end 50 of the handpiece 40.

Figure 6D:
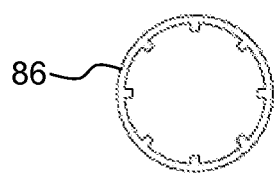
FIG. 6D shows a front view of a spline.
Figure 6E:
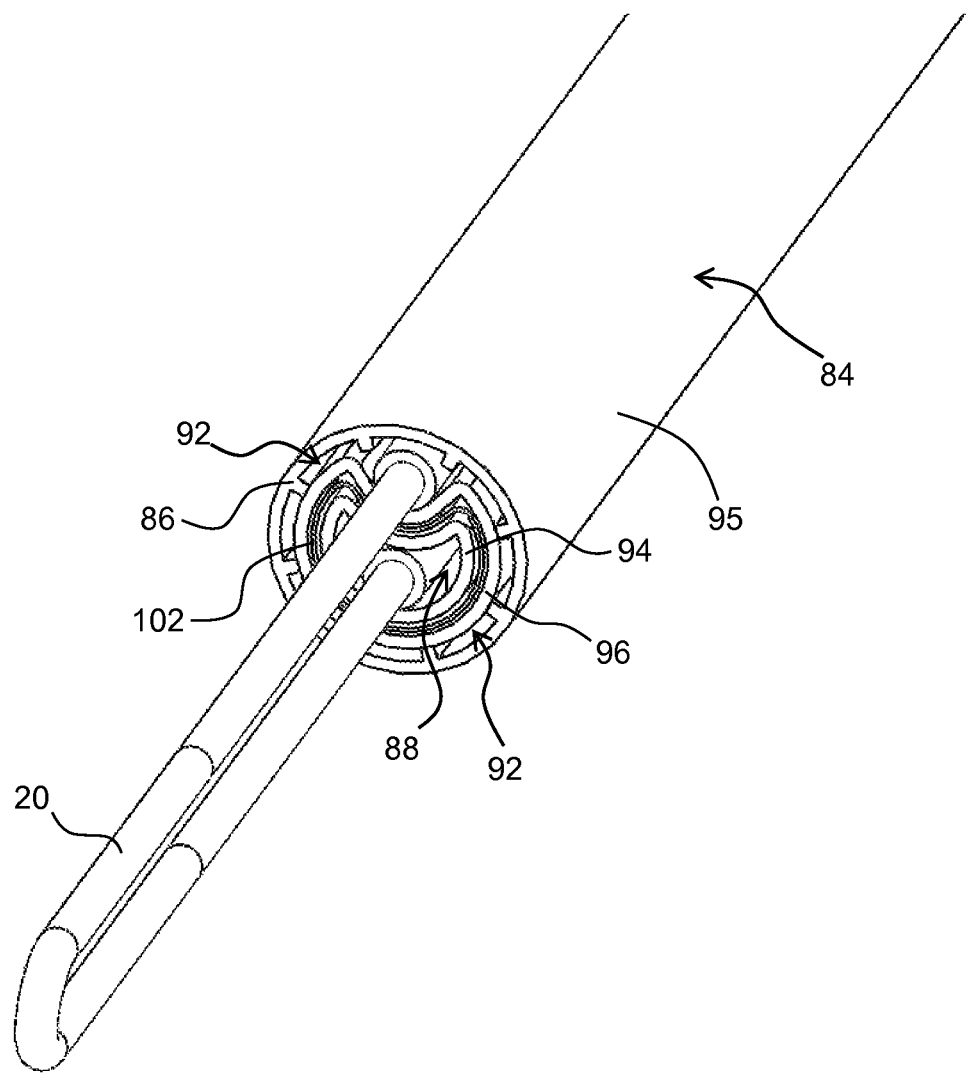
FIG. 6E shows a close-up, perspective view of a surgical tip according to one aspect of the present invention.
Figure 6F:
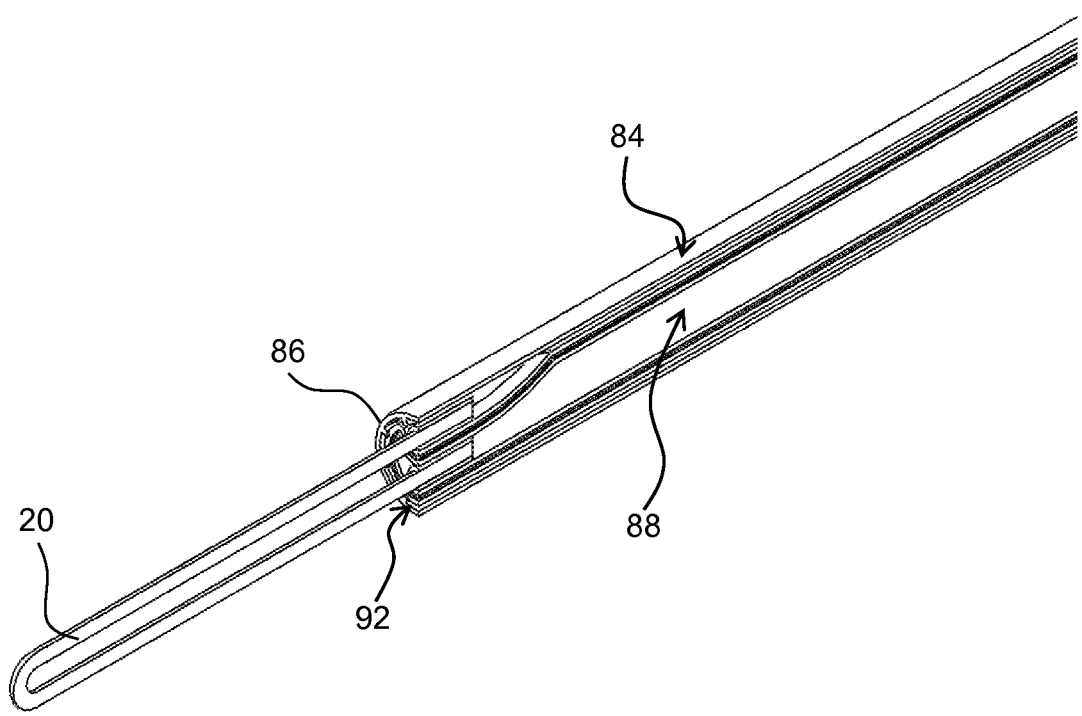
FIG. 6F shows a side, perspective cross-sectional view of a surgical tip of the present invention.

As is best seen in FIG. 6E, the elongate tube may comprise an outer tube 95, which extends around two inner, electrically conductive tubes 94, 96. A spline 86 (an end view of which is shown in FIG. 6D) may form the outer tube 95 and may be disposed about tube 96 creating a space for coolant flow to travel. The outer tube 95 or spline 86 may be thermally and electrically insulative to prevent damage to tissue it comes into contact with. The outer tube 95 may also be biocompatible.

A cap 104 may be disposed on the proximal end of the elongate tube 84 to redirect coolant flow from void 88 into openings 92 where it travels back toward the tip 30 through the space between the outer tube 95 and inner tube 96. (Flow may also be in the reverse direction). Thus, thermal energy which is conductively transferred to the elongate tube 84 from the thermal element 20 may be removed. It will be appreciated that the direction of the coolant flow through the elongate tube 84 may be reversed by, for example, applying a suction force which draws air in along the space between the outer tube 95 and the inner tube 96 and exits through void 88.

According to one aspect of the invention, the tube 94 and 96 may comprise a material which has good thermal conductivity properties, such as aluminum, to facilitate transfer of thermal energy from the elongate tube 84 to the coolant flow traveling therethrough. The insulating material 102 between the electrically conductive inner tubes 94, 96 may comprise Kapton, Teflon, or the like.

Figure 6G:
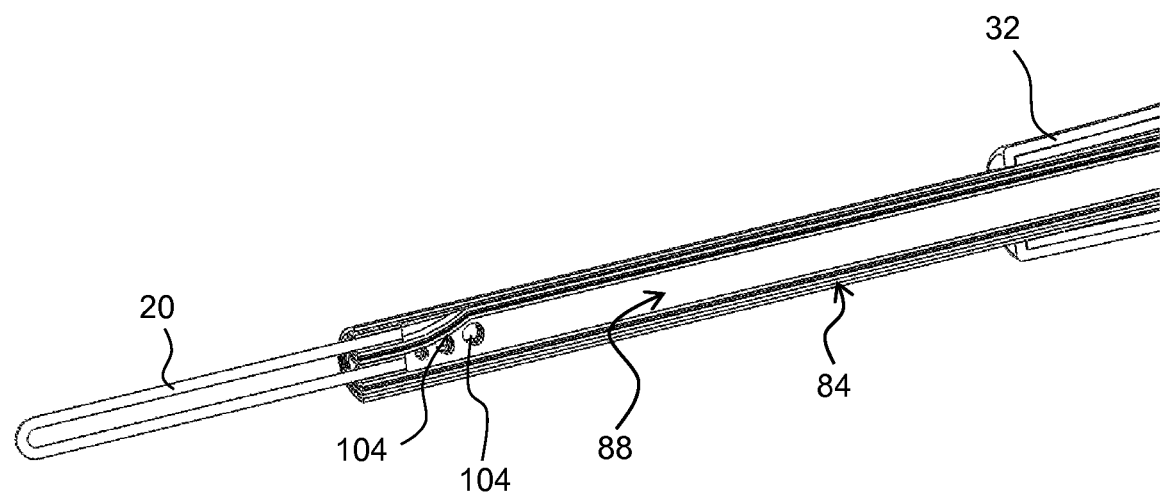
FIG. 6G shows a side, perspective cross-sectional view of another surgical tip of the present invention.

Referring now to FIG. 6G, a side, cross-section view of a removable tip 30 comprising an elongate tube 84 is shown. According to one aspect of the invention, one or more apertures 104 may be located along the elongate tube 84. Cooling fluid may flow through void 88 to cool the elongate tube and be released through the one or more apertures 104. The removable tip 30 may also include additional apertures which direct coolant flow towards the thermal element 20 to cool the thermal element more rapidly, similar to other tips described herein.

Figure 7A:
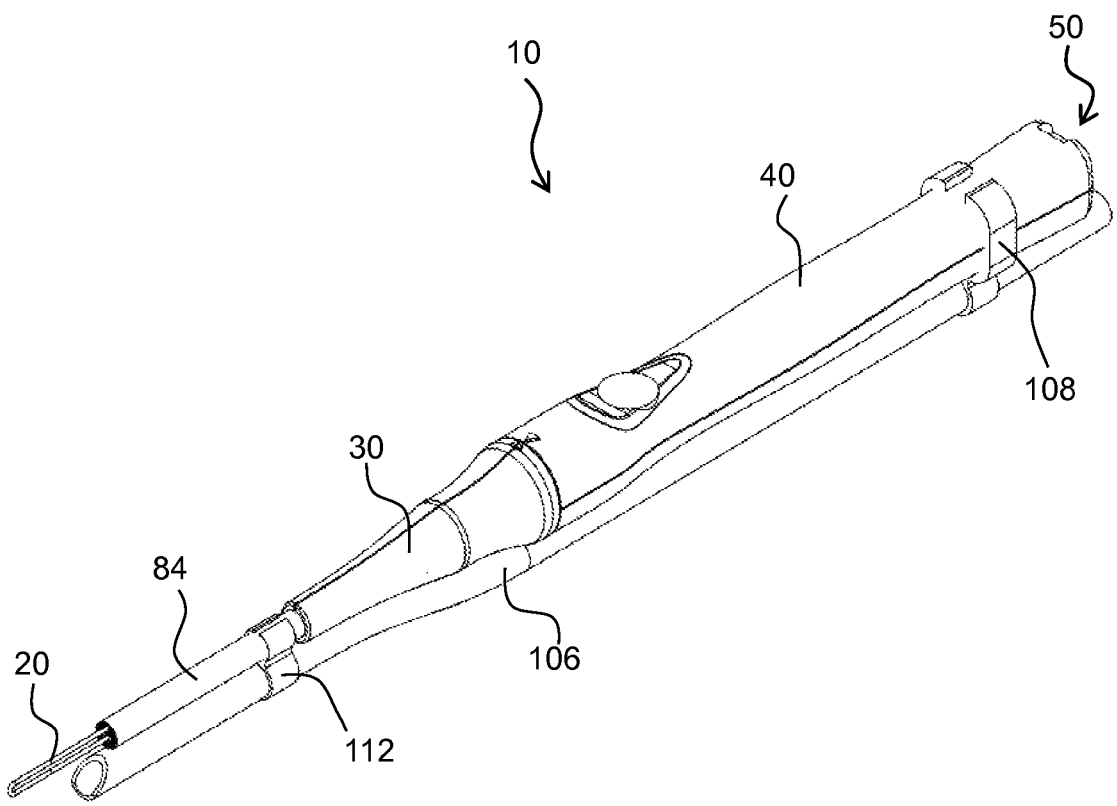
FIG. 7A shows a perspective view of a thermal surgical instrument according to one aspect of the invention.
Figure 7B:
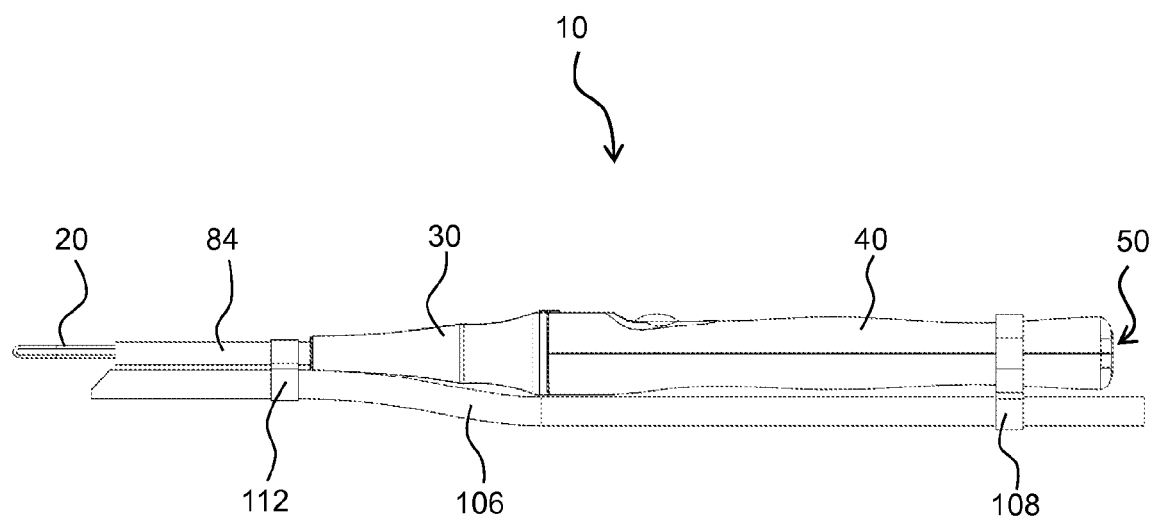
FIG. 7B shows a side view of the thermal surgical instrument of FIG. 7A.
Figure 7C:
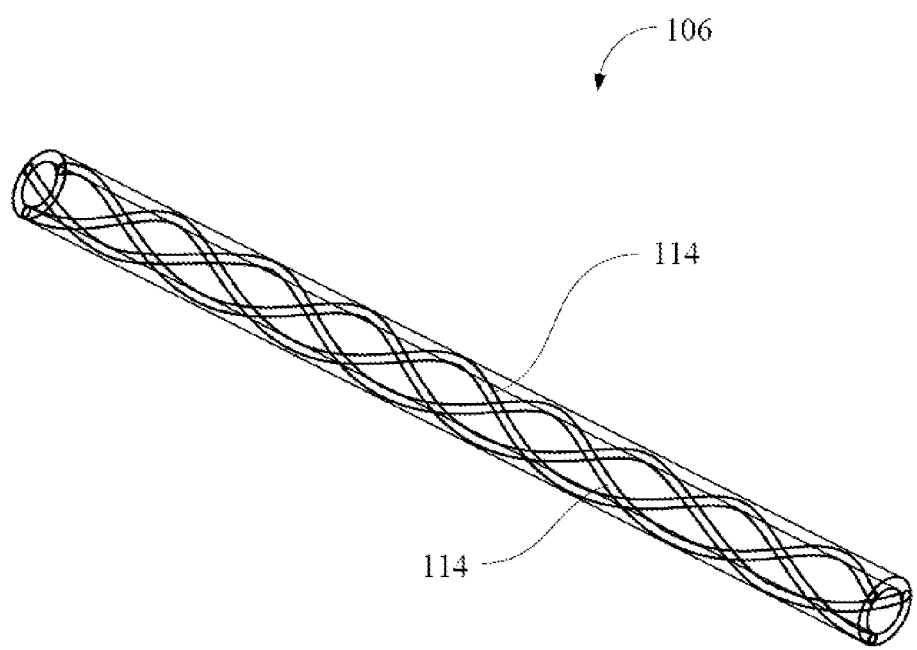
FIG. 7C shows a perspective view of a tube in accordance with principles of the present invention.

Turning now to FIGS. 7A and 7B, a perspective view and side view, respectively, are shown of a thermal surgical tool, generally indicated at 10, according to one aspect of the present invention. The thermal surgical tool 10 may include a cooling system such as those described herein. Additionally, the tool 10 may include a separate system for removing smoke or other aerial contaminants created by thermally treating tissue. The system may include a tube 106 attached to the tool 10 using one or more clips 108, 112. The tube 106 may be connected to a suction device so that smoke or other aerial contaminants may be drawn away from the surgical site during while the tool 10 is being used. FIG. 7C shows a perspective view of the tube 106. The tube 106 may comprise one or more support wires 114 disposed within the walls of the tube 106. Thus the shape of the tube 106 may be changed and the support wires 114 may hold the tube in that desired shape.

By removing the smoke and other airborne debris created while thermally treating tissue (thermal cutting, ablation, sealing, etc.), the surgeon is better able to see the tissue being treated and the smell of burnt tissue can be reduced. The tube 106 may be disposed in communication with a control switch so that the surgeon can turn on suction when needed and off when it is not.

Figure 8:
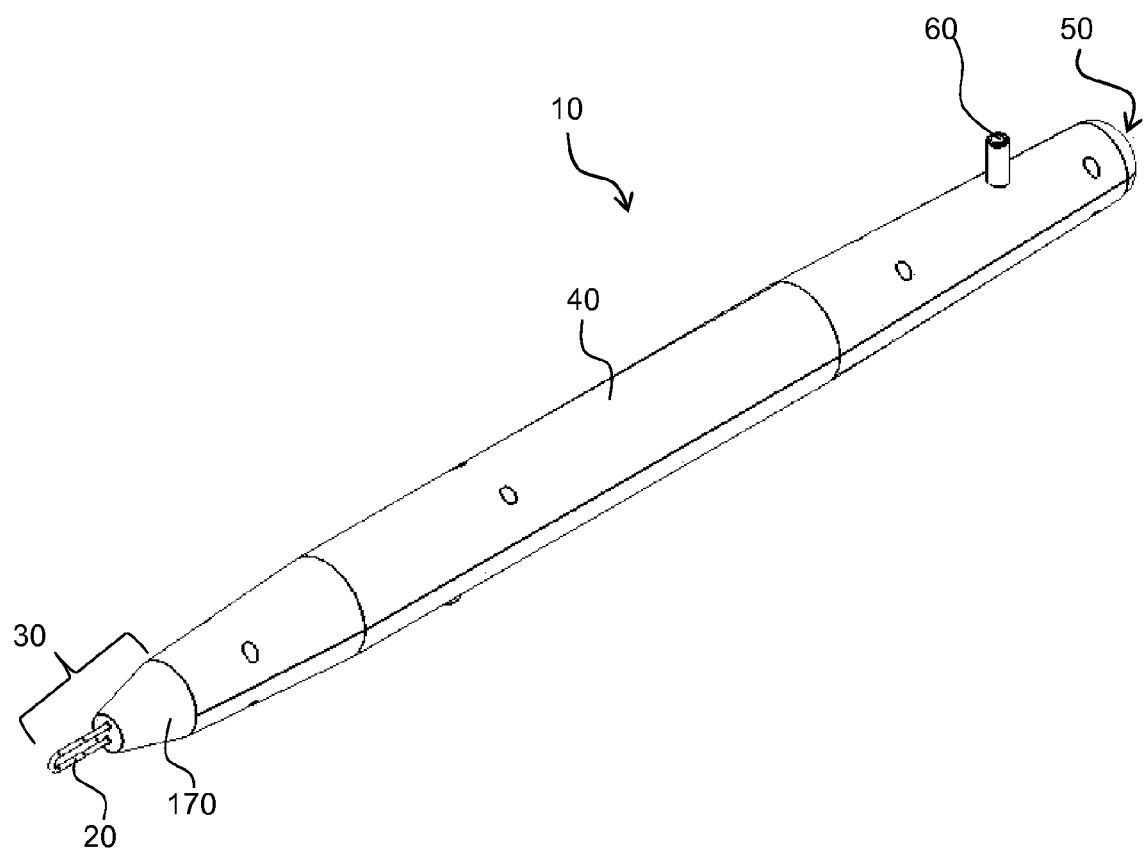
FIG. 8 shows a perspective view of a handpiece with a cooling system in accordance with the present invention.

Turning now to FIG. 8, a perspective view of a handpiece, generally indicated at 10, with a cooling system in accordance with the present invention is shown. The handpiece 10 may include a fluid connection port 60 located at a position other than the distal end 50 of the handpiece 10 (as opposed to the distal end as shown in some other figures). Similar to the handpiece 10 described above, a fluid may be directed into the handpiece 10 via the fluid connection port 60 to actively cool the tip 30, body 40, and/or internal components, and keep the external surfaces within a temperature range that makes it comfortable to hold the handpiece 10. Alternatively, a suction force may be applied to the fluid connection port 60 to cause coolant flow through the handpiece 10 in the opposite direction. (It will be appreciated that suction could also be applied to the distal end 50 so that port 60 would be the fluid intake). As the cooling fluid circulates through the body 40, regardless of whether it engages the tip 30, the cooling fluid absorbs heats and cools the body, thereby lessening the likelihood of the body becoming uncomfortably warm. This is particularly advantageous during long surgical procedures where temperature would tend to accumulate if not vented and where the heat in the handle portion could become more uncomfortable.

Figure 9:
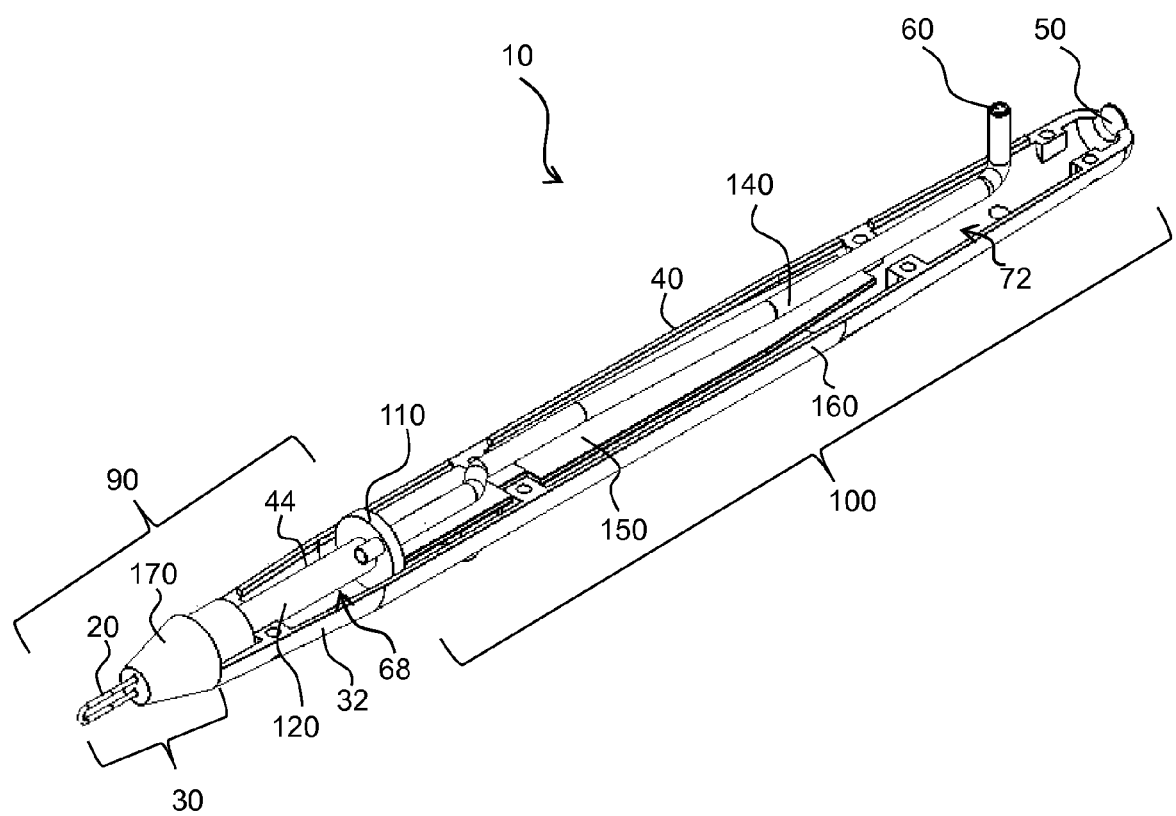
FIG. 9 shows a perspective view of the top of an open handpiece with a cooling system in accordance with one aspect of the present invention.

Turning now to FIG. 9, a side, cutaway view is shown of a thermal surgical tool, generally indicated at 10, which includes a cooling system. Thermal surgical tool 10 may comprise a two-sectioned active cooling handpiece 40. The two-sectioned handpiece 40 may include a primary section 90 and a secondary section 100. Thermal energy that is generated during use of the thermal surgical tool 10 may be transferred to a cooling fluid which is circulated through the handpiece 40. More heat may build-up in the primary section 90 because of its proximity to thermal element 20. Thus, the primary section 90 may be the focus of heat removal. The cooling fluid may then pass out of the primary section 90 into the secondary section 100 to provide cooling to the secondary section and structures disposed therein as well. The sections may be separated by a divider 110, which may include an O-ring, or other structure for controlling coolant flow.

The primary section 90 of the handpiece 40 may include a tip 30 which has a thermal surgical element 20 and a retaining structure 170, which holds the thermal element 20. The retaining structure 170 may be desired, at least in part, to help thermally isolate the thermal element 20 from the remainder of the handpiece 40. The handpiece 40 may also include a heat sink 120 which may be attached to or formed integrally with the retaining structure 170 and a primary case or housing 32.

As shown in FIG. 9, a conduit 140 forming a flow channel may extend from the fluid connection site 60 to a position adjacent the heat sink 120. Thus, the fluid connection site 60 may be positioned in the secondary section 100 and the conduit 140 may extend into the primary section 90 to carry air or other cooling fluid to the primary section 90.

Release of a cooling fluid into a void 68 in the primary section 90 which surrounds the heat sink 120 will draw heat out of the heat sink and cool the handpiece 10 as it passes over the heat sink, absorbs heat and then passes out of the handpiece. Likewise, the conduit 140 could be configured to hold the cooling fluid throughout its travel, wherein heat is transferred to the fluid through the conduit 140.

The void 68 may be defined by a handpiece outerwall 44 and the heat sink 120, and/or other structures. The heat sink 120 may be configured to absorb thermal load from the thermal element 20. As cooling fluid passes into the void 68 from the conduit 140, heat from the heat sink 120 is transferred to the cooling fluid, such as air, thereby cooling the heat sink.

Disposed at one end of the primary section 90 may be a retaining structure 170. The void 68 may extend into the retaining structure 170 so that the air or other cooling fluid passing into the void 68 also dissipates heat from the retaining structure 170.

The secondary section 100 may contain an fluid connection port 60, conduit 140, circuit board 150, secondary case 160 comprising a void 72, along with a rear exit 50 disposed along or at an end of the void 72 near the distal end of the surgical tool 10. As will be discussed in additional detail below, the handpiece 40 can be configured so that heated air or other cooling fluid from the primary section 90 can pass into the void 72 or other channels of the secondary section 100, pass over structures contained therein, and be vented out the rear exit or port. Thus, a continual stream of cooling fluid can dissipate heat from the heat sink 120, the retaining structure 170 and any electronic components contained in the secondary section 100 of the handpiece 40. If a liquid cooling fluid is used, a return line would typically be attached to the handpiece 40 and may be attached at the distal end 50.

Turning now to FIGS. 10A through 10D, coolant flow in a thermal surgical tool 10 is shown by a series of arrows in handpieces 40a-40d. The handpieces may have rear-exit cooling (handpiece 40a, FIG. 10A), rear and front exit cooling (handpiece 40b, FIG. 10B), front-exit cooling (handpiece 40c FIG. 10C), or vacuum cooling where cooling fluid is drawn into the handpiece (handpiece 40d FIG. 10D). Each system may have advantages over the other depending on the surgical procedure being performed and/or the preferences of the surgeon. For example, the handpiece 40b may have an adjustment member 174, such as a valve, to adjust the amount of coolant flow (gas, liquid, etc.) that passes through the front exits. Coolant flow may be adjusted by rotation of the divider 110 (FIG. 9), or by using other flow control mechanisms. The handpiece 40b can be adjusted to be rear-exit cooling only or front-exit cooling only depending on the desire of the surgeon at any given moment.

While air is generally discussed as the method for cooling a handpiece for simplifying the disclosure, it should be recognized that other coolants may be adapted to this system, such as liquid cooling, e.g. saline solution or other solutions. Similarly, while "air" is discussed, specific gasses may provide better advantages. For instance, carbon dioxide gas may be more desirable than air because of its solubility in liquids and thus reduced risk of air embolisms in an invasive surgical procedure. Helium gas may be desirable because its characteristics include, being non-flammable, colorless and clear. Further, with helium, respiratory acidosis may be avoided. Similarly, nitrogen gas or argon gas may also be used. It may be desirable to include humidity in the gas stream if directed at a surgical site, as blowing dry gas may cause tissue to become desiccated.

Figure 10A:
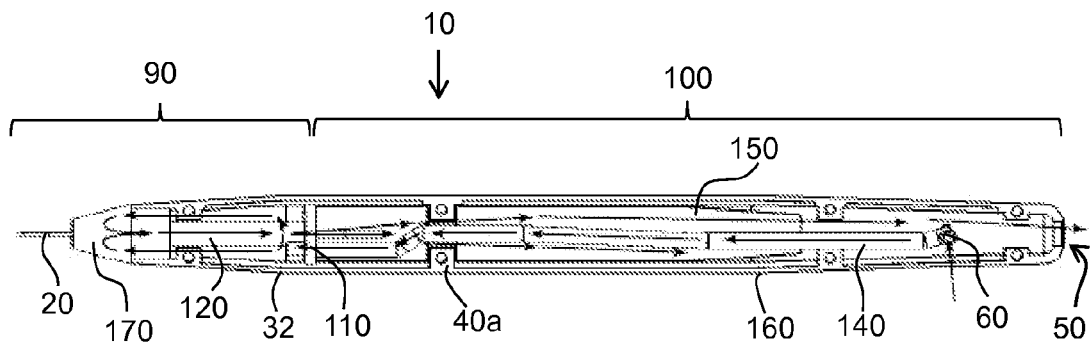
FIG. 10A shows a plan view of the handpiece of FIG. 9 with a rear vented cooling system in accordance with one aspect of the present invention.

In FIG. 10A, a top, plan view of a handpiece 40a with a rear vented cooling system is shown. Air (or other cooling fluid) may be directed into the fluid connection port or site 60, through conduit 140 and divider 110 and into the primary section 90. As the air travels through the primary section 90, the air is heated and the structures in the primary section are cooled.

The coolant may circulate in the void around the heat-sink 120. At the proximal end of the primary section 90, the coolant may pass over or through a portion of the retaining structure 170 and then be directed back down along or through the interior of the heat-sink 120 to the secondary section 100. The heat sink may include a bore, channel or other structure configured for movement of the coolant out of the primary section 90.

The coolant may then circulate around or pass over the internal components of the secondary section 100, such as a circuit board 150, other electronics, etc. and flow toward the distal end 50 of the handpiece 40*a*. It will be appreciated that the interior of the surgical tool 10 may be formed from multiple components which may be attached to one another or formed integrally with one another. As the coolant passes over the components it tends to draw heat out of the components and to carry the heat out of the surgical handpiece 40*a*, thereby keeping the handpiece 40*a* from becoming uncomfortably hot.

Further refinements may also allow more thermal energy to escape. It has been noted that a retaining structure 170 having a polyimide cone may aid in the reduction of residual thermal energy because of its small heat capacity and relatively high thermal conductivity. This allows heat from the thermal element 20 to pass quickly to the heat sink 120 without storing that heat in the retaining structure 170 such as a cone. Polyimides that appear useful for such purposes include KAPTON® from Dupont Electronic Technologies, US Rt. 23 South & DuPont Road, P.O. Box 89, Circleville, Ohio USA 43113; and MELDIN® from Saint-Gobain Performance Plastics, 7301 Orangewood Avenue, Garden Grove, Calif., USA.

Figure 10B:
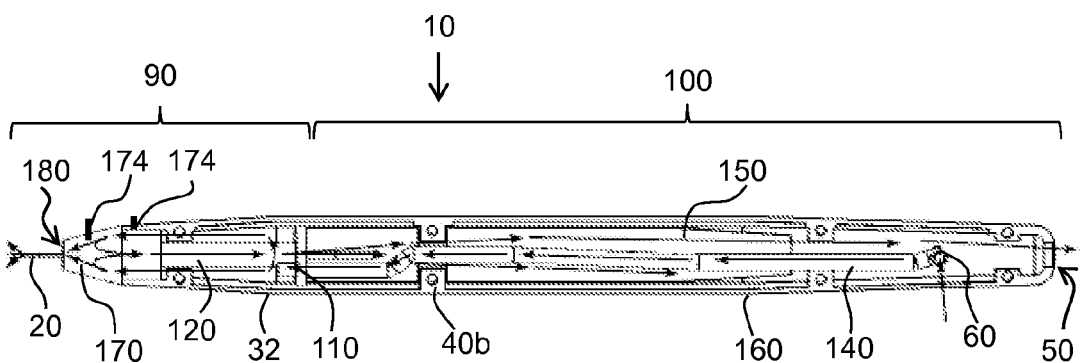
FIG. 10B shows a plan view of a handpiece with a front and rear vented cooling system in accordance with another aspect of the present invention.

Turning now to FIG. 10B, a top view of a handpiece 40*b* with a front and rear vented cooling system is shown. The overall structure of handpiece 40*b* and handpiece 40*a* are similar and thus each element is not specifically discussed with respect to FIG. 10B. However, it will be appreciated that each of the structures discussed regarding FIG. 10A may be present.

The general direction of the coolant flow for the rear vented portion may follow a similar a similar path as described FIG. 10A. However, an aperture 180 located in the retaining structure 170 or adjacent thereto may allow an amount of cooling fluid to exit at or toward the front of the handpiece 40*b*. The coolant exiting from the front of the handpiece 40*b* may be directed toward the surgical element 20 so that the coolant cools the element. If desired, the coolant could continually be directed at the surgical element 20, or could be controlled with a valve 174 to allow air to be blown only when the surgical element is not active to thereby remove unwanted heat. In the alternative, the valve can be opened so that air is directed to drive body fluids away from the area in which the surgical element 20 is being used.

The handpiece 40*b* may include a regulator, control or valve 174 which can be used to regulate the amount of air which is being directed out of the forward end of the handpiece 40*b*. The valve 174 may also be able to completely terminate coolant flow through the forward end of the handpiece 40*b* to thereby direct all of the coolant out of the rear. Thus, a surgeon may be able to control when and if coolant is presented to the area being operated on. The flow of coolant through the primary section 90 may also help cool the retaining structure 170. Furthermore, flow channels could be formed in the retaining structure 170 to facilitate air movement and heat dissipation.

Some or all of the coolant may also be directed back down along the heat sink 120 or through the center of the heat-sink to the secondary section 100. The coolant passing into the secondary section 100 can pick up additional heat and then be vented out the back. (The coolant may also be vented into a suction hose or other tubing to prevent release into the operating room if desired).

The coolant flow may be adjustable such that a percentage flows out the front aperture 180 and distal end 50 in a variety of ways. For example, the handpiece 40*b* may be twisted to adjust the forward aperture opening thereby regulating flow. Alternatively, a slider or other restrictor may be used to adjust the percentage of coolant flow out the front aperture 180 and distal end 50.

Figure 10C:
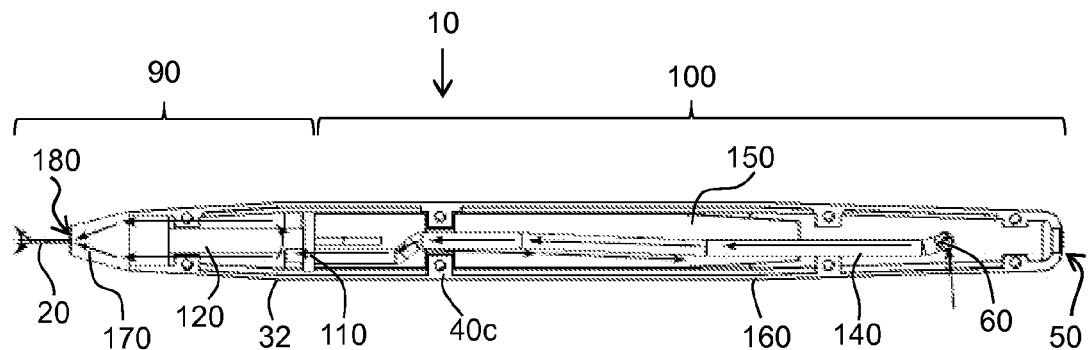
FIG. 10C shows a plan view of a handpiece with a front vented cooling system in accordance with still another aspect of the present invention.

Turning now to FIG. 10C, a top view of a handpiece 40*c* with a front vented cooling system is shown. Similar to FIGS. 10A and 10B, air or other cooling fluid is directed into a fluid connection site 60 through the conduit 140 and the divider 110 and into a primary section 90. The coolant may encircle a heat sink 120 and be directed forward to the retaining structure 170. However, rather than returning through or by the heat sink 120, all the coolant may exit through a front aperture 180. The secondary section 100 may be passively cooled or separately cooled. As with FIG. 10B, the coolant may be directed at the thermal element 20 and/or tissue being treated therewith, or the coolant may be vented from an opening that directs the air away from the handpiece 40*c*, such as escaping at an angle relative to the orientation of the thermal element 20. Likewise, a valve similar to valve 174 could be used to enable a surgeon to select which direction the venting of the heated cooling fluid would occur.

A front-vented handpiece such as 40*c* may provide advantages. By venting air directly over the thermal element 20, the element may be more quickly cooled than by thermal conduction alone. Furthermore, forward directed coolant may cause liquids to disperse away from the surgical site and the thermal element 20, improving visibility of the interaction of the thermal element 20 with tissue. By reducing the amount of liquid in the surgical site, the thermal element 20 may have better performance because it does not have to work in a submerged environment.

Figure 10D:
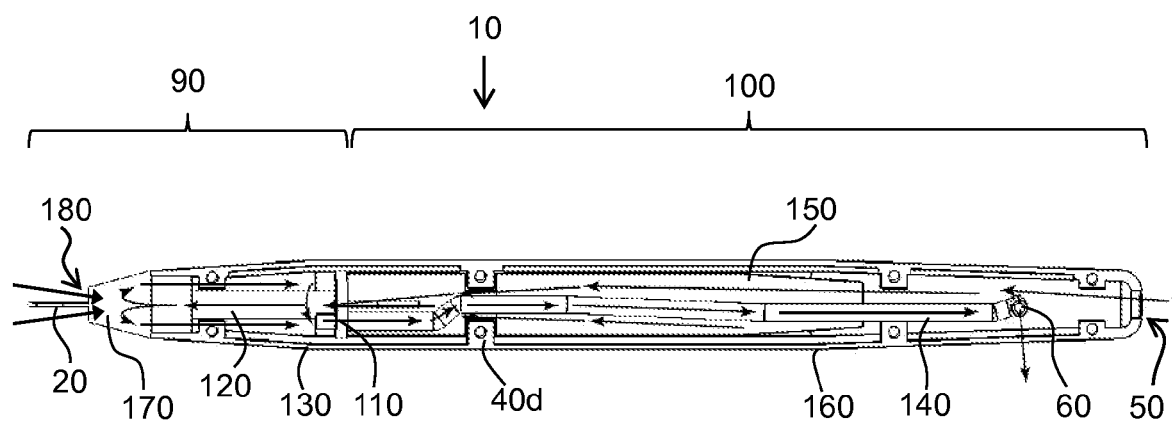
FIG. 10D shows a plan view of a handpiece with a vacuum based cooling system.

Turning now to FIG. 10D, a plan view of a handpiece 40*d* with a vacuum based cooling system is shown. The design of the handpiece 40*d* may be generally similar to the handpieces 40*a-c* shown in FIGS. 10A-10C, but the coolant flow may be reversed. Thus, the coolant can be drawn in from a different opening located in the handpiece 40*d*, such as an opening at the distal end 50 in a reverse flow pattern from that shown in FIG. 10B. Alternatively, a vacuum system may be created such that coolant is drawn in through a front aperture 180 into the handpiece as shown in FIG. 13D.

In the alternative, or in addition, air may be drawn into the aperture 180 through the primary section 90 and over heat sink 120. Depending on the specific embodiment, the air may pass through conduit 140 and out the distal end 50, or through the secondary section 100 generally. Fluid connection site or port 60 may be connected to a vacuum pump, such that suction may be provided to the handpiece 40*d*.

The vacuum may provide advantages to the surgeon. The vacuum system may be able to draw in air to aid in cooling of the primary section 90 and the secondary section 100. Furthermore, the system may also draw in smoke or other aerial contaminants created by thermally treating tissue that may hinder a surgeon's progress. In the case of smoke, the surgeon may be able to see better as the smoke is removed.

Figure 11A:
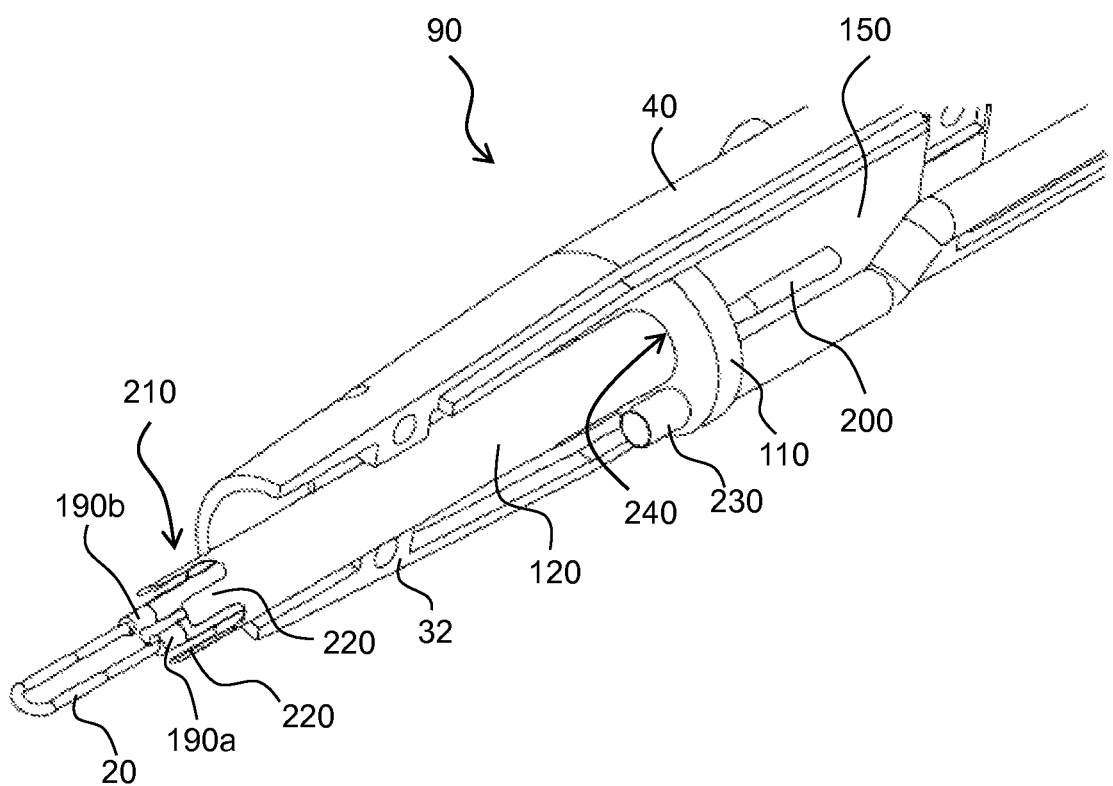
FIG. 11A shows a cut-away perspective view of an open tip of a surgical handpiece with cooling system in accordance with yet another aspect of the present invention.

Turning now to FIGS. 11A through 11O, the primary section 90 of surgical handpiece with a cooling system of the present invention is shown. Visually, the retaining structure 170 has been removed to show underlying structures of the primary section 90. However, it should be noted that the coolant-flow diagrams will continue to consider the primary section 90 with the retaining structure 170 in place. FIG. 11A is used to show the structures, while FIGS. 11B and 11C discuss coolant flow.

Referring now to FIG. 11A, according to one aspect of the invention, the thermal element 20 may include conductive stand-offs 190*a*, 190*b* disposed adjacent to or within the heat sink 120. The heat sink 120 may include a first end 210 with fins 220 which may help direct air into the heat sink 120.

Figure 11B:
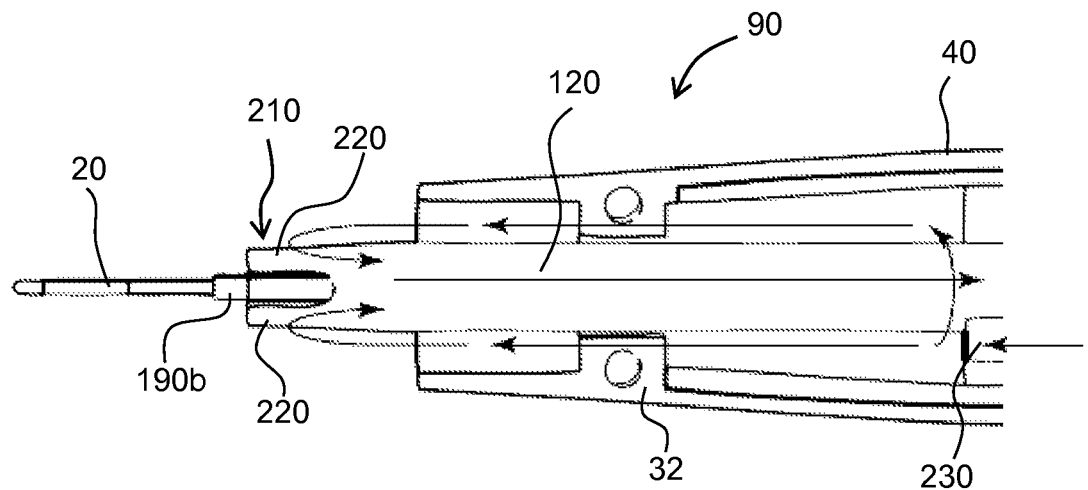
FIG. 11B shows a plan view of an open tip of a surgical handpiece with a rear vented cooling system in accordance with still another aspect of the present invention.

Referring now to FIG. 11B, a close-up, fragmented top view of the primary section 90 of a surgical handpiece with a rear vented cooling system is shown. According to one aspect of the invention, coolant may enter the primary section 90 through a port 230. The air may then circulate around the heat sink 120 and move toward the first end 210 of the heat sink 120. The air is then directed between the fins 220 and down the center of the heat sink 120 into the secondary section 100 (not shown).

This cooling method provides several advantages. After the air enters into the primary section 90, heat may be first transferred from the exterior surface of the heat sink 120 and the interior of the housing 32 to the air, thereby cooling these two important structures. The coolant may then pass through the center of the heat sink 120 providing further heat removal from the heat sink 120 and also from the stand-offs 190a, 190b. By passing over the outer surface of the heat sink 120 and then through the center of the heat sink 120, the effective cooling time of the primary section 90 may be reduced significantly because the convective path is near doubled. The coolant may then pass to the secondary section 100 through a center hole 240 (see FIG. 11A) in the divider 110. The coolant may then cool secondary section 100 components.

Figure 11C:
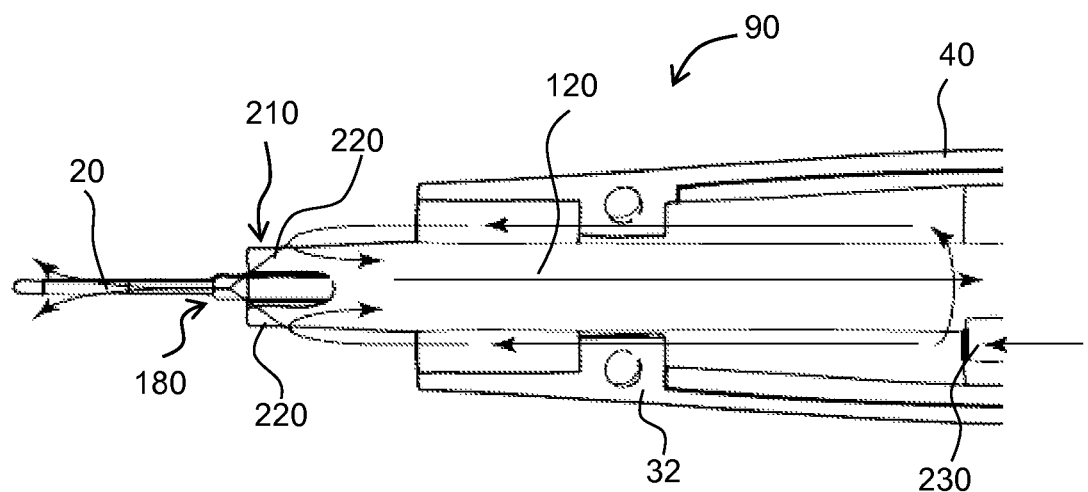
FIG. 11C shows a plan view of an open tip of a surgical handpiece with a front and rear vented cooling system.

Referring now to FIG. 11C, a top, fragmented view of the primary section of a surgical handpiece with front and rear vented cooling system is shown. The rear coolant flow is similar to the flow discussed in FIG. 11B. However, coolant, such as air, carbon dioxide or saline solution, may also be directed out a front aperture 180. Thus, the rear coolant flow may be reduced by an amount that corresponds to the amount of coolant which is released through the aperture 180. According to one aspect of the invention, the coolant is directed toward the active element 20, causing the thermal element 20 to cool more rapidly.

According to other aspects of the invention, the front aperture 180 may be used to provide specific advantages. For example, the front aperture 180 may be offset from the center of the retaining structure 170 such that the coolant flow is concentrated ahead of the active element 20 to better disperse liquid in front of the active element 20 as it is being used. Also, the handpiece 10 may include a control mechanism, such as a push button that opens the front aperture 180 when activated and closes the aperture 180 when deactivated, thus allowing the surgeon to control when front coolant flow is released from the aperture 180. Additionally, the front aperture 180 may open for a period of time after the thermal element 20 is turned off to cool the thermal element 20 more rapidly when not in use. Another example may include, the front aperture 180 being closed when the thermal element 20 is on, and open when the active element 20 is off. This configuration may allow the handpiece 40 to perform various functions during a procedure, such as dispersing liquid and thermally treating tissue.

A liquid dispersing modality may operate automatically as described above or manually by the surgeon. The handpiece 40 may include an additional control mechanism to further regulate the coolant flow through the handpiece 40 such as an on/off button and/or a flow control member. Operation of the flow control member may include twisting the handpiece, moving a slider, increase/decrease buttons or a series of flow setting buttons. These controls may affect the forward coolant flow, total coolant flow and/or rear coolant flow.

Figure 12A:
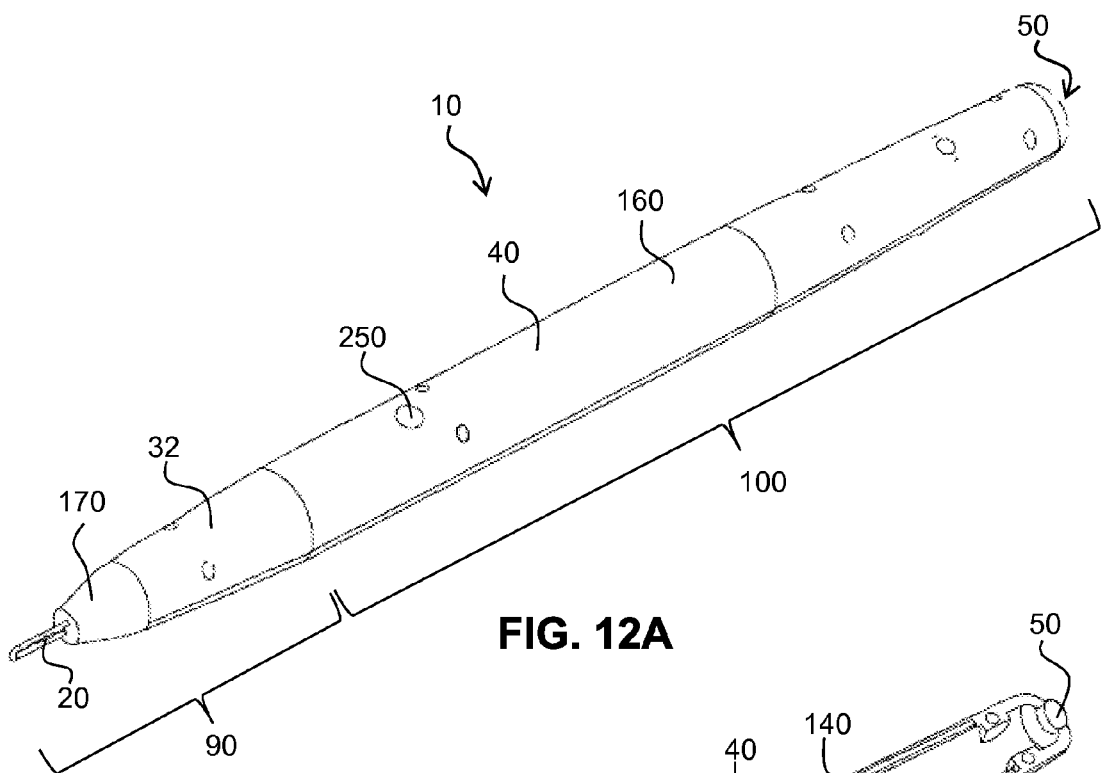
FIG. 12A shows a bottom perspective view of a handpiece with a cooling system.

Turning now to FIG. 12A, a top perspective view of a thermal surgical tool 10 with cooling system is shown. The thermal surgical 10 may include a handpiece 40 which is configured with a cooling system. In some implementations, the handpiece may include a primary section 90 and secondary section 100. The primary section 90 may include a retaining structure 170, such as a cone, active element 20, and housing 32 having an exposed outer surface. The secondary section 100 may include a distal end 50 having a rear exit, a control mechanism 250, such as a push button, for controlling if or when coolant flow exits a front aperture (not shown), or to change the relative distribution of airflow/coolant flow through the primary section 90 and secondary section 100. The secondary section 100 may also include a housing 160 having an exposed outer surface.

Figure 12B:
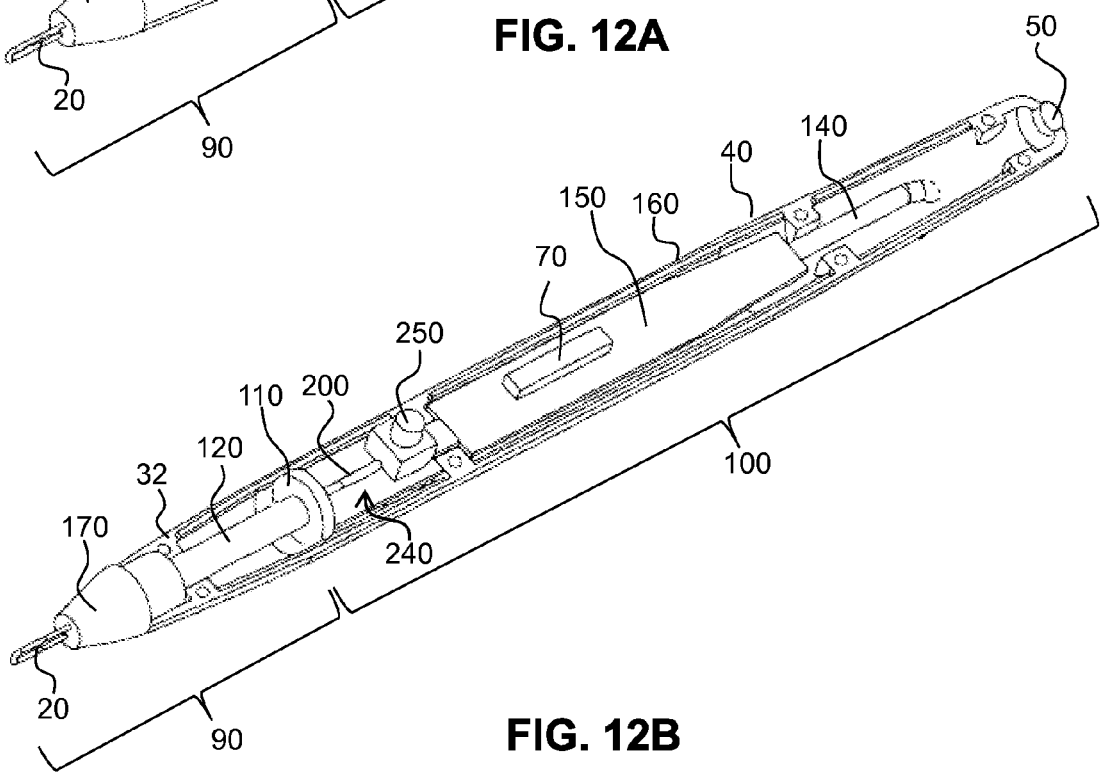
FIG. 12B shows a bottom perspective view of a handpiece with a cooling system having a portion of the case removed.

Turning now to FIG. 12B, a top, perspective view of the bottom of an open handpiece 40 with a cooling system is shown. The discussion herein could be applied to any of FIGS. 8-11C previously discussed. Similar to FIG. 3, a primary section 90 and secondary section 100 may be separated by a divider 110, which may include an O-ring. The primary section 90 of the handpiece 40 may include a thermal element 20, a heat sink 120, a cone 170 and a housing 32. The secondary section 100 may contain a fluid connection site (not shown), a conduit 140, a circuit board 150, internal components 70, a control mechanism 250, a housing 160 and rear exit port 50.

Coolant flow may be encouraged to flow through the majority of the handpiece 40. As described above, the coolant may flow back into the secondary section 100 through a center hole 240 in the divider 110. The coolant flow may then be split between the top and bottom sides of a circuit board 150 by positioning the circuit board 150 to split the center hole 240. Thus both sides of the circuit board 150 may be cooled by the incoming coolant from the primary section 90.

Figure 13A:
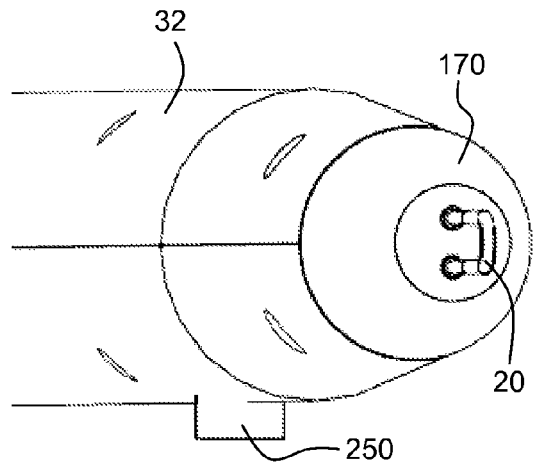
FIG. 13A shows a front perspective view of the tip of a handpiece with a rear vented cooling system.
Figure 13B:
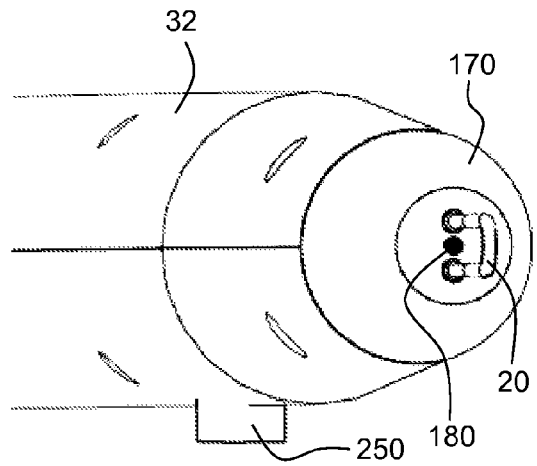
FIG. 13B shows a front perspective view of the tip of a handpiece with a front vented cooling system.

Turning now to FIGS. 13A and 13B, a close-up front perspective view of the handpiece 40 with a cooling system is shown. The handpiece 40 may include a retaining member 170, which may be cone-shaped, a housing 32, a thermal element 20 and control mechanism 250. The control mechanism 250 may control the flow of cooling fluid, or may be used to activate the thermal element 20, or both.

A front vented cooling system may also include one or more front apertures 180 (FIG. 13B), while a rear vented cooling system may not (FIG. 13A). One or more of the front apertures 180 may be adjustable to control when and how much coolant flow will be released therefrom.

Figure 13C:
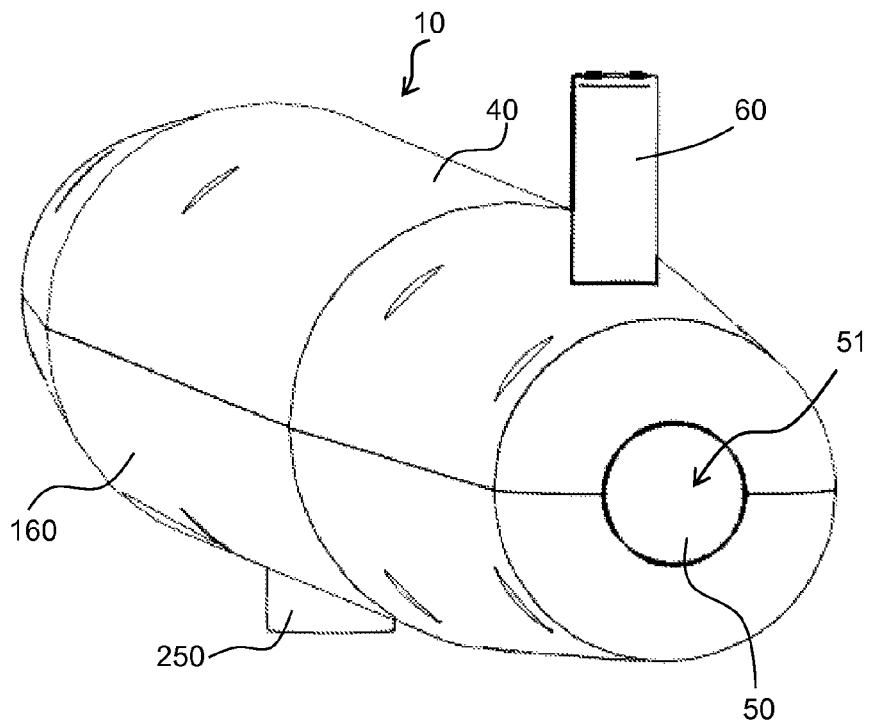
FIG. 13C shows a rear perspective view of the back of a handpiece with a rear vented cooling system.

Turning now to FIG. 13C, a rear perspective view of the back of a handpiece 40 with rear vented cooling system is shown. The housing 160, the fluid connection site 60, the control mechanism 250, and a rear exit aperture or vent 51, and adjustable rear aperture 260 may be seen.

In a rear and front vented handpiece, the airflow may be modified by adjusting the front aperture 180 and/or the rear aperture or vent 51. Adjusting the front aperture 180 and/or the rear aperture or vent 51 may cause the percentage of coolant flow through the other to change. For example, adjusting a front aperture 180 smaller may cause less flow out the front aperture 180 and more flow out the rear aperture or vent 51, when the total flow remains constant. Similarly, adjustment of both the front aperture 180 and the rear aperture 51 may adjust pressure. For example, if both the front aperture 180 and rear aperture 51 are adjusted smaller, the coolant pressure may increase resulting in a stronger flow out of the front aperture 180. This may be advantageous for the front coolant or airflow to disperse liquids. Adjustment of the front aperture 180 and/or the rear aperture 51 (e.g. using a control mechanism) may also include a change to the direction of airflow. For example, the position of the front aperture 180 may be adjustable such that the alignment of the front aperture 180 relative to the thermal element 20 may change thereby adjusting the angle at which coolant is directed from the front aperture 180. Alternatively a separate aperture, such as 182 in FIG. 13B, may be used.

Turning now to FIGS. 14A-C, a side view of internal components of a handpiece and coolant flow patterns are shown. As coolant flow may be difficult to show, three similar views are provided. FIG. 14A shows and labels handpiece components as they might be used in accordance with some aspects of the present invention. FIG. 14B shows coolant flow on top of handpiece components. FIG. 14C shows the coolant flow without the handpiece components. FIGS. 14B and 14C are not labeled due to their complexity. However, the reference designators from FIG. 14A are applicable to both FIGS. 14B and 14C.

Coolant may enter through the fluid connection site 60, travel through conduit 140 to port 230. The coolant may then enter the void 68 in the primary section 90. The coolant is free to circle the outside of the heat sink 120 while it travels to the first end 210 of the heat sink. The cone 170 (not shown in FIGS. 14A-14B) directs the coolant flow in between fins 220 and back down the heat sink 120. Coolant may then exit the heat sink 120 and primary section 90 into the secondary section 100 through the heat sink 120 and a center hole 240 (see FIG. 11A). The coolant may travel to the rear exit 51, while remaining free to surround components in the secondary section 100, such as control mechanism 250, internal components 70 and housing 160 (see FIG. 12B).

While the entrance and exit points are shown according to one aspect of the invention, the convenience of the surgeon should be considered. In one embodiment, a tube may connect to the rear exit 51, such that the coolant may be directed away from the surgeon and patient through the tube. In another embodiment, the fluid connection site 60 and rear exit 51 may be placed at the rear of the handpiece such that both may be served with joined tubing. In another embodiment, the rear exit 51 may be open to vent to the room, i.e. airflow exits directly out of the handpiece 40 and into the room.

Figure 15A:
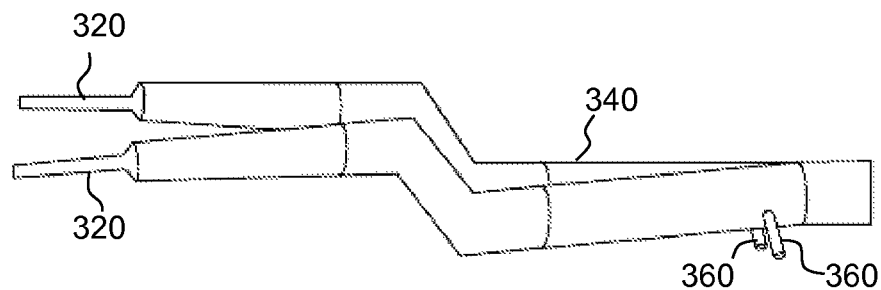
FIG. 15A shows a side view of cooled forceps.

Turning now to FIGS. 15A-D, other cooled surgical instruments are shown that may include a cooling system as described above. While the aspects of the invention have been discussed principally with respect to a surgical cutting tool, the aspects can be used with multiple other types of tools. FIG. 15A shows cooled surgical forceps 340 with one or more fluid connection sites or ports 360 so that each tine 320 can receive active cooling. Although in some cases, it may be desirable to only cool one tine. Thus, a heated forceps, including but not limited to forceps having ferromagnetic tines, may be actively cooled.

Figure 15B:
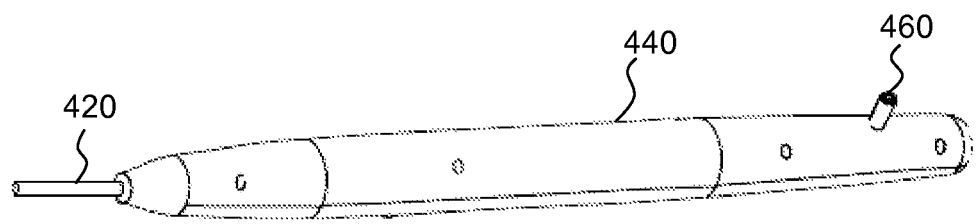
FIG. 15B shows a side view of a cooled ultrasound tool.

FIG. 15B shows a cooled surgical ultrasonic surgical handpiece 440. The handpiece 440 includes a fluid connection site or port 460 which can be used to cool the interior components of the handpiece as the ultrasonic element 420 is used, to thereby keep the handpiece comfortable to use.

Figure 15C:
FIG. 15C shows a side view of a cooled monopolar handpiece.

FIG. 15C shows a cooled monopolar handpiece 540 with a fluid connection site or port 560 for cooling fluid to keep the handpiece cool while electricity is released from the electrosurgical element 520.

Figure 15D:
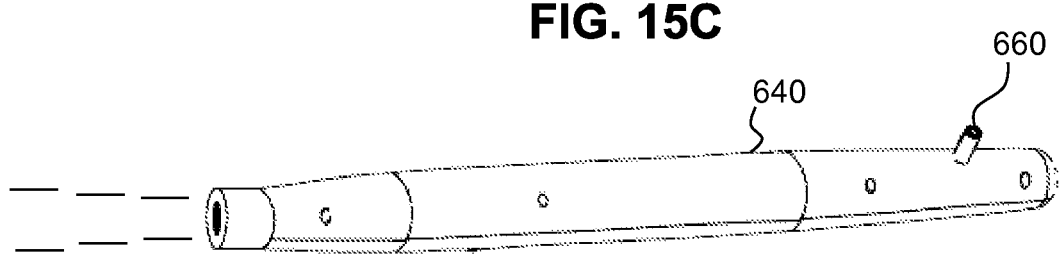
FIG. 15D shows a side view of a cooled catheter.

FIG. 15D shows a cooled catheter with a fluid connection site port 660 on the handpiece to cool the catheter during use. Cooling may occur in a manner consistent with the discussion of the handpieces 40a-40d (FIGS. 10A-10D) discussed above.

Figure 16A:
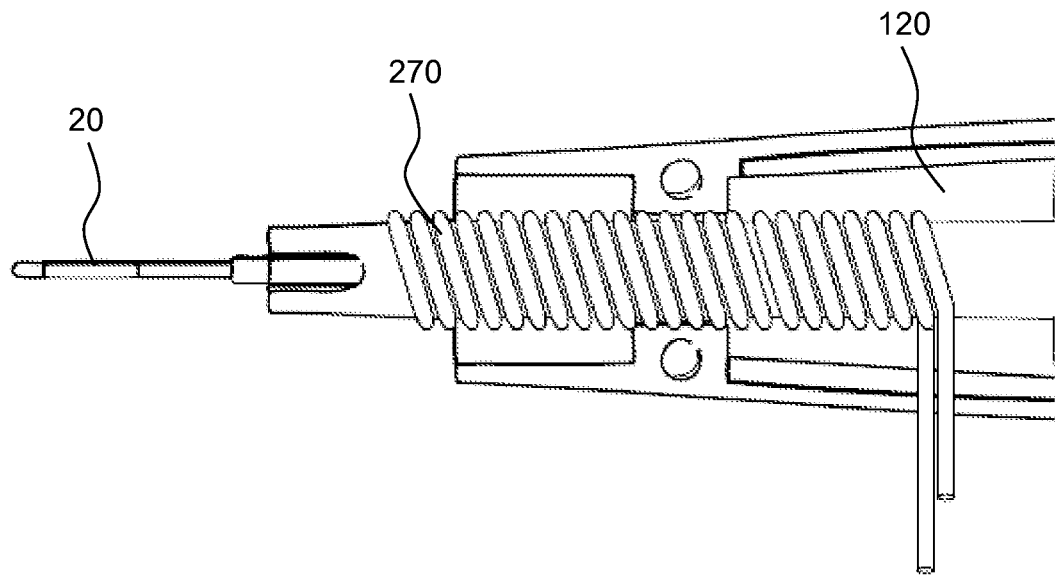
FIG. 16A shows a top view of an open tip with coil cooling.

Turning now to FIG. 16A, a top, open view of the proximal end of a thermal surgical tool with a coil cooling is shown. In some cases, it may be desirable to add a coil 270 around the heat sink 120 to further cool the heat sink 120. This may be done in conjunction with the cooling system described above or separately for the primary section 90. Ambient air, other gasses or cooling liquid may be run through the coil 270, such that the flow causes heat to transfer from the heat sink 120 to the coil 270 and then to the air or fluid within the coil. If sufficiently hot, the system may be set up with a condenser. Otherwise, the air or liquid may be cooled outside the handpiece 40. While the coil has been shown to enter and exit through the housing of the primary section, it should be recognized that the coil entrance and exit may be instead crafted to enter and exit elsewhere from the handpieces, such as the rear of the handpiece.

Figure 16B:
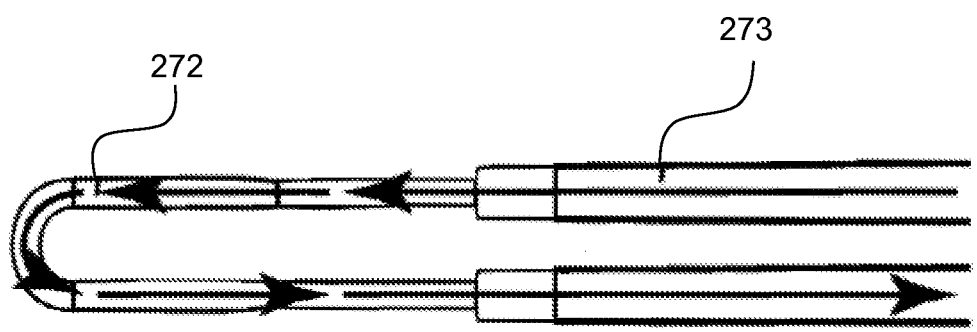
FIG. 16B shows a side view of a tip with hollow tip cooling.

Turning now to FIG. 16B, a side view of a hollow thermal element is shown. According to one aspect of the invention, a handpiece may include a hollow thermal element 272. It may also include hollow electrical connections, such as hollow conductive stand-offs 273. The hollow thermal element 272 (which could be element 20 in the previous figures) and hollow electrical connections 273 may be fluidly connected so that fluid may mass through the hollow areas. This would allow the heat to transfer to the cooling fluid, which may be transported away from the tip for heat removal.

According to one aspect of the invention, a saline solution may originate from an external pump fluidly connected to the handpiece. The saline is pumped through the handpiece into the electrical connections 273 and the thermal element 272, and back out to the external pump. The heat contained in the liquid may be removed after the exit from the handpiece, such as by a heat sink.

Figure 17:
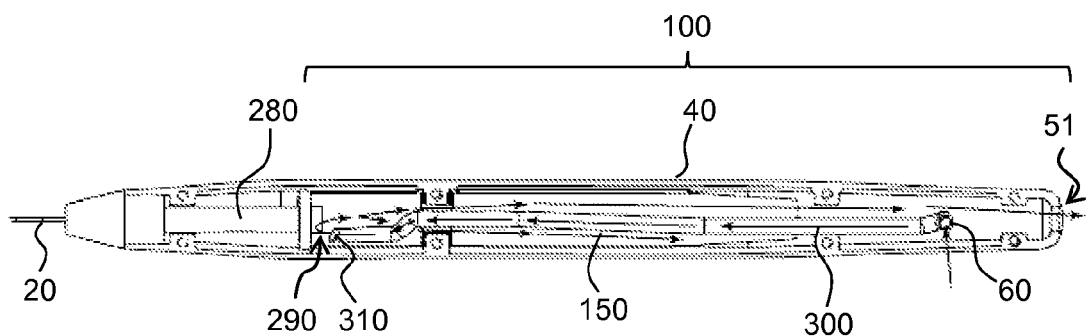
FIG. 17 shows a top view of an open handpiece with a heat pipe cooling system.

Turning now to FIG. 17, a top view of an open handpiece with a heat pipe cooling system is shown. Instead of a hollow heat sink, the primary section may contain a heat pipe 280 between the thermal element 20 and the secondary section 100, or along other locations of the handpiece. A second end 290 of the heat pipe 280 may actually extend into the secondary section 100 such that active cooling of the secondary section 100 may cool the second section of the heat pipe. Thus, the primary section may be cooled with a passive heat pipe that is actively cooled in the secondary section.

In the example shown, the coolant flow may still cool the primary section via the heat pipe 280. Coolant may be introduced into the fluid connection site 60 and flow through conduit 300. The conduit 300 releases the coolant flow at heat pipe exit 310, such that the coolant flow may blow against the heat pipe 280 at its second end 290. The coolant may then flow through the secondary section 100 and over structures such as the circuit board 150 to the rear exit 51.

While heat pipe cooling has been discussed, it should be recognized that there are different forms of heat pipes, each with its own advantage. For example, a loop heat pipe may be used in situations where distances, large heat transfer and/or gravitational orientation are at issue. A loop heat pipe may present an advantage in an unfavorable evaporator over condenser position, compared with conventional heat pipes.

Figure 18:
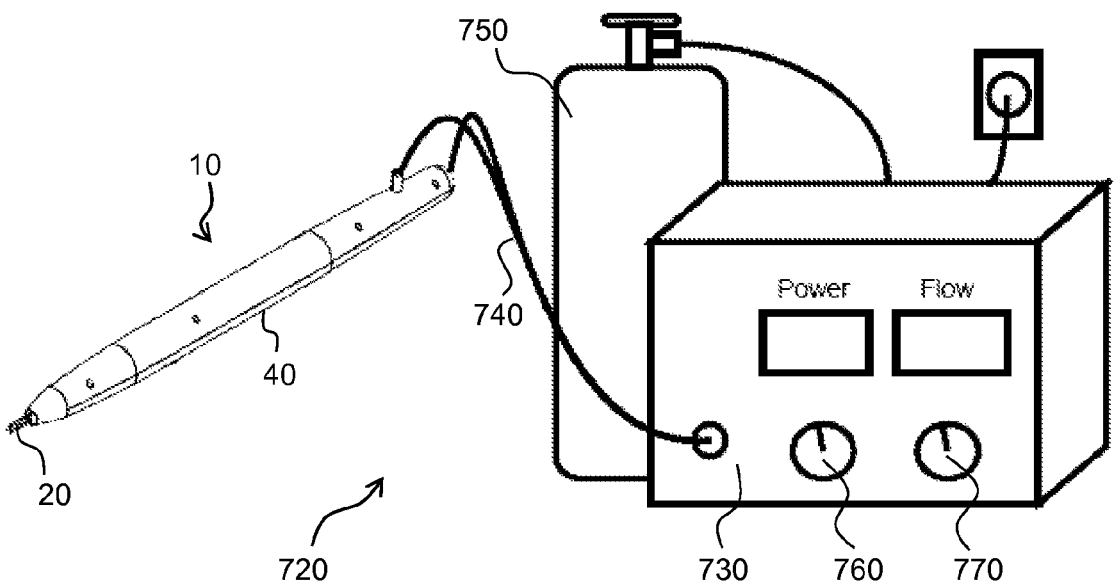
FIG. 18 shows a surgical system with a cooled handpiece.

Turning now to FIG. 18, a surgical system 720 with cooled handpiece 40 is shown. The system may include a handpiece 40 connected or in communication with a control unit 730. According to one aspect of the invention, the handpiece 40 is connected by a cable 740 that includes coolant flow and electrical signals. The coolant flow may be sourced from a compressor or pump that is internal to the system 720, or an external source, such as a tank 750 connected to the control unit 730, such as a compressed carbon dioxide tank. The control unit 730 may contain controls for various functions of the handpiece 40, including a power control 760 and flow control 770.

The control unit 730 may provide the coolant flow and electrical systems needed by the handpiece. In the case of a ferromagnetic covered conductor, solid ferromagnetic wire, monopolar, bipolar, ultrasonic, heated blade or other surgical modalities, the control unit 730 may provide coolant flow, power and/or waveforms for use by the thermal element 20. The control unit 730 may be adjusted to provide initial settings, which may be further directed by the handpiece.

According to another aspect of the invention, the control system may monitor the connection with the handpiece 40. If a problem is detected, the system may alert the surgeon, such as by an alarm, and/or move toward a safe shutdown of the system. This monitoring may include coolant flow speed, coolant pressure, moisture, standing wave ratio, reflected signals, or other information sent back by the handpiece 40. In the case of a tank 750, coolant flow may be more easily adjusted. In the case of a compressor or pump, air speed or pressure may be more easily measured.

The control system may also monitor the handpiece 40 temperature and adjust the coolant flow accordingly. Thus, the system 720 may cause a greater volume of coolant to flow when the handpiece 40 is actively used, and less when the handpiece is cooling down or in a state of less active use.

Figure 19:
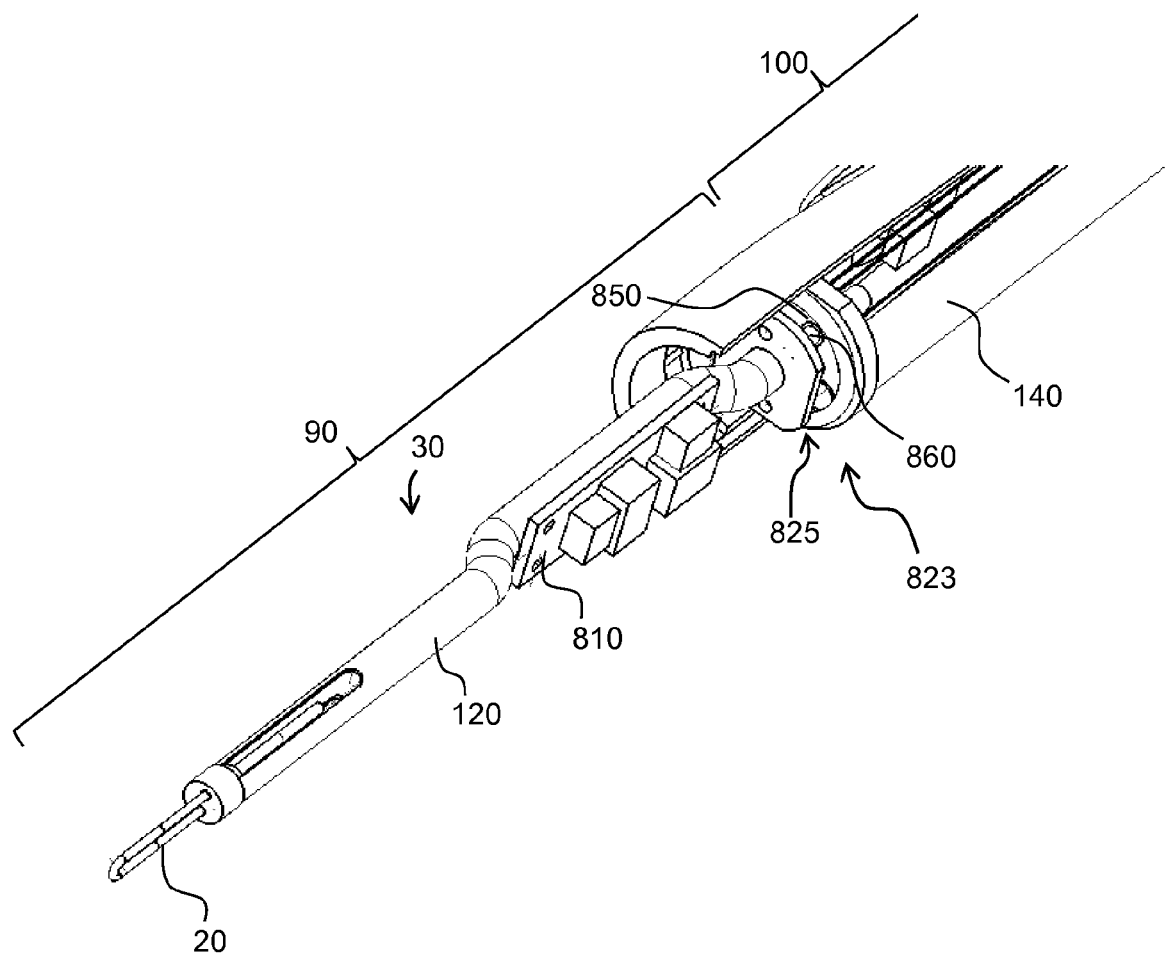
FIG. 19 shows a perspective, open view of a removable tip with cooling.

Turning now to FIG. 19, a perspective view of a removable tip 30 for a handpiece 40 with active cooling is shown. The removable tip 30 may be coextensive with and may include similar structures as the primary section 90 discussed above. The removable tip 30 may include an impedance matching circuit 810 within the removable tip and a joint 823 at which the removable tip may disconnect from the secondary section 100. The impedance matching circuit 810 may be configured to aid in the efficiency of power transfer from a power source to the thermal element 20. With the addition of an impedance matching circuit 810 in a removable tip 30, heat sink 120 may be routed around the circuit 810. The joint 823 may include a straight cut 825 to allow coolant to flow through the joint into the tip. Similarly to the descriptions above, the air may circulate around the tip 30 and back through the heat sink 120.

Figure 20:
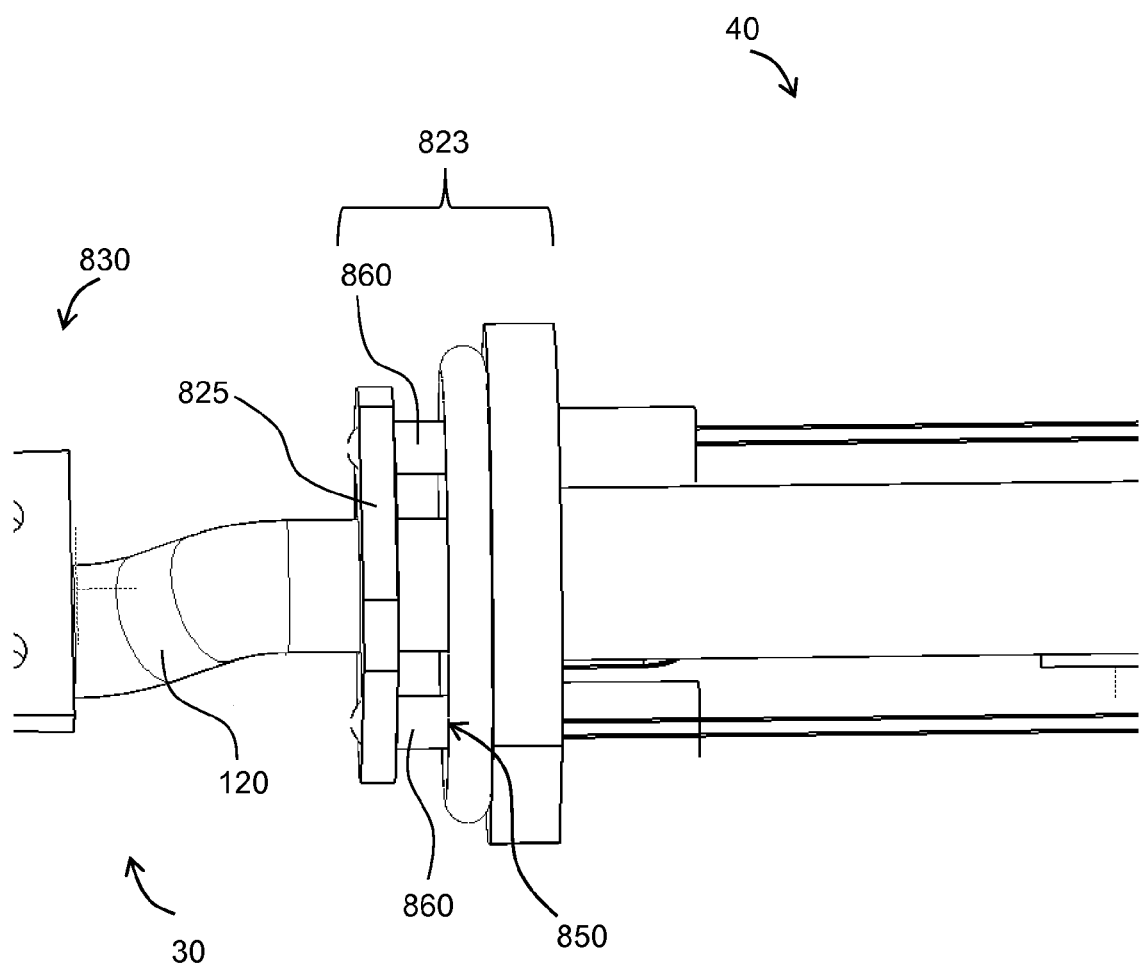
FIG. 20 shows a close-up view of the joint of a removable tip with cooling.

Turning now to FIG. 20, a close-up of the joint 823 of a removable tip 430 with active cooling is shown. A case interlock may be used to attach the tip body 430 or primary section 90 to the housing of the secondary section 100, such as a push in and twist action to lock, or the internal components of the tip body may connect directly to the internal components of the secondary section 100 via tabs, snaps, engagement arms, threads or interlocking structures, etc. Electrical power may be transferred through spring loaded connectors 860 on one side of the joint and receiving pads 850 on the other side of the joint 823 or by other suitable connectors. Coolant may be transferred in through a conduit 140 (FIG. 19) into the joint. The coolant may flow around the joint through a cut out 825, such as a straight cut, into the removable tip 30. Coolant may return through heat sink 120 back into the secondary section 100 of the handpiece 40. In some cases as described above, the coolant may be directed out of the tip 30 as well, for example, toward the thermal element 20.

Figure 21:
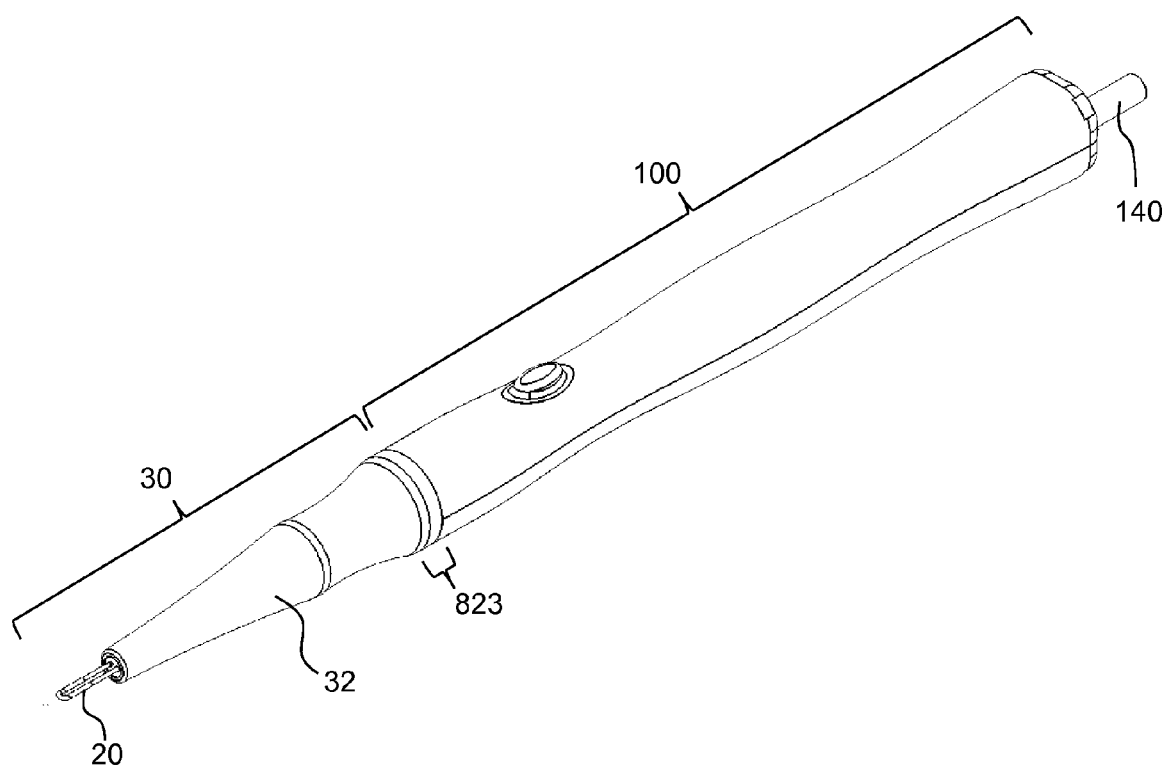
FIG. 21 shows a perspective view of a removable tip handpiece with cooling.

Turning now to FIG. 21, there is shown a perspective view of a handpiece 40 with a removable tip 30. The handpiece 40 may include a thermal element 20, a removable tip 30, a housing 160 and a control mechanism 250. Air or other coolant may flow in through a tube or conduit 140 into the handpiece 40. The coolant may be carried by the conduit 140 through the secondary section 100 into the removable tip 430 (essentially a primary section) through joint 823. Coolant may then be directed up through the tip, cooling the tip housing 160. The coolant may then be directed out of the tip onto the active element 20 and/or return through a heat sink 120 which directs heat away from the active element 20. Rear-traveling air may then travel through the secondary section 100 cooling any remaining components and exit the handpiece 40.

Figure 22:
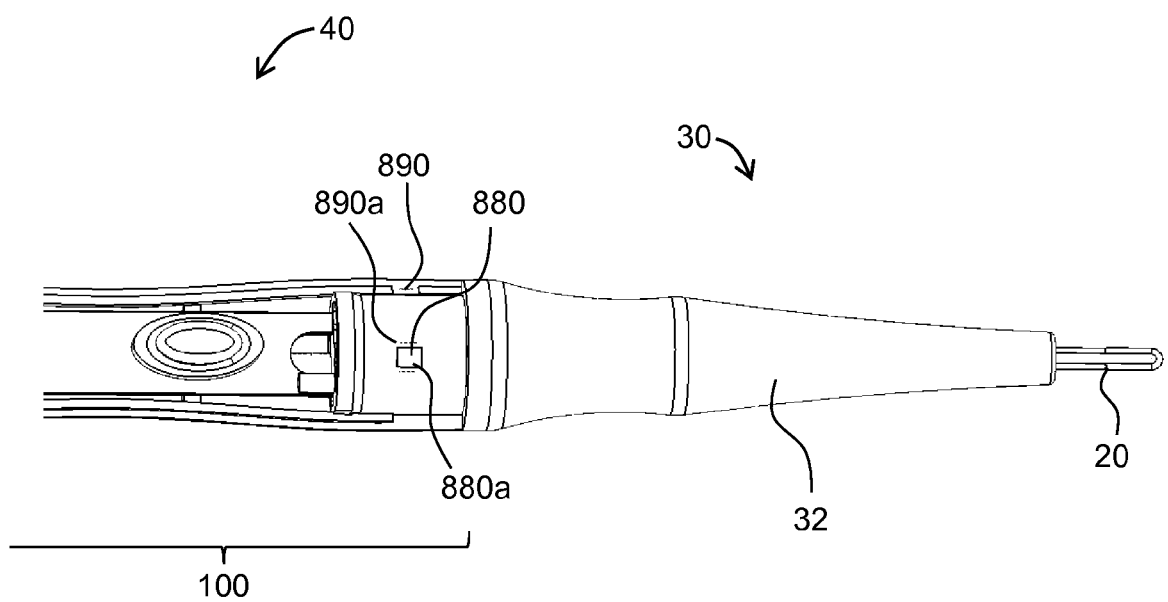
FIG. 22 shows a top view of a removable tip handpiece with cooling with a top case portion removed.

Turning now to FIG. 22, there is shown a top view of a removable tip handpiece 40 wherein the top housing portion of the handpiece is removed. The tip housing 32 may include a locking structure 880 that interfaces with a receptacle 890 in the secondary section 100. This may be, for example, an arm that extends and has a projection 880*a* which nests in a void or hole 890*a* in the receptacle. Pressing the projection 880*a* may release the engagement and allow the tip 30 to be removed. It will be appreciated that a wide variety of releasable attachments can be used to removably secure the tip 30 to the secondary section 100. It will also be appreciated that such an attachment/detachment system can be used on the previously discussed handpieces and other tools.

When coolant flow is discussed in later figures, it should be recognized that flow may be constrained by the tip housing 32. Thus, the tip housing 32 may serve as a conduit channeling air flow for at least a portion of the removable tip 30.

Figure 23:
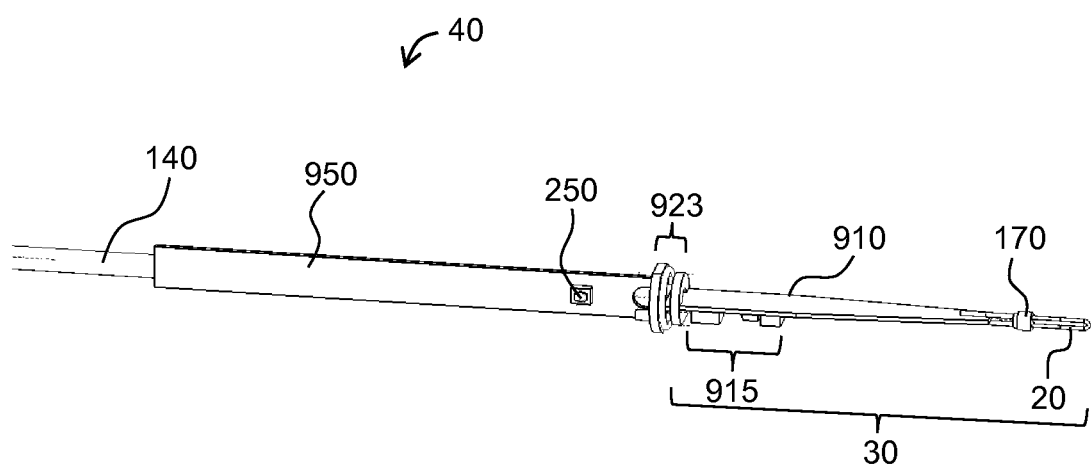
FIG. 23 shows a perspective view of a removable tip handpiece with cooling with the case and tip cover removed.

Turning now to FIG. 23, there is shown a perspective view of a handpiece 40 with a removable tip. The handpiece 40 may include a conduit 140, a main board 950, a control mechanism 250, joint 923 and removable tip 30. The removable tip 30 may include a tip board 910, retaining structure 170, and thermal element 20.

The tip board 910 may include functions to improve power transfer and heat transfer. The tip board 910 may house an impedance matching circuit 915 to aid in power transfer from a power source to the thermal element 20. The tip board 910 may also act as a heat sink to pull heat away from the thermal element 20. For example, the tip board 910 may include a heat conductive substrate, such as copper, that may act to receive thermal energy from the thermal element 20.

The main board 950 may provide functionality to the handpiece 40. The functionality may include activation and adjustments, such as through a pushbutton or slider. The main board 950 may also contain power transfer circuits to aid in power transfer to the thermal element 20 and/or tip 30.

Figure 24:
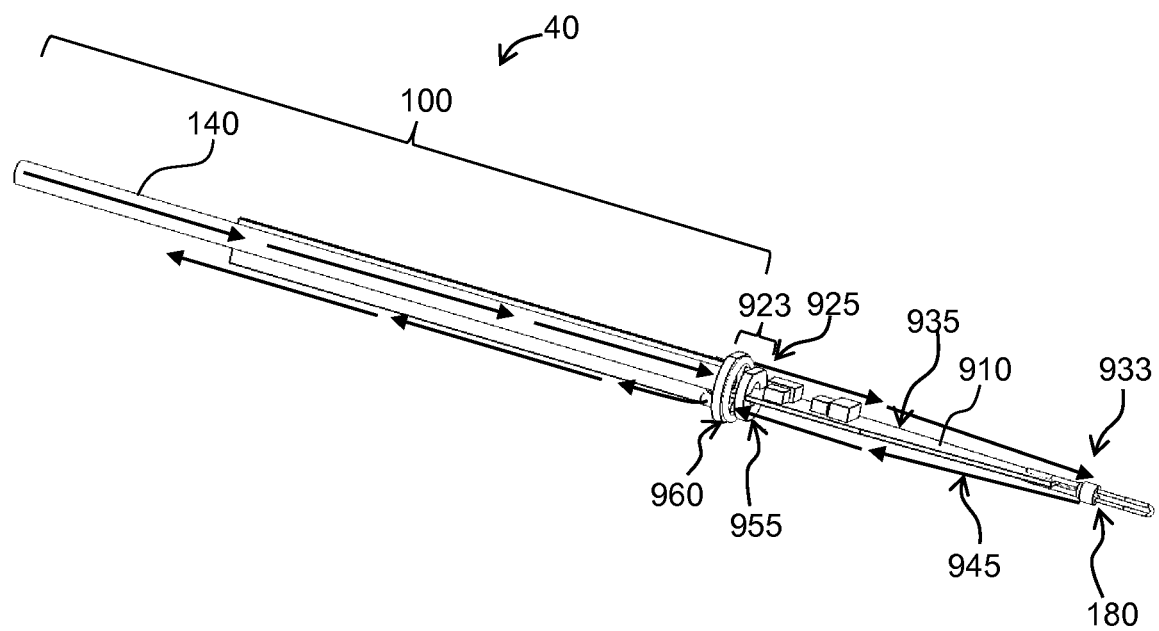
FIG. 24 shows a perspective view of the interior of a removable tip handpiece with coolant flow diagram.

Turning now to FIG. 24, a perspective view of a handpiece 40 having a removal tip with a coolant flow diagram is shown. While numbered separately, it will be appreciated that any of the structures shown herein could be incorporated into some or all of the previous embodiments. Coolant may enter the handpiece 40 through conduit 140. The conduit 140 may continue through the secondary section 100 and deliver the air to the joint 923. Joint 923 may force the incoming air through a cut out 925 leading to a first side 935 of the tip board 910. Constrained by the tip housing 32, coolant may travel down the first side 935 of the tip board 910. Near the proximal end 933 of the handpiece 40 the coolant may be allowed through a forward aperture 180 and/or directed around the proximal end 933 to pass along a second side 945 of the tip board 910. At the joint end 955 of the tip board 910, a joint aperture 960 may allow air from the second side 945 to pass into the secondary section 100. Coolant may flow through the secondary section 100 over the main board and out of the handpiece 40.

Figure 25:
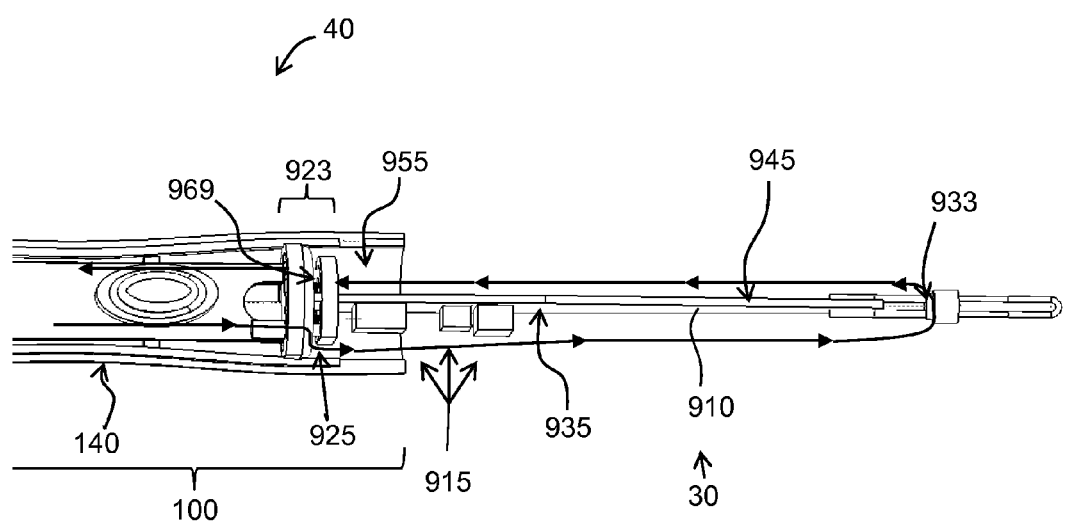
FIG. 25 shows a top view of the interior of a removable tip handpiece with cooling with coolant flow diagram.

Turning now to FIG. 25, a coolant flow diagram is shown in connection with a top, close-up view of a handpiece 40 having a removable tip 930. Coolant may flow through the joint 923 and into the removable tip-30 through a cut out 925. The coolant may then flow across an impedance matching circuit 915 and across a first side 935 of the tip board 910. Coolant may then flow around the tip board active element end 933 and cool the retaining structure 170 (not shown) as well. The coolant may continue along the second side 945 of the tip board 910 and pass through a joint aperture 960 into the secondary section 100.

Figure 26:
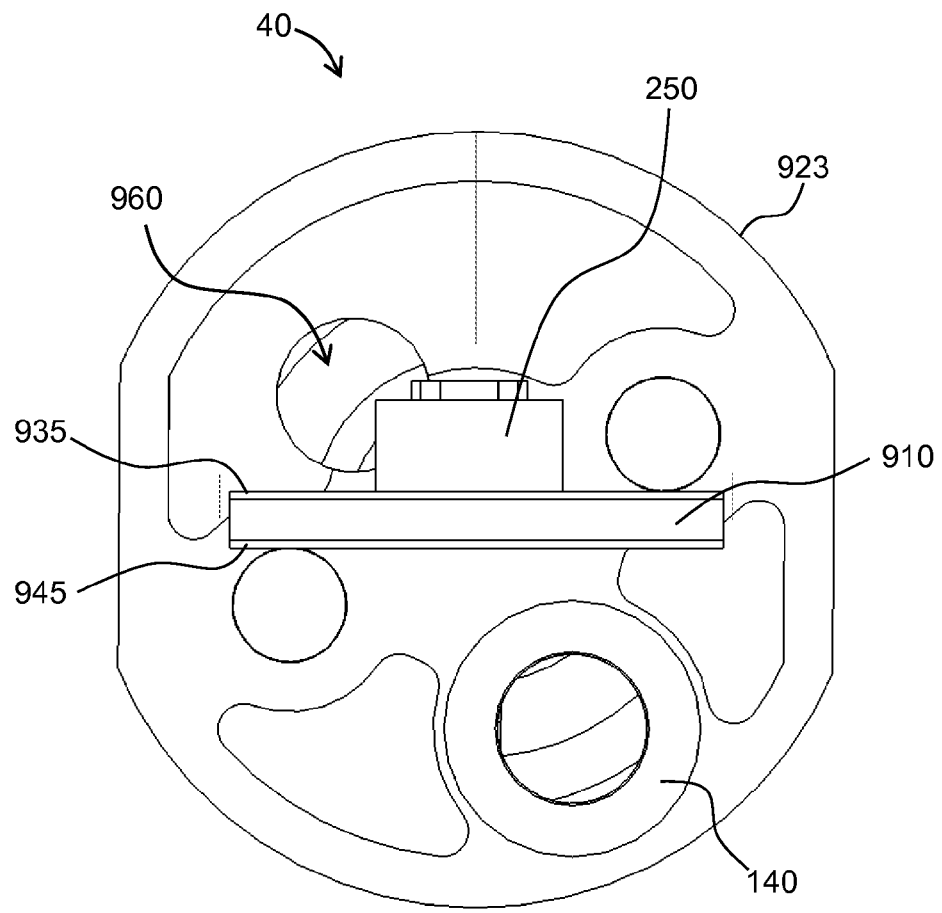
FIG. 26 shows a rear view of a removable tip of a handpiece with cooling without a case.

Turning now to FIG. 26, there is shown a rear view of a handpiece portion 40 with the housing removed. With the housing removed, the conduit 140, main board 910, control mechanism 250 and joint aperture 960 may be observed.

Figure 27:
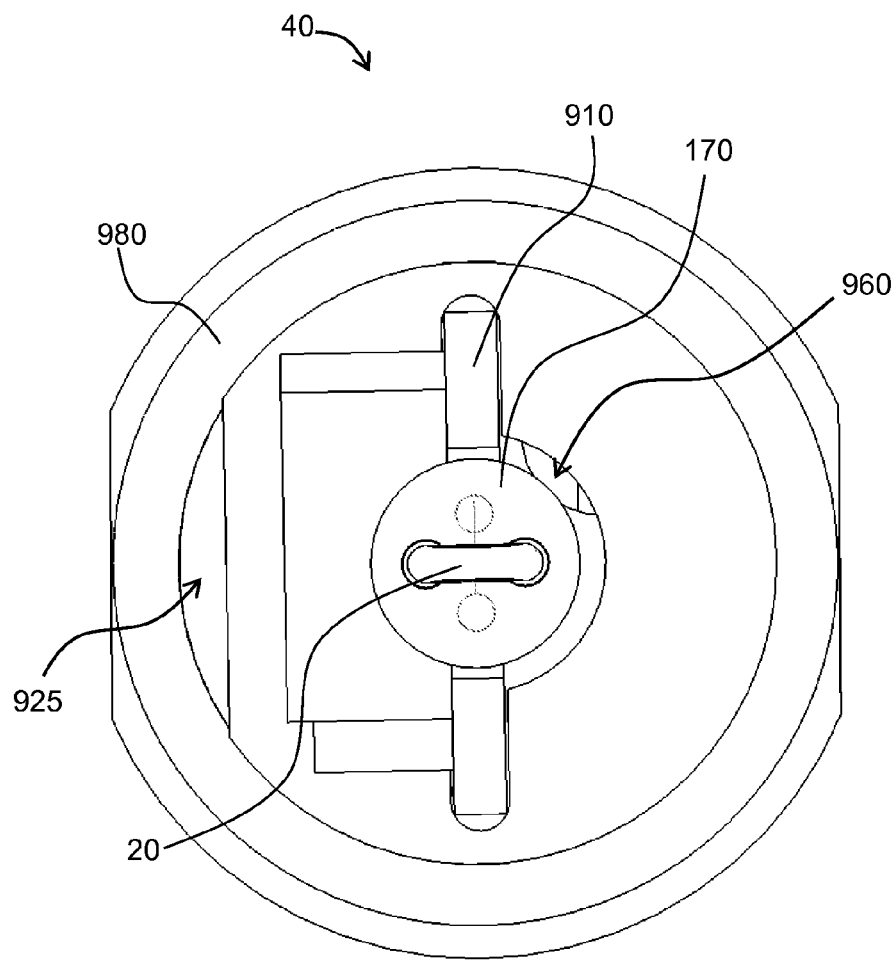
FIG. 27 shows a front view of a removable tip handpiece with cooling without a case.

Turning now to FIG. 27, there is shown a front view of a handpiece 40 having a removable tip without the tip housing. With the tip housing (not show) removed, the thermal element 20, retaining structure 170, tip board 910, sealing ring 980, cut out 925, and joint aperture 960 may be seen. The sealing ring may be disposed on the tip housing 970 (not show) to ensure consistent airflow through the joint 923 and reduce or eliminate cooling leakage through the joint. According to one aspect of the invention, the joint aperture 960 only allows airflow from one side (either the first side 935 or second side 945) which is opposite the conduit 140 so that the airflow is on a return path along the tip board 910 into the secondary section 100.

Figure 28:
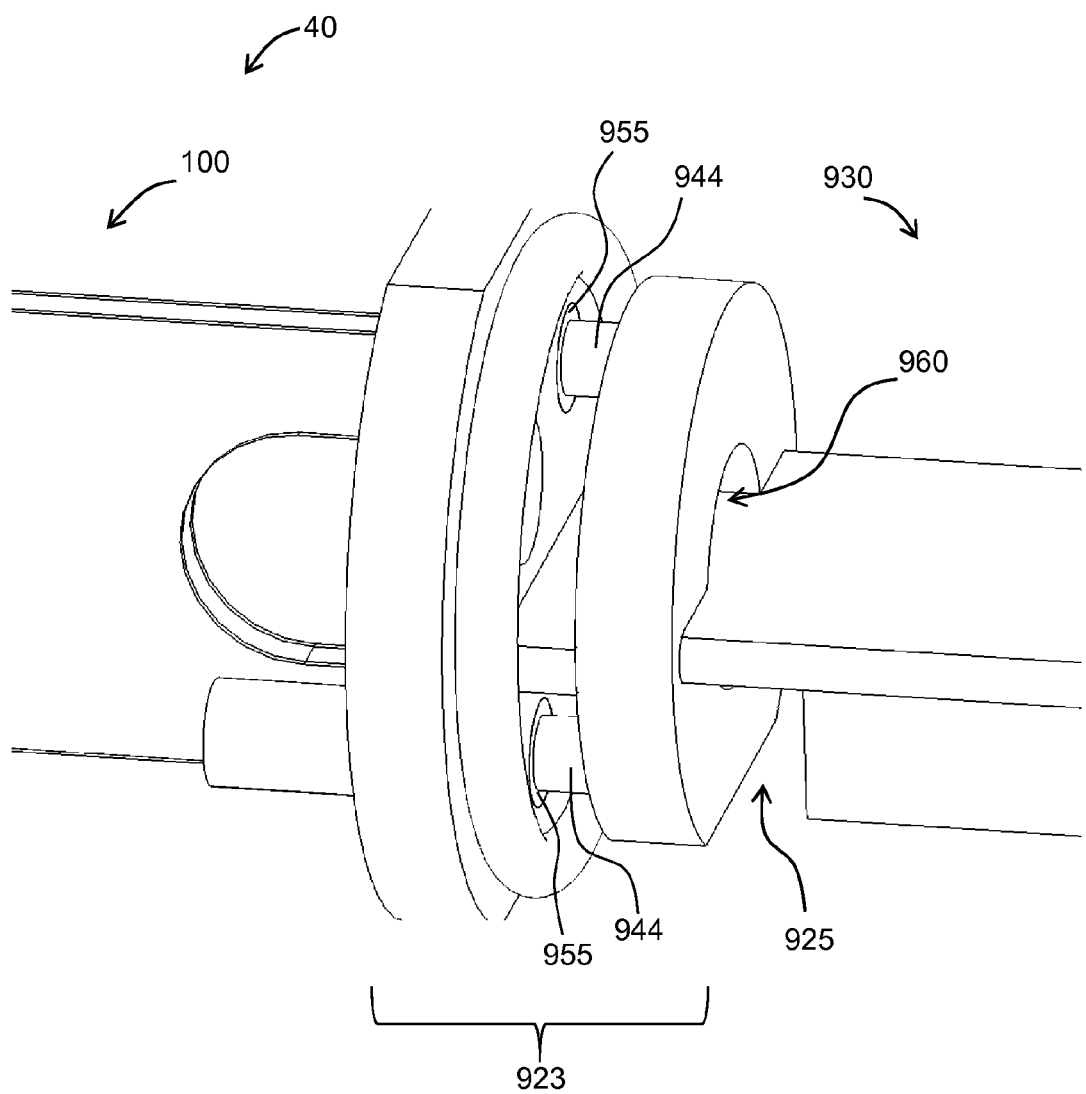
FIG. 28 shows a close-up view of a joint of a removable tip handpiece with cooling as shown in FIG. 25.

Turning now to FIG. 28, there is shown a close-up of a joint 923 of a handpiece 40 with a removable tip 930. Spring loaded connectors 944 may be used to allow power to flow from the secondary section 100 to the removable tip 30. With spring loaded connectors 944 and corresponding receiving pads 955, the joint may be configured to allow the surgeon to twist and adjust the removable tip. The cut out 925 and joint aperture 960 may also be seen.

It will be appreciated that a variety of connectors can be used to connect the tip 30 to the secondary section 100 and to connect the electrical components. These may include snap fits, tongue and groove engagements, threads, coaxial connectors, twist-lock engagements, etc. Additionally, it will be appreciated that any of the structures discussed with respect to FIGS. 19 through 28 could be incorporated into any of the other embodiments of the invention discussed herein and vice-versa.

Figure 29:
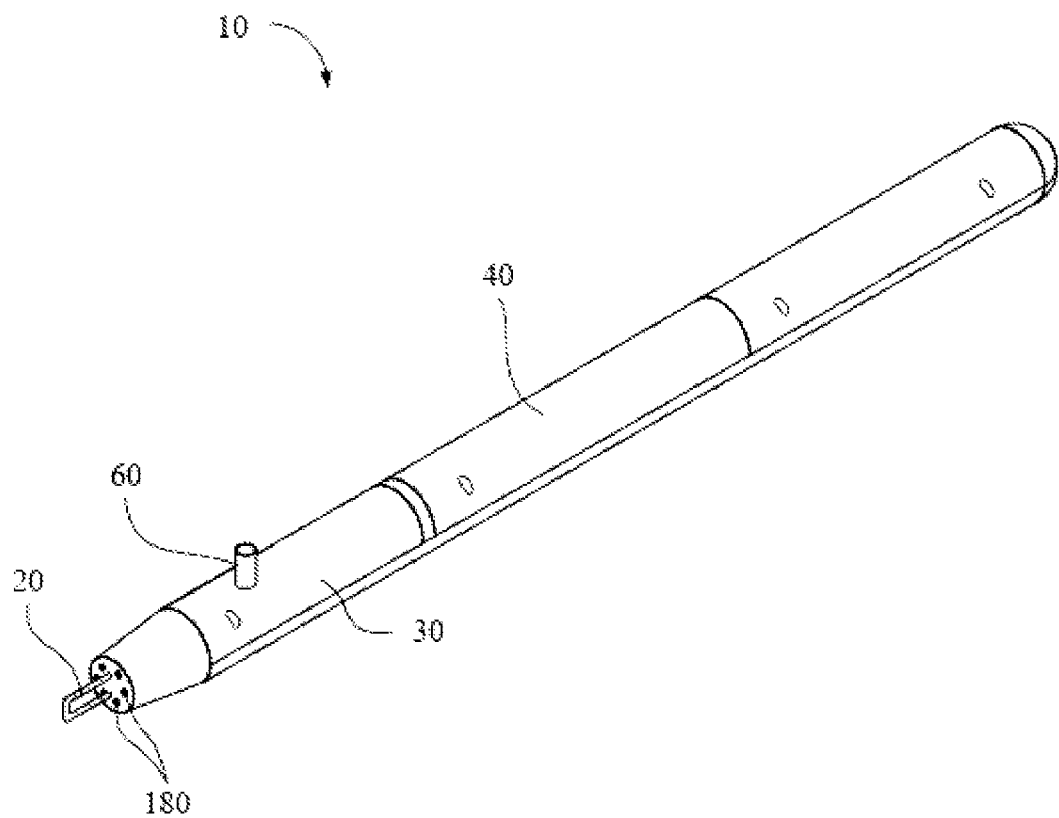
FIG. 29 shows a perspective view of a heated surgical instrument with a cooling system made according to principles of the present invention.

Turning now to FIG. 29, a perspective view of a heated surgical instrument 10 with a fluid cooling system is shown. The heated surgical instrument 10 may be an electrosurgical instrument with an active thermal element or other surgical element 20, such as a conductor with a ferromagnetic coating. In some medical applications, such as the ablation or cutting of tissue, the thermal element 20 can be driven to several hundred degrees Centigrade. However, during other applications, such as vascular endothelial welding, it may be desirable to operate the thermal element 20 at much lower temperatures.

An undesired result may occur in electrosurgical applications if the thermal element 20 exceeds a certain temperature during a specific procedure. Thus, it may be important to provide a heated surgical instrument with a fluid cooling system to ensure that the thermal element 20 stays within an optimal temperature range. Heated surgical instrument 10 may include a tip 30 with a fluid connection site or port 60 for receiving a cooling fluid. Fluid that is received by the fluid connection site or port 60 may be delivered to thermal element 20, or to structures adjacent to thermal element 20 through a void or conduit located inside tip 30, or by a channel, etc. Examples of such structures are discussed with respect to previous figures and any of those structures could be used herein.

Fluid may pass through the void or conduit and exit through one or more apertures or ports 180 and pass over the thermal element 20. As was mentioned previously, the cooling fluid may be air or some other gas. Passage of cooling fluid over the thermal element 20 reduces the temperature of the element. In accordance with one aspect of the invention, however, the cooling fluid may also be used to cool tissue which has come into contact with the surgical element 20 to thereby minimize damage to the tissue.

Figure 30:
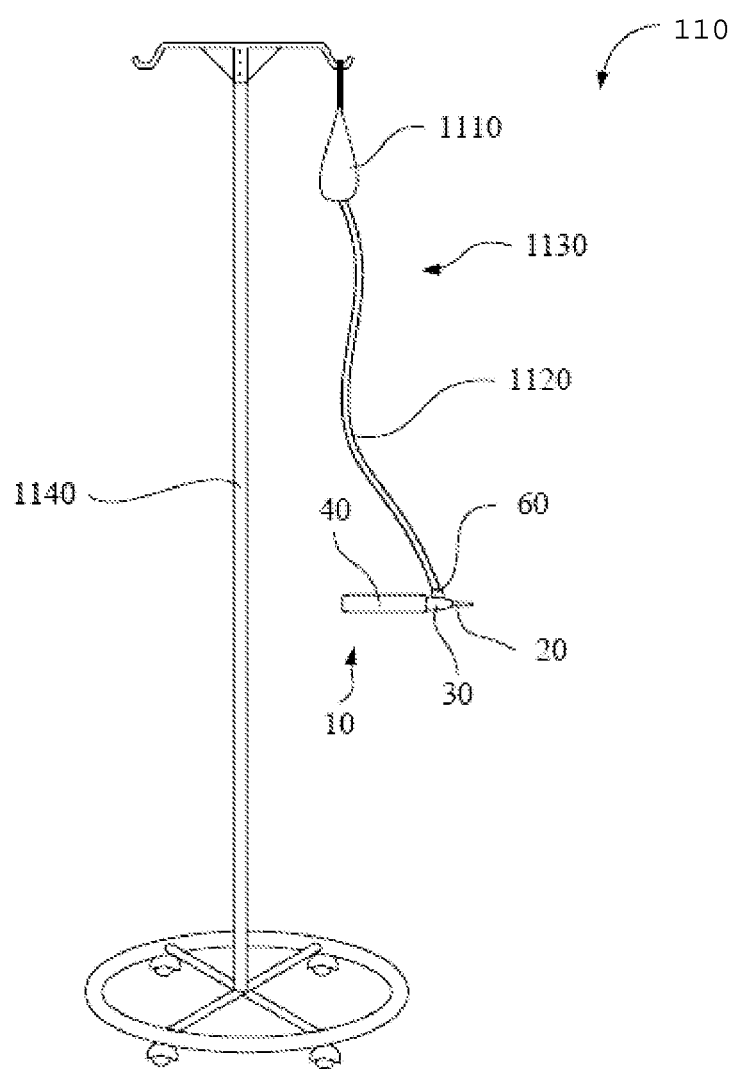
FIG. 30 shows a surgical system with a heated surgical instrument in communication with a fluid drip line in accordance with the present invention.

Turning now to FIG. 30, there is shown a surgical system 110 with a fluid cooled heated surgical instrument 10. The system may include a handpiece 40 connected to or in communication with a fluid drip line 1130. Fluid drip line 1130 may include a bag 1110 of fluid, such as saline, water, etc., hung from a pole 1140 and tubing 1120. Fluid from bag 1110 flows through tubing 1120 to the hand piece 40. It may enter the secondary section of the handpiece 40 as discussed above, or it may enter the tip 30 of handpiece 40 similar to FIG. 29. The fluid may be dispensed on or adjacent thermal element 20. It will be appreciated that handpiece 40 may include interchangeable tips 30 with different surgical/thermal elements, to thereby enable a surgeon to select the desired element 20 for a given procedure.

The flow of fluid to tip 30 may be controlled by adjusting the height at which bag 1110 is hung relative the height of a surgical field. For example, if a lower rate of fluid flow to tip 30 is desired, pole 1140 may be adjusted downward so that bag 1110 is at lower position relative to a surgical field thereby reducing the gravity flow of fluid to tip 30.

Alternatively, a higher rate of fluid flow to tip 30 may be achieved by increasing the height at which bag 1110 is hung relative to a surgical field. A higher rate of fluid flow may be desirable, for example, when a larger thermal element 20 is necessary for a given procedure, such as when a ferromagnetic element having a diameter of 1 mm or larger may be used to retract muscle from a patient's spine while achieving hemostasis.

A higher flow rate may also be desirable when a surgeon also wants to irrigate a surgical field while ensuring that thermal element 20 remains within an appropriate temperature range. By increasing the flow rate of fluid to tip 30, only a portion of the fluid may evaporate off of thermal element 20 while the remaining portion is directed into the surgical field where thermal element 20 is being used.

In accordance with one aspect of the invention, all or a portion of cooling fluid may be directed to irrigating the surgical field to thereby quench the tissue or other material at or adjacent the thermal element's 20 contact point with the tissue or other material. Contemporaneous quenching of the tissue or other material while the heated surgical instrument 1010 is being used for a procedure may lead to improved outcomes and more rapid post-surgery recovery times as the cooling fluid will withdraw heat from the tissue and may prevent damage to tissue other than tissue immediately adjacent the incision, etc.

Figure 31:
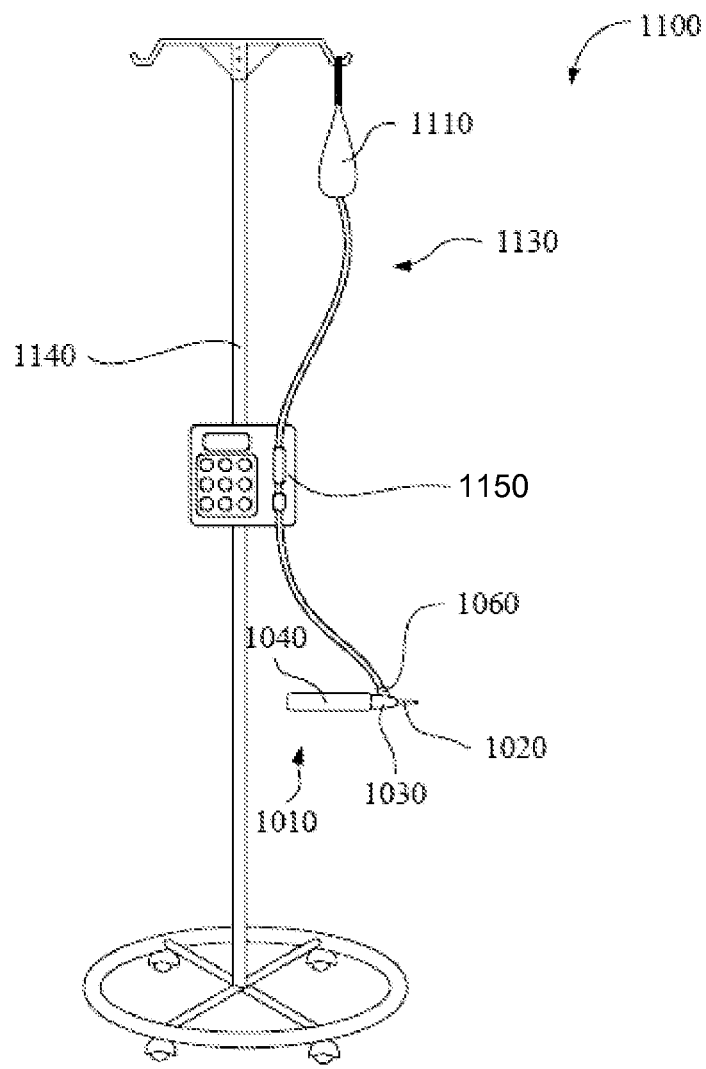
FIG. 31 shows a surgical system with a heated surgical instrument in communication with a fluid drip line regulated by a pump.

Turning now to FIG. 31, there is shown another surgical system 1100 with a fluid cooled heated surgical instrument 10. The surgical system 1100 of FIG. 31 may also include a handpiece 40 which is connected by a fluid connection site 60 to, or disposed in communication with, a fluid drip line 1130. The fluid flow rate to tip 30 may be controlled by a pump 1150, such as a peristaltic pump. Use of pump 1150 to control the rate of fluid flow may be advantageous in that a more precise flow rate may be achieved.

Figure 32:
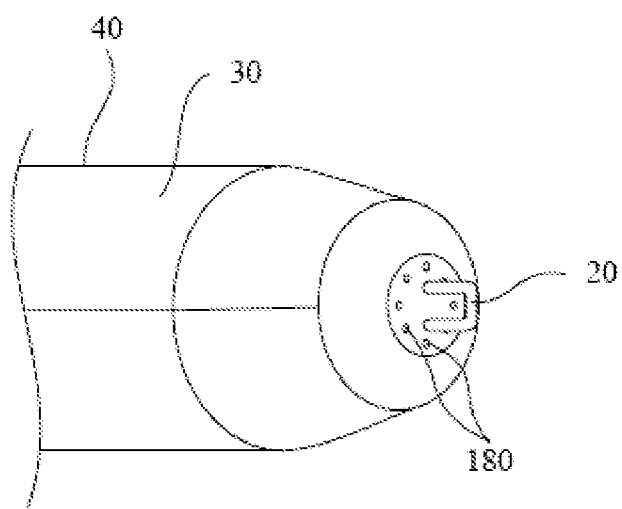
FIG. 32 shows a fragmented, perspective view of a tip for a heated surgical instrument in accordance with one aspect of the present invention.
Figure 33:
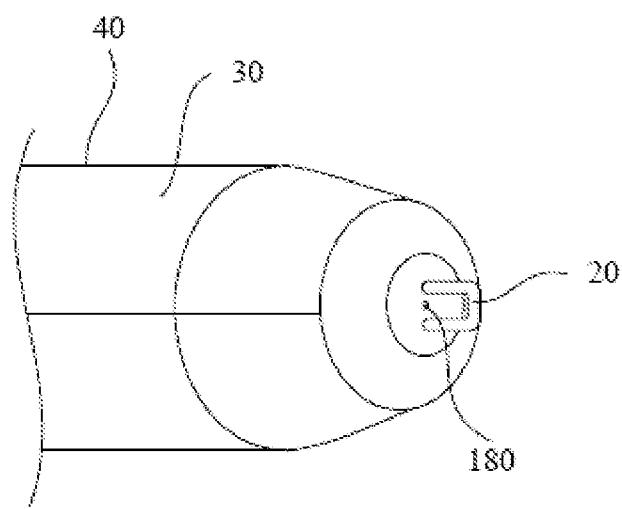
FIG. 33 shows a fragmented, perspective view of a tip for a heated surgical instrument with a single irrigation port.

Turning to FIGS. 32 and 33, there are shown fragmented, perspective views of tips 30 for a heated surgical instrument made according to principles of the present invention. As depicted in FIGS. 32 and 33, the tip 30 may include one port or aperture 180 (FIG. 33) or a plurality of ports 180 (FIG. 32). It will be appreciated that the number of ports 180 included in the tip 30 may vary depending on the application in which the tip 30 will be used. For example, fewer ports 180 may be needed when only cooling of thermal element 20 is desired or when the thermal element is very small. In contrast, more ports 180 may be advantageous when both cooling of the thermal element 20 and irrigation of a surgical field is desired, or when a relatively large thermal surgical element is being used.

Figure 34:
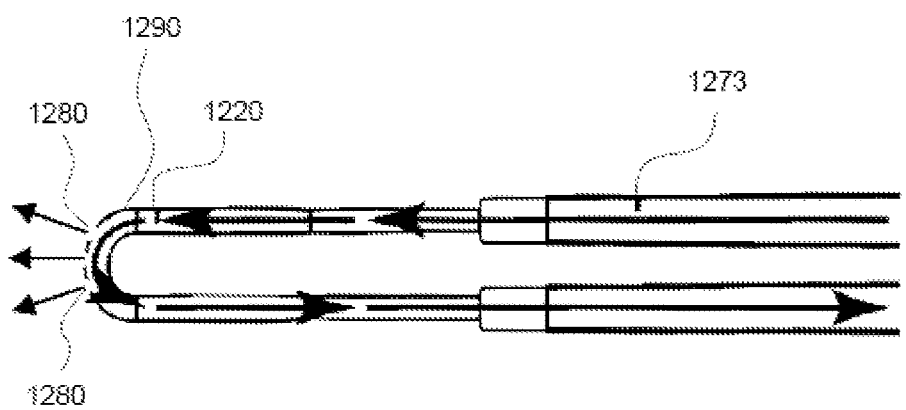
FIG. 34 shows a side view of a tip with hollow tip cooling.

Turning now to FIG. 34, a side view of a hollow thermal element is shown. According to one aspect of the invention, a handpiece may include a hollow thermal element 1220 with hollow electrical connections, such as hollow conductive stand-offs 1273, similar to the thermal element described above with respect to FIG. 16B. The hollow thermal element 1220 (which could be element 20 in the previous figures) and hollow electrical connections 1273 may be fluidly connected so that fluid may pass through the hollow areas. The thermal element may also be directly connected to a coolant flow line.

The thermal element 1220 may have one or more apertures 1280 that allows at least a portion of the fluid to be released from the thermal element 1220. Depending on how the solution is used, the solution can be used to soothe tissue or to blanch or destroy tissue.

In one use, the fluid may be directed into a surgical site to cool tissues therein. For example, a saline solution may originate from an external pump fluidly connected to the handpiece. The saline may be pumped through the handpiece into the electrical connections 1273 and the thermal element 1220, and back out to the external pump. If an adequate amount of saline solution is used, the saline solution may cool the tip and some saline may be released through the apertures to quench tissue which has been thermally treated with the thermal element 1220.

According to another aspect of the invention, the thermal element 1220 may receive sufficient power to heat the thermal element to a high temperature (e.g. about 400-500 degrees Centigrade), in the absence of a cooling fluid flowing through the hollow thermal element. However, when a liquid, such as saline, is used as the cooling fluid and directed through the hollow thermal element 1220 the temperature of the hollow thermal element 1220 may be clamped at about 100 degrees Centigrade due to the liquid changing phases from liquid to gas. Steam may be released through the one or more apertures 1280 and directed into a surgical site to blanch tissue or otherwise treat tissue with steam from the handpiece.

According to one aspect of the invention, the hollow thermal element 1220 may comprise a ferromagnetic material, such as Niron. According to another aspect of the invention, the hollow thermal element may comprise a hollow electric conductor having a ferromagnetic material 1290 disposed on the outer or inner surface of the hollow electrical conductor. In such a configuration, electrical energy may pass through the hollow electrical conductor to cause inductive heating by the ferromagnetic material. It will be appreciated that the ferromagnetic material may extend along substantially the full length of the inner or outer surface of the hollow electrical conductor.

Figure 35:
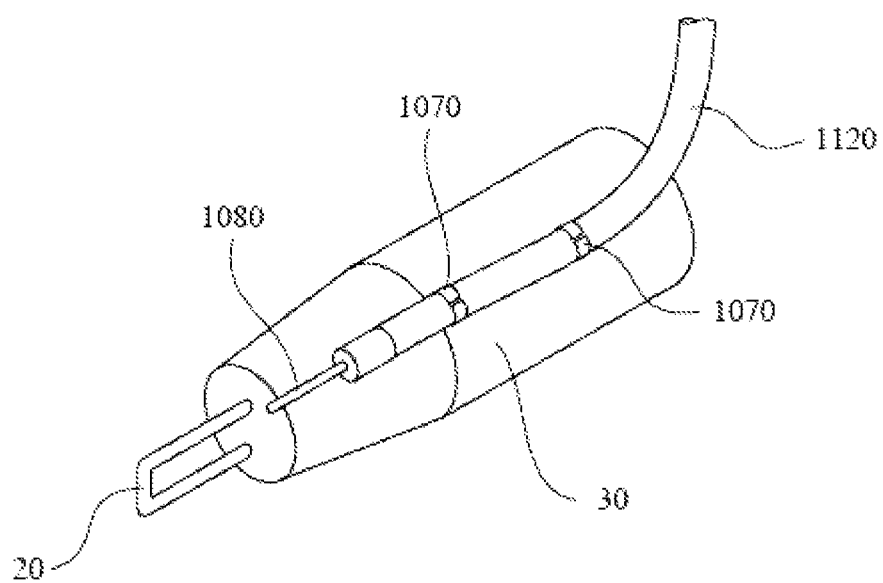
FIG. 35 shows a perspective view of a tip for a heated surgical instrument with an attachment member for receiving the tubing of a fluid drip line according to one aspect of the present invention.

Referring now to FIG. 35, a perspective view of the tip 30 for a heated surgical instrument with one or more attachment members 1070 for receiving the tubing 1120 of a fluid drip line is shown. Rather than having the tubing 1120 attach to a fluid connection site 60 and travel through at least a portion of the handpiece 40 (or other embodiments described above), tubing 1120 may be connected to the tip 30 via one or more attachment members 1070. Attached to tubing 1120 may be a needle 1080, or some other conduit sufficient for delivering cooling fluid to the thermal/surgical element 20 or to the surgical site.

Needle 1080 may be located adjacent to the thermal element 20 so that fluid may be directed on to thermal element 20, which in turn cools thermal element 20. Alternatively, needle 1080 may be located so that the tip of needle extends away from thermal element 20 to allow for irrigation of the surgical field without necessarily cooling the thermal element 20. It will be appreciated, in accordance with one aspect of the present invention, that the handpiece 40 can be cooled with a cooling system similar to that discussed above independent of the cooling fluid applied to the element 20 and/or the wound being irrigated/cooled.

Figure 36:
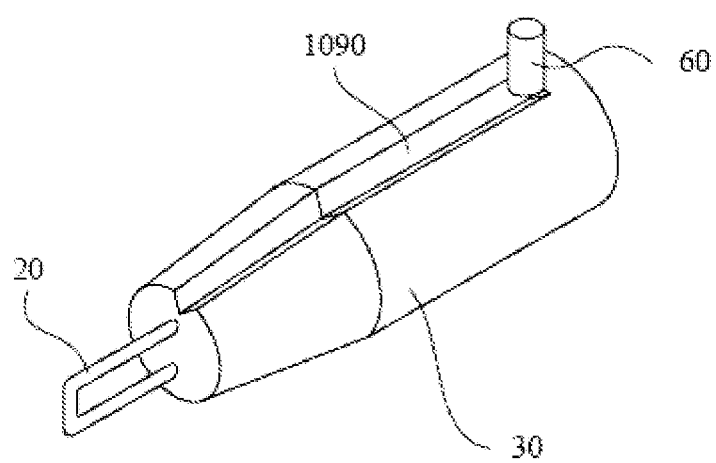
FIG. 36 shows a perspective view of a tip for a heated surgical instrument with a channel for delivering fluid.

FIG. 36 shows a perspective view of a tip 30 for a heated surgical instrument with a channel 1090 for delivering fluid. Tubing from a fluid drip line may be connected to a fluid connection site or port 60 so that when in use fluid, such as saline, water, etc., may flow from intake 60, down channel 1090, and onto thermal element 20 and/or into the surgical field to quench tissue or other materials therein. It will be appreciated that a handpiece may be used with several different tips 30 which may include different attachments and cooling fluid spray configurations to adapt the surgical instrument to the needs of the surgeon.

Figure 37:
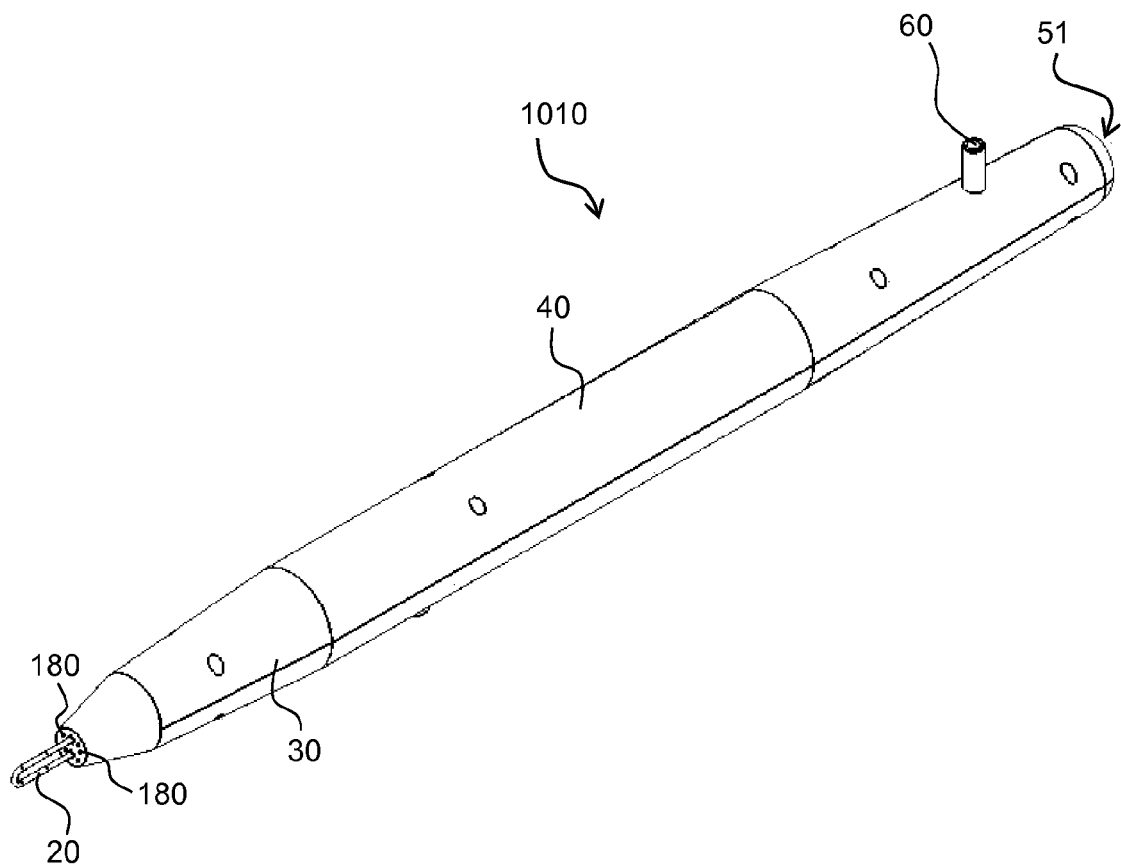
FIG. 37 shows a perspective view of a heated surgical instrument with an intake for receiving a fluid drip line located at a distal end of the instrument.

Turning to FIG. 37, a perspective view of a heated surgical instrument, generally indicated at 1010, is shown. The instrument 1010 may include a handpiece 40 with a fluid connection site 60 located at a distal end of the instrument. It will be appreciated that, in accordance with principles of the present invention, the fluid connection site 60 may be located at various sites on the heated surgical instrument 1010 and may be disposed on the handpiece 40 and/or on the tip 30. Liquid that is received by the fluid connection site 60 may be delivered to thermal element 20, or adjacent to the element, through a void or conduit located inside tip 30. Liquid may pass through the void or conduit and exit through one or more apertures 180 adjacent the thermal element 20. Liquid that contacts the thermal element 20 may cool the thermal element 20 by evaporating, while excess liquid may flow into the surgical site to quench tissue or other materials exposed to the high temperature of the heated surgical instrument. Liquid may also circulate inside the handpiece 40 to cool structures located therein and exit at a second location, such as a rear exit 51, similar to some of the airflow diagrams discussed above.

Figure 38:
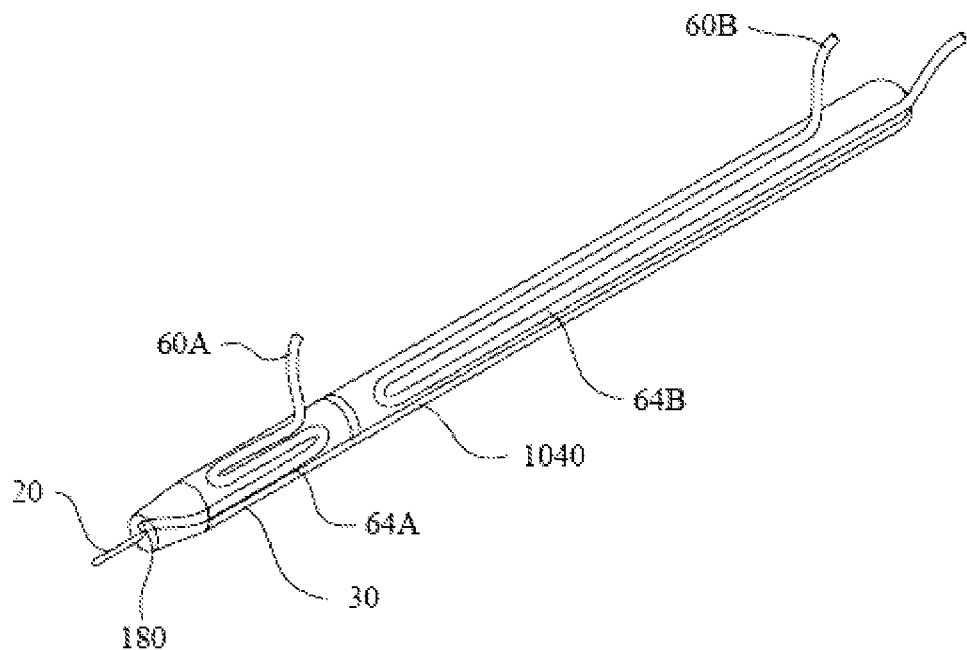
FIG. 38 shows a cut-away view of an alternate configuration of a handpiece.
Figure 38A:
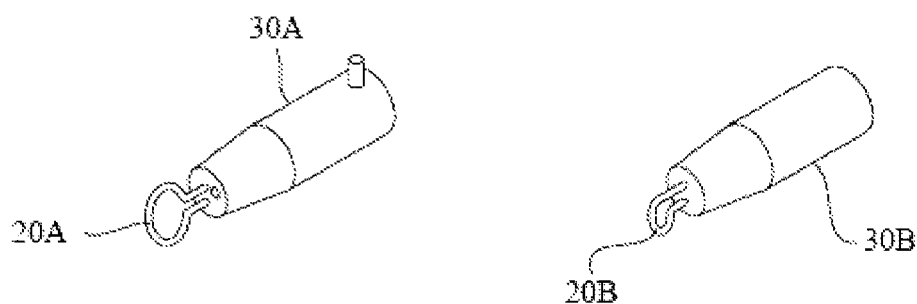
FIG. 38A shows two alternative tips which may be used with the handpiece of FIG. 38.

As was mentioned previously, the handpiece 40 may be cooled independently of the solution being directed at the element 20 or wound, or the same cooling fluid may be used for both purposes. Thus, the handpiece 40 can be configured in a similar manner as discussed above, or separate cooling structures may be provided as is shown in FIG. 38. The handpiece 40 may include a first fluid connection site 60A and conduit 64A in the tip 30 which is used to cool the tip (i.e. primary section) and to direct cooling fluid to the thermal element 20 and wound if desired. The secondary section of the handpiece 40 may have a second fluid connection site 60B which, with a conduit 64B, is used to cool the remainder of the handle. This allows a surgeon to independently regulate cooling in the two portions of the handpiece 40 and to select the pattern for coolant application to the thermal element 20 and or wound by changing tips 30, some of which may have no cooling mechanism at all. Thus, for example, FIG. 38A shows two replacement tips 30A and 30B, one having cooling and a different thermal element 20A and the other having a different thermal element 20B and no cooling.

There is thus disclosed an improved fluid cooled heated surgical instrument which may deliver a fluid adjacent a thermal element of the heated surgical instrument to cool the thermal element and/or irrigate a surgical field. It will be appreciated that numerous changes may be made to the present invention without departing from the scope of the claims.

What is claimed is:

1. A thermal surgical instrument comprising:
    a body comprising a body housing, a first conduit disposed in the body housing, and a fluid connection site disposed in fluid communication with the first conduit;
    a surgical tip comprising a tip housing and a hollow thermal element extending from the tip housing;
    wherein the surgical tip is in communication with the body housing such that at least a portion of the surgical tip is in fluid communication with the first conduit; and
    wherein the first conduit, the body housing, and the hollow thermal element form a coolant flow pathway for cooling the thermal surgical instrument.

2. The thermal surgical instrument according to claim 1, wherein the surgical tip is removably engageable with the body.

3. The thermal surgical instrument according to claim 1, wherein the surgical tip further comprises a second conduit, and wherein the surgical tip engages the body such that the second conduit is in fluid communication with the first conduit.

4. The thermal surgical instrument according to claim 2, wherein the body housing further comprises a recess having a shape and wherein the tip housing has a shape complimentary to the shape of the recess, wherein the shape of the recess and the shape of the tip housing facilitate alignment and engagement of the surgical tip to the body.

5. The thermal surgical instrument according to claim 2, wherein the body further comprises at least one alignment member to facilitate alignment and engagement of the surgical tip to the body.

6. The thermal surgical instrument according to claim 1, wherein the surgical tip further comprises at least one aperture in the surgical tip for creating a coolant flow pathway directed toward the thermal element.

7. The thermal surgical instrument according to claim 1, wherein the surgical tip further comprises an elongate tube having a distal end and a proximal end, wherein the distal end of the elongate tube is connected to the tip housing and wherein the thermal element is attached at the proximal end of the elongate tube.

8. The thermal surgical instrument according to claim 7, wherein the elongate tube comprises two concentric tubes having a void there through, and wherein the elongate tube further comprises an insulating material disposed between the two concentric tubes.

9. The thermal surgical instrument according to claim 8, wherein the elongate tube further comprises an outer tube, wherein the outer tube is disposed around the two concentric tubes such that there is a space between the outer tube and the two concentric tubes.

10. The thermal surgical instrument according to claim 9, wherein the space between the outer tube and the two concentric tubes and the void through the two concentric tubes form part of the coolant flow pathway.

11. The thermal surgical instrument according to claim 9, further comprising a spline disposed between the outer tube and the two concentric tubes.

12. The thermal surgical instrument of claim 1, wherein the tip housing is formed integrally with the body housing.

13. A method of cooling a thermal surgical instrument comprising the steps of:
    selecting a thermal surgical instrument comprising a ferromagnetic thermal element, a housing having a coolant flow pathway, and a fluid connection site, the housing having a tip housing and the ferromagnetic thermal element extending outwardly from the tip housing;
    connecting the fluid connection site to a device to provide a cooling fluid to the thermal surgical instrument; and
    directing cooling fluid through the coolant flow pathway to remove heat from the thermal surgical instrument.

14. The method according to claim 13, wherein cooling fluid is directed into the thermal surgical instrument through the fluid connection site.

15. The method according to claim 14, wherein the device connected to the fluid connection site is a suction device, and wherein cooling fluid is drawn into the coolant flow pathway and exits through the fluid connection site.

16. The method according to claim 14, further comprising disposing at least one aperture on the thermal surgical instrument, wherein the at least one aperture is in fluid communication with the coolant flow pathway so that at least a portion of the cooling fluid is released from the thermal surgical instrument through the at least one aperture.

17. The method according to claim 16, wherein cooling fluid released from the at least one aperture is directed toward the thermal element.

18. The method according to claim 16, wherein the cooling fluid is liquid, and wherein at least a portion of the liquid released from the at least one aperture is directed into a surgical site to quench tissue which has been contacted by the thermal element.

19. The method according to claim 14, wherein the thermal element is a hollow thermal element, and wherein the hollow thermal element is in fluid communication with the coolant flow pathway so as to direct cooling fluid through the hollow thermal element.

20. The method according to claim 19, wherein the hollow thermal element further comprises at least one aperture so that at least a portion of the cooling fluid is released from the at least one aperture in the hollow thermal element and directed toward a tissue being treated.

21. A method of cooling a surgical handpiece comprising:
    causing a coolant to flow through an inside first portion of a tip;
    reversing the direction of the coolant flow adjacent the first portion of the tip; and
    causing the coolant to flow through an inside second portion of the tip.

* * * * *